(12) United States Patent  
Martin

(10) Patent No.: US 9,775,726 B2
(45) Date of Patent: Oct. 3, 2017

(54) ELECTRONICALLY CONTROLLED PROSTHETIC SYSTEM

(71) Applicant: James Jay Martin, Oklahoma City, OK (US)

(72) Inventor: James Jay Martin, Oklahoma City, OK (US)

( * ) Notice: Subject to any disclaimer, the term of this patent is extended or adjusted under 35 U.S.C. 154(b) by 0 days.

(21) Appl. No.: 15/092,231

(22) Filed: Apr. 6, 2016

(65) Prior Publication Data

US 2016/0278947 A1    Sep. 29, 2016

Related U.S. Application Data

(63) Continuation-in-part of application No. 14/221,457, filed on Mar. 21, 2014, now abandoned, which is a
(Continued)

(51) Int. Cl.
*A61F 2/66* (2006.01)
*A61F 2/72* (2006.01)
(Continued)

(52) U.S. Cl.
CPC ............ *A61F 2/6607* (2013.01); *A61B 5/112* (2013.01); *A61B 5/4851* (2013.01); *A61F 2/68* (2013.01); *A61F 2/70* (2013.01); *A61F 2/72* (2013.01); *A61F 2/581* (2013.01); *A61F 2/582* (2013.01); *A61F 2/605* (2013.01); *A61F 2/64* (2013.01); *A61F 2002/5004* (2013.01); *A61F 2002/5006* (2013.01); *A61F 2002/5018* (2013.01); *A61F 2002/5033* (2013.01); *A61F 2002/5035* (2013.01); *A61F 2002/5036* (2013.01); *A61F 2002/5038* (2013.01); *A61F 2002/5049* (2013.01); *A61F 2002/6614* (2013.01); *A61F 2002/6621* (2013.01); *A61F 2002/6628* (2013.01); *A61F 2002/6642* (2013.01); *A61F 2002/6685* (2013.01); *A61F 2002/6818* (2013.01); *A61F 2002/6827* (2013.01);
(Continued)

(58) Field of Classification Search
CPC .. A61F 2/66; A61F 2/6607; A61F 2002/7625; A61F 2002/6657; A61F 2002/6664
USPC ...................................... 623/24–26
See application file for complete search history.

(56) References Cited

U.S. PATENT DOCUMENTS

| 6,443,993 | B1 * | 9/2002 | Koniuk | ................. | A61F 2/6607 623/24 |
| 7,029,500 | B2 * | 4/2006 | Martin | ................. | A61F 2/6607 623/24 |

(Continued)

*Primary Examiner* — Bruce E Snow
(74) *Attorney, Agent, or Firm* — Phillips Murrah PC; Martin G. Ozinga

(57) ABSTRACT

A prosthetic joint system for users comprising a housing having an interior cavity, a center axis in said interior cavity, and an attachment means for fixedly connecting said housing to said user; an inner cylinder disposed in said housing interior cavity wherein said inner cylinder rotates around said center axis of said housing; an appendage attached to said inner cylinder; a sensor system attached to said appendage; and a dampening system, having a power source, in communication with said sensor system, said inner cylinder, and said housing for controlling dampening of the rotation of said inner cylinder around said center axis of said housing.

1 Claim, 38 Drawing Sheets

Related U.S. Application Data continuation-in-part of application No. 13/351,291, filed on Jan. 17, 2012, now abandoned, which is a continuation of application No. 12/979,434, filed on Dec. 28, 2010, now abandoned, which is a continuation of application No. 12/185,907, filed on Aug. 5, 2008, now abandoned, which is a continuation-in-part of application No. 11/953,390, filed on Dec. 10, 2007, now abandoned, which is a continuation of application No. 11/801,790, filed on May 11, 2007, now abandoned, which is a continuation-in-part of application No. 11/343,066, filed on Jan. 30, 2006, now Pat. No. 7,393,364, which is a continuation of application No. 10/410,491, filed on Apr. 9, 2003, now Pat. No. 7,029,500.

(60) Provisional application No. 60/371,974, filed on Apr. 12, 2002.

(51) Int. Cl.
*A61B 5/11* (2006.01)
*A61B 5/00* (2006.01)
*A61F 2/50* (2006.01)
*A61F 2/68* (2006.01)
*A61F 2/70* (2006.01)
*A61F 2/74* (2006.01)
*A61F 2/58* (2006.01)
*A61F 2/60* (2006.01)
*A61F 2/64* (2006.01)
*A61F 2/76* (2006.01)

(52) U.S. Cl.
CPC ... *A61F 2002/701* (2013.01); *A61F 2002/704* (2013.01); *A61F 2002/705* (2013.01); *A61F 2002/745* (2013.01); *A61F 2002/764* (2013.01); *A61F 2002/769* (2013.01); *A61F 2002/7625* (2013.01); *A61F 2002/7635* (2013.01); *A61F 2002/7645* (2013.01); *A61F 2002/7665* (2013.01)

(56) References Cited

U.S. PATENT DOCUMENTS

| | | | |
|---|---|---|---|
| 7,393,364 B2* | 7/2008 | Martin | A61F 2/6607 623/24 |
| 7,578,852 B2* | 8/2009 | Townsend | A61K 9/4816 623/53 |
| 9,265,627 B2* | 2/2016 | Kramer | A61F 2/76 |
| 2011/0107581 A1* | 5/2011 | Williams | A61F 2/5044 29/428 |

* cited by examiner

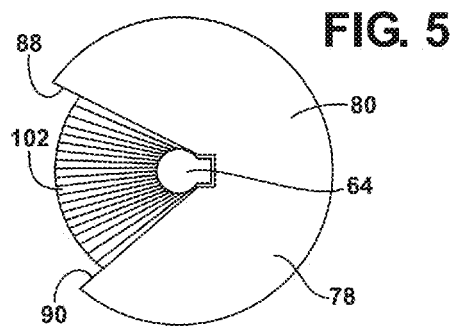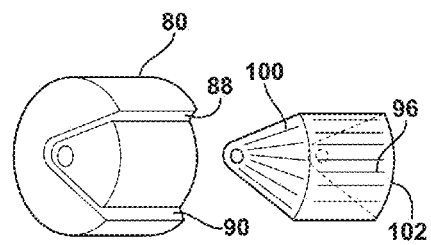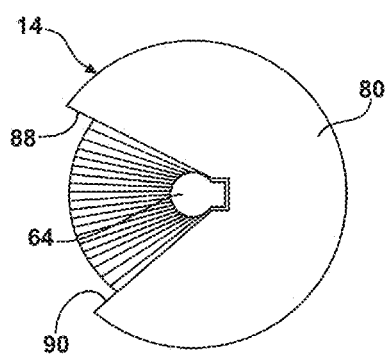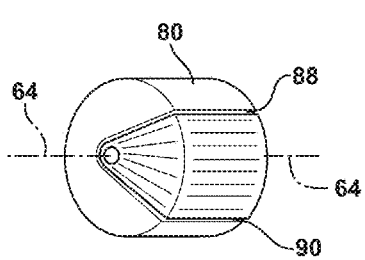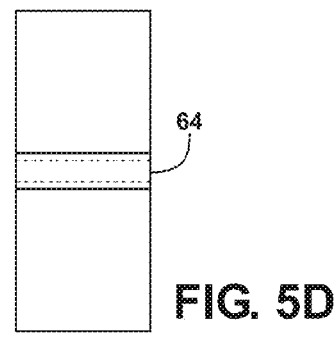

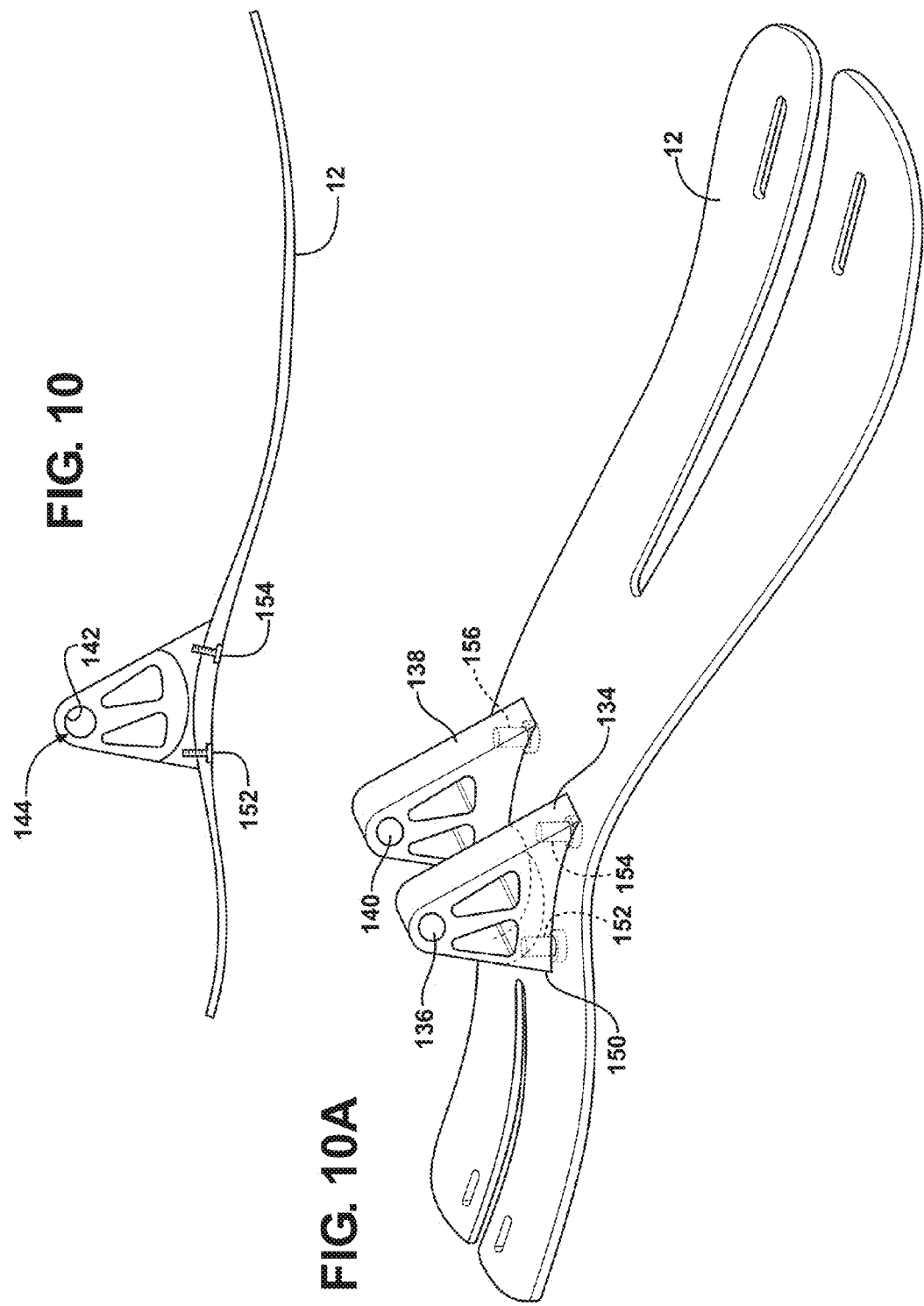

FIG. 12C
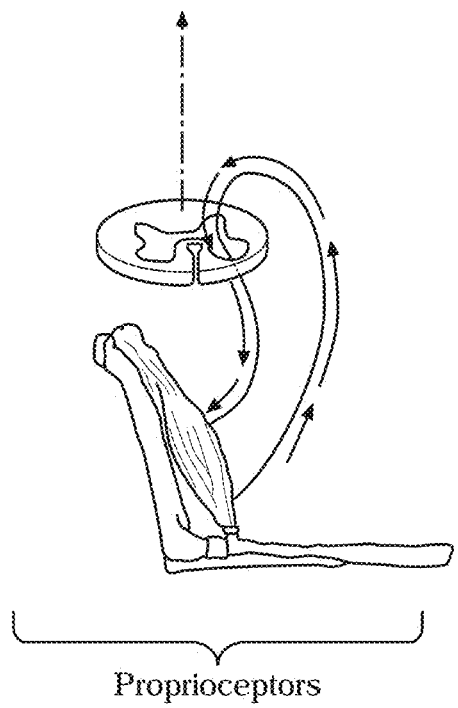
Proprioceptors
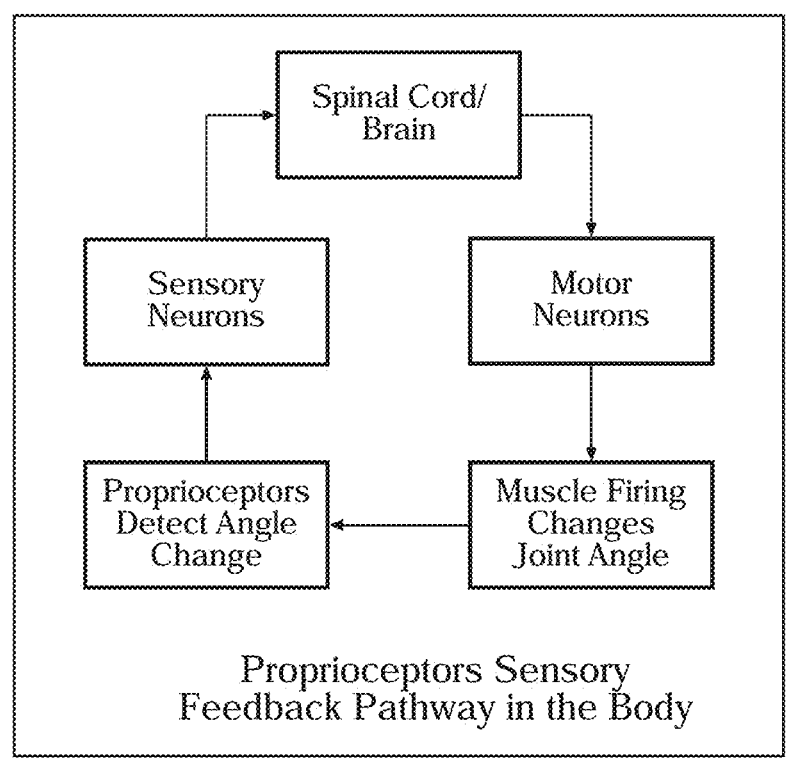
FIG. 12D

FIG. 12H
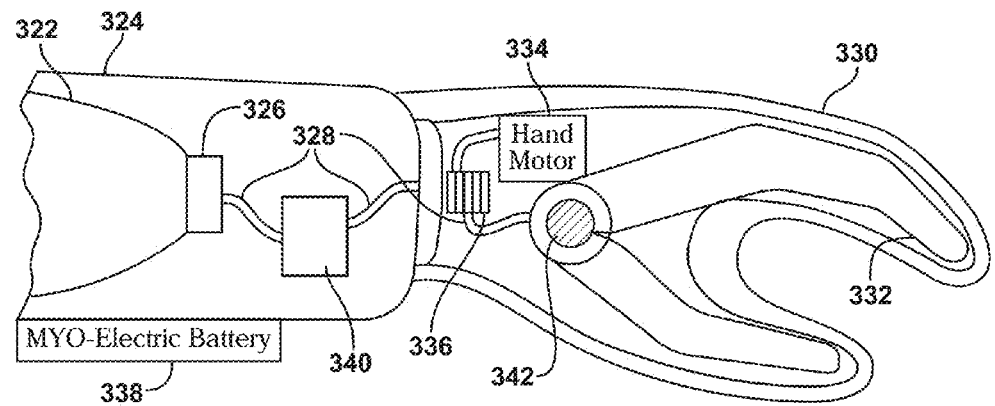
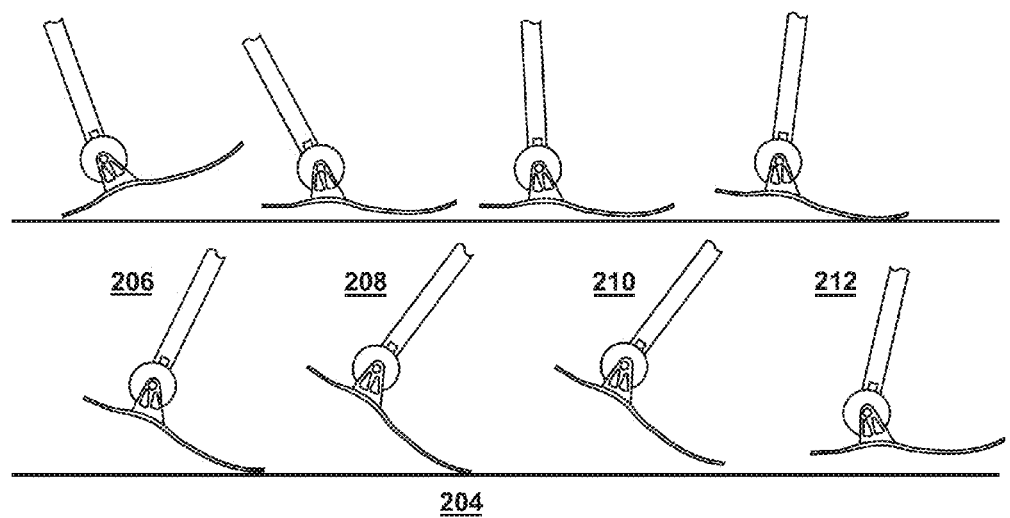
FIG. 13

FIG. 14B
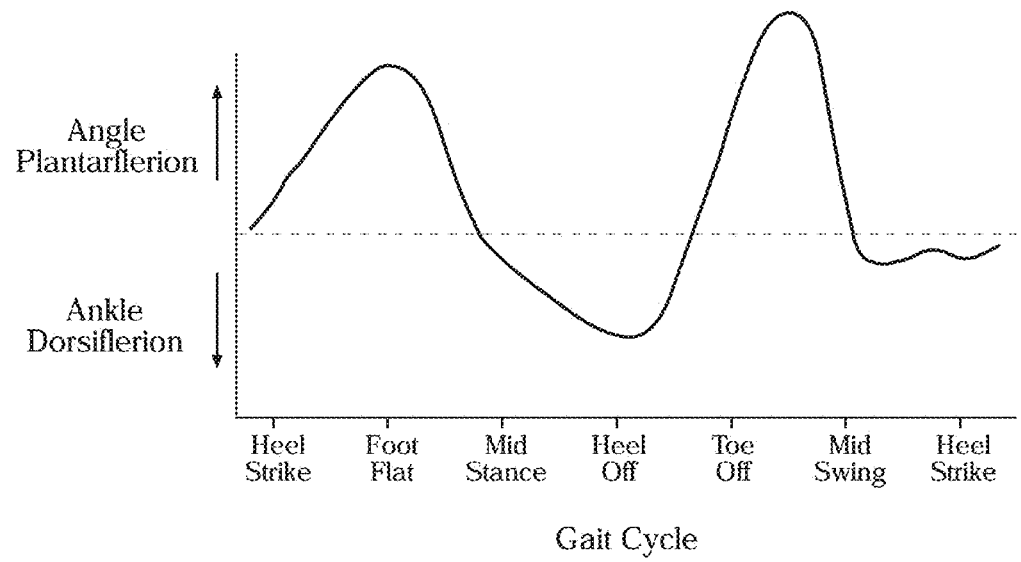
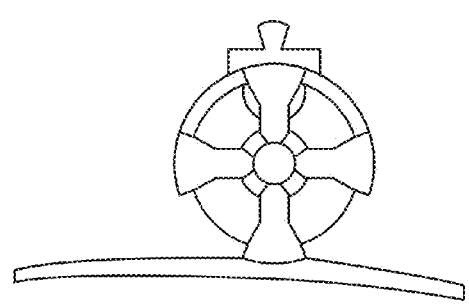
FIG. 15A
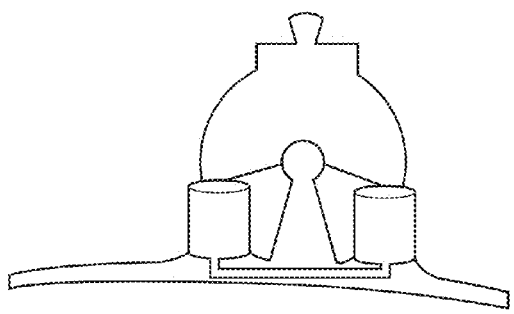
FIG. 15B
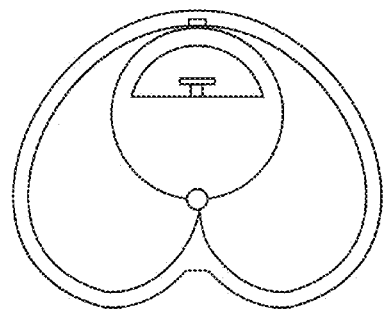
FIG. 16

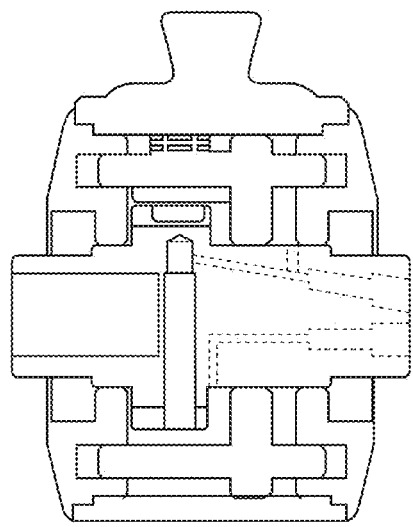 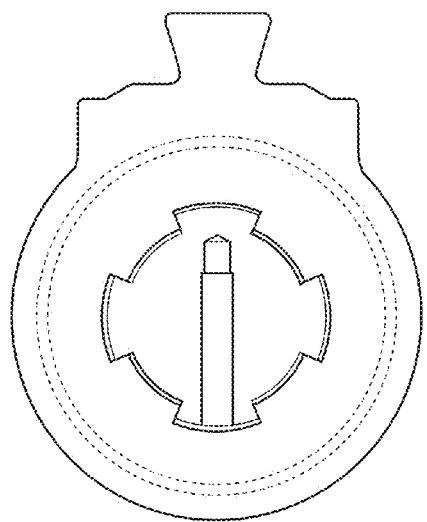
FIG. 22A        FIG. 22B
FIG. 23A
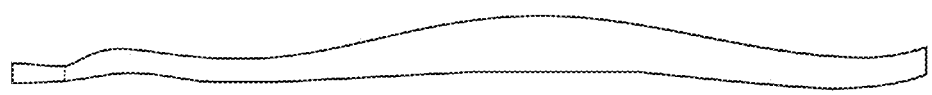
FIG. 23B

Fig. 42
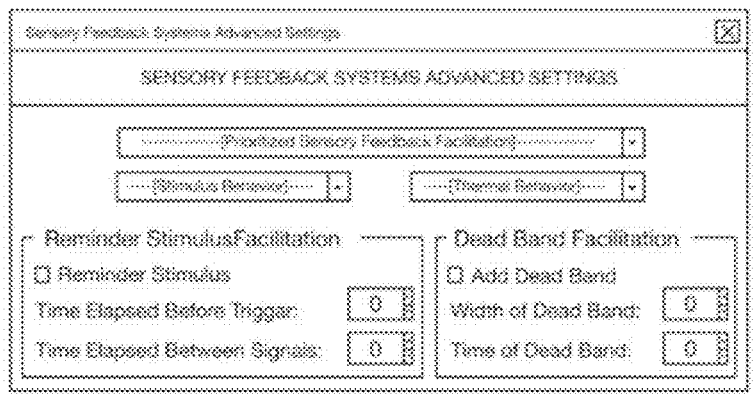
Fig. 43
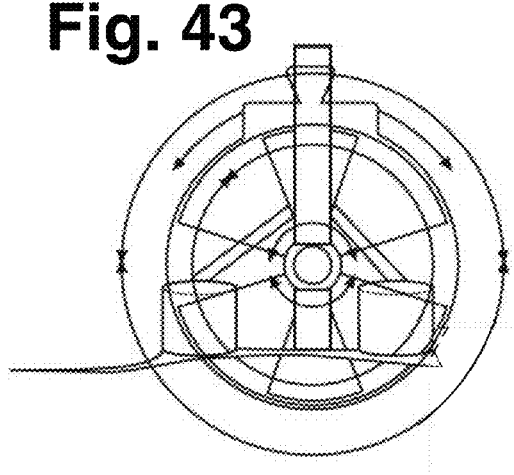
Fig. 44
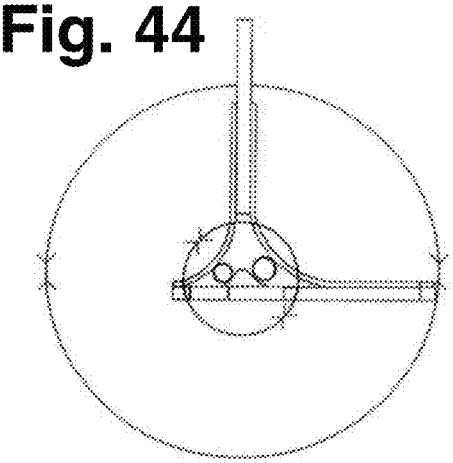
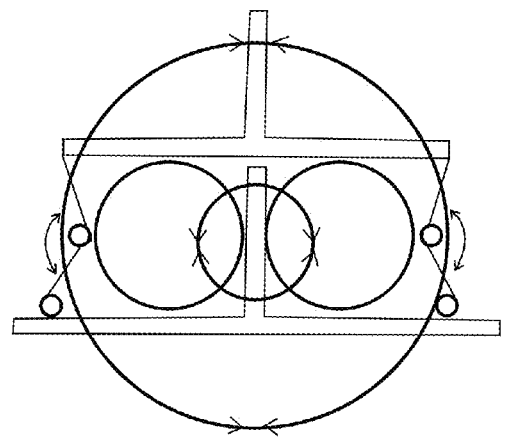
Fig 45A
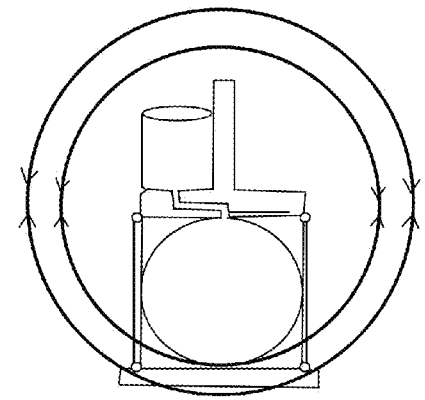
Fig 45B

ELECTRONICALLY CONTROLLED PROSTHETIC SYSTEM

CROSS-REFERENCE TO RELATED APPLICATIONS

This application is a continuation-in-part of U.S. patent application Ser. No. 14/221,457, filed Mar. 21, 2014, which is a continuation-in-part of U.S. patent application Ser. No. 13/351,291, filed Jan. 17, 2012, now abandoned, which is a continuation of U.S. patent application Ser. No. 12/979,434, filed Dec. 28, 2010, now abandoned, which is a continuation of U.S. patent application Ser. No. 12/185,907, filed Aug. 5, 2008, now abandoned, which is a continuation-in-part of U.S. patent application Ser. No. 11/953,390, filed Dec. 10, 2007, now abandoned, which is a continuation of U.S. patent application Ser. No. 11/801,790, filed May 11, 2007, now abandoned, which is a continuation-in-part of U.S. patent application Ser. No. 11/343,066, filed Jan. 30, 2006, now U.S. Pat. No. 7,393,364, issued Jul. 1, 2008, which is a continuation of U.S. patent application Ser. No. 10/410,491, filed Apr. 9, 2003, now U.S. Pat. No. 7,029,500, issued on Apr. 18, 2006, which is based on U.S. Provisional Application Ser. No. 60/371,974, filed on Apr. 12, 2002. The entire content of each of the above-referenced applications is hereby expressly incorporated herein by reference.

FIELD OF THE INVENTION

The present invention relates generally to an ankle and foot joint system. More particularly, the present invention is a new and improved prosthetic joint system, which simulates natural human locomotion, and human biomechanics through sensory feedback, time feedback, electronically controlled dampening joint assembly, and a microprocessor control system.

BACKGROUND OF THE INVENTION

As the study of human physiology and anatomy clearly demonstrates, the relative simple action of walking on an even flat surface involves numerous biomechanical complexities. A single step requires constant biofeedback such as continual analysis of proprioception, angulations, timing, and balanced muscular-skeletal functions. In the prior art, the prosthetic industry is continuously attempting to mimic natural human locomotion (NHL), performance and aesthetics.

The field of prosthetics, in general, has made enormous advances in improving amputee and congenitally deformed individuals' performance on multiple levels from general ambulation to competitive sports through improved technology and understanding of human biomechanics. Although, it is known in the art to manufacture ankle and foot prosthetic combinations that have generally increased performance and appearance, the prior art is still deficient on numerous levels as will be discussed in greater detail below.

Many prosthetic feet are optimized for a small or limited range of activities. Typically, models aligned for such activities as daily walking are not optimally aligned for running and vice versa. It is, therefore, desirable to provide a design that allows a user to go from walking to running to provide greater user flexibility in multiple activities. Furthermore, while prior art prosthetic devices may have generally moved amputees toward more biomechanically appropriate gait patterns, current mechanically controlled designed prosthetic feet do not allow for significant alterations in gait speed without losing optimal biomechanical characteristics essential with walking or running. Still furthermore, it is desirable to provide a design that allows transition from flat ground to moving up hill or from flat ground to moving downhill with ease, safety, function, and generally traversing uneven surfaces, where the prior art is lacking.

There are models in the prior art that are characterized by the term ENERGY STORING that may provide greater energy return than other models through spring-return characteristics of the keel members to lessen energy expenditures. Additionally, models that provide MULTI-AXIAL uneven ground accommodation have been developed to better assist users to gain better balance on real-world environments. Unfortunately, neither of these categories of advancements provides both optimal energy return and uneven ground accommodation sufficiently to meet user needs in all activities and in all environments. While numerous prosthetic feet and ankle systems are available in the market, no mechanical based prosthetics provide full mimicking of their anatomical counterpart. It is now contemplated that optimal biomechanical and natural human locomotion functions cannot come solely through a relative simple mechanical device such as found in much of the existing prior art.

By example in non-ankle and foot prosthetics, it has been observed in a microprocessor controlled C leg knee design by the company OTTO BOCK that amputees are able to have better gait symmetry, decreased energy expenditure, and a much greater sense of mental confidence in ambulating than non-microprocessor prosthetic knees, however, there remains a significant gap between the most advanced prosthetics and the human body. Therefore, there remains a need to greatly improve the functional abilities of the prosthetic system, and hence, the abilities of the amputee. It is now contemplated that similar benefits could be observed through this type of design but for a broader spectrum of amputees, including trans-tibial amputees, through the use of a computer controlled prosthetic ankle and foot system with appropriate sensory feedback mechanisms. Through this disclosure, an improved prosthetic control system is discussed which more closely mimics the natural control functions of the human body.

Another consideration lacking in the prior art of ankle and foot devices is the combination of aesthetics and function. It is desirable to provide a prosthetic foot that also has a much more cosmetic effect through better simulating proper natural human locomotion and allows the foot to plantarflex during sitting to better simulate a real ankle and foot. In this manner, a user's foot and ankle would appear more normal than the telltale sign of a prosthetic that juts unnaturally up when sitting.

Oftentimes, aesthetics is sacrificed for increased function. A common complaint of many prosthetic foot users, for instance is that their prosthetic foot "sticks up" with unnatural dorsiflexion angle when they sit. This remains a problem due to the prior art prosthetic feet being relatively affixed at a given angle with respect to the prosthesis, thus, during sitting the foot remains pointing upwards as the shin section of the prosthesis has a posterior lean when the amputee is sitting. This is a major complaint of many prosthetic users, and has not been adequately addressed through commercially available prosthetics.

The OSSUR Proprio Foot design does allow for plantarflexion during sitting, however, it is does not take place in an aesthetically natural manner. After a few moments after sitting, the foot then plantarflexes through powered actuation. The design disclosed in this patent has the ability to naturally, and immediately plantarflex during sitting, accommodating for the natural angle of the shin with respect to the ground.

With robotics and advanced prosthetics, it is essential that the motion of the bio-replicating design match the natural movement of the anatomical counterpart in great detail. As the realistic nature of the prosthesis approaches that of the natural limb, in cosmetic physically and biomechanically similar characteristics, the psychological acceptance of the device becomes increasingly difficult. When a bio-resembling robotic device or advanced prosthesis offers enough dissimilarities from the natural limb, the psyche recognizes that it is not real and readily accepts the device, though the prosthetics user is often dissatisfied with the capabilities of the device by not replicating the body well enough. When the robotic or prosthetic device, however, approaches the upper limits of realism, a psychological effect referred to as the "Uncanny Valley" syndrome occurs, resulting in the user's dissatisfaction with the device, though it is more life-like than less biomechanically similar counterparts. It is imperative that the realistic nature of the advanced design illustrated here is capable of being fine-tuned to the natural movement of the user, in all conditions and in all environments, whereas to allow for full mental acceptance of the design being integrated as an accessory extension of the body. This disclosed design, unlike other prosthetics available in the field today, offers much more life-like appearance than conventional technology, such as in plantarflexion during sitting, and allows for fine-tuned adjustments of the movement to prevent the Uncanny Valley syndrome with respect to prosthetic acceptance.

Furthermore, the stubbing of a prosthetic foot has proven to be a safety issue for trans-tibial, trans-femoral, and hip-disarticulation amputees alike at all activity levels. This often occurs because many conventional prosthetic feet do not dorsiflex during the swing phase of gait, as occurs naturally. The prior art prosthetic feet have attempted to dorsiflex the foot during swing phase in the past, such as with the a prior art design under the trademark or name HYDROCADANCE, but have generally failed to provide the full range of benefits desired, such as being able to be used on a vast array of lower extremity amputees' functional abilities and amputation levels as well as provide optimal energy return characteristics, range of motion, and a life-like appearance, to name a few. The OSSUR Proprio Foot does allow for dorsiflexion during the swing phase of gait, but is unable to appropriately accommodate for the necessary dorsiflexion angle correlating to the terrain angle. Additionally, its dorsiflexion ability, and other movement characteristics, takes place over a series of steps, but does not occur in real-time, as this design does.

Still furthermore, it is desirable to have a functional prosthetic that may also allow a user to choose from various cosmetically shaped foot shells where the prior art fails. Though prosthetic feet are not commonly seen because they are frequently covered by shoes, cosmetic appearance is a very important aspect to many amputees and other users due to current lifestyle and fashion trends. It is therefore desirable to provide a device that may allow several foot shell templates to choose from or to have customized foot shell molds fabricated much like what is now available with upper extremity prosthetics cosmetic gloves.

What is needed is a prosthetic design utilizing electronics such as but not limited to a prosthetic microprocessor, sensory feedback mechanisms for various angle, time, and moment or pressure sensors, and actively providing a means for adjusting plantarflexion and dorsiflexion through prosthetic proprioception which will allow a user to transverse all necessary barriers with appropriate biomechanical precision, stability, and range of activities.

Furthermore, it is desirable to provide a design for a very active user who may want to perform daily activities and run, and which provides additional stability and safety for lower activity users who simply need to traverse low level barriers with enhanced safety and stability.

Still furthermore, one of the areas of prosthetics that is very much at its infancy stages is creating prosthetic sensory feedback mechanisms. It is believed that the better the mesh between the human and machine interactions, the more functional, safe, and life-like a user's abilities will become.

Currently found in prosthetic systems used today or in prosthetic research laboratories is the sense of feel system which generally attempts to correspond to human tactile receptors in extremities. The prosthesis detects pressure and stimulates the residual limb in a manner to trick the brain into thinking it is "feeling" with the prosthesis through cerebral projections. In essence, the prosthesis attempts to communicate or provide feedback to the user's brain.

Furthermore, there is also myoelectric control, which generally attempts interaction from muscular control of extremity muscles. The electrical activity from the muscular actions within the residual limb is picked up by electrodes embedded in, by example, the socket system and cause the prosthetic hand to move in an intended manner. In essence, the brain attempts to communicate or provide feedback to the prosthesis.

Still furthermore, it is understood to attempt a general prosthetic brain wherein correspondence to a sort or proprioception by having the microprocessor embedded in the prosthesis, along with an array of various sensors, cause the prosthetic joint to move in a fashion that matches up to the wearer's gait pattern and/or intended movement. By example in the prior art, the C-leg system uses a microprocessor or prosthetic brain to constantly analyze how fast it should flex and extend during the swing phase of gait, as well as how much stance stability to maintain during the stance phase of gait, amongst other actions. Such design generally mimics the motion of the sound limb independent of the terrain or slope, according to a pre-set determined set of variables. While this design does adjust its stance and swing characteristics, it does not provide do so in accordance with the anatomical limb's natural movement in all conditions and in all environment, and not in a full bio-replicating manner.

Although prosthetic technology has advanced in recent years, the prior art still has failed to bridge the gap between man-made prosthetics and user demand and needs. Likewise, there is also a desire to enhance the body/prosthesis integration through sensory feedback mechanisms and prosthetic proprioception. Therefore, an extensive opportunity for design advancements and innovation remains where the prior art fails or is deficient.

SUMMARY OF THE INVENTION

In general, the present invention is a new and improved prosthetic joint system which provides natural human locomotion and aesthetics where the prior art fails. The present invention generally provides a sensory and time feedback system that works in conjunction with a self-contained microprocessor to control and regulate a dampening system for a joint assembly that utilizes but is not limited to magnetorheological fluid, hydraulic fluid, oil, water, or saline solution, or other controllable fluid.

Without the intention of limitation, the invention may generally be comprised of a prosthetic foot, foot and ankle, or ankle unit, as well as having the inclusion of other joints such as but not limited to the knee and hip joints. Additionally, without the intention of limitation, the invention may generally comprise a keel being fixedly attached to an inner or outer cylinder. The inner or outer cylinder is generally disposed in a rotational manner to the other cylinder or housing which in turn is fixedly attached to a user's lower extremity. It is understood that the term cylinder may encompass a virtual arc segment about a fixed or moving axis, and should not be considered limiting. The inner cylinder rotation is generally controlled by a dampening system that may utilize magnetorheological, hydraulic, or other fluid that receives input from a microprocessor in communication with the sensors. The sensors that are used to provide information to the microprocessor may be located on the keel, brackets, damper, pylon, or other embodiments of the device. These sensor systems provide information as to the desired or intended movement for the control of the device.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Accordingly, titles, headings, chapters name, classifications and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved prosthetic joint system, and more particularly, a prosthetic ankle and foot system with the possible inclusion of knee and hip joints, that provides greater ease, safety, and function to a wide range of activities such as but not limited to moving from a walk to a run, transverse from flat ground to an uphill grade, or transverse from flat ground to a downhill grade.

It should be understood as well that the prosthetic system in general may comprise a foot and ankle only, for users who have their anatomical knee or who do not wish to utilize a more advanced knee unit. Furthermore, the system may comprise a foot and ankle and knee unit for those users with the need for both a prosthetic foot and knee unit. Still furthermore, the system may comprise a foot and ankle and knee and hip units, all working on conjunction with each other for those users who demand all these prosthetic joints of the leg due to a high level of amputation. For purposes of simplicity of explanation, the system may be described as foot, foot and ankle, or system, amongst other terms, but should not be considered limiting to the specific joints mentioned. It should be further understood that the method of communication, interaction, and control of each of the joints offers distinct similarities and should therefore be considered in unison during explanation where applicable.

Additionally, it is an object of the present invention to provide accommodation not only to slope alterations, but also to force and speed alterations as well.

It is a further object of the present invention to provide a new and improved prosthetic joint system which is a relatively simple design with few moving parts and thus may be easily and efficiently manufactured.

An even further object of the present invention is to provide a new and improved prosthetic joint system which is of a more durable and reliable construction than that of the existing known art.

Still another object to the present invention is to provide a new and improved prosthetic joint system which is susceptible of a low cost of manufacture with regard to both materials and labor, which accordingly is then susceptible of low prices of sale to the consuming public, thereby making such economically available to those in need of such prosthetic devices.

Another object of the present invention is to provide a new and improved prosthetic joint system which provides some of the advantages of the prior art, while simultaneously overcoming some of the disadvantages normally associated therewith.

Yet another object of the present invention to provide a new and improved prosthetic joint system, and more particularly a prosthetic ankle and foot system that is well suited for most function level K2-K4 amputees as well as benefit transtibial, transfemoral, hip disarticulation amputees and, generally, all levels of lower extremity amputees.

Still yet, another object of the present invention is to provide a new and improved prosthetic ankle and foot system that generally utilizes a keel design wherein energy return is optimized and uneven ground is more easily traversed.

A further object of the present invention is to provide a new and improved prosthetic ankle and foot system for multiple levels of amputation and addresses issues of gait for all activity levels by allowing the foot to dorsiflex through swing phase of gait thus greatly enhancing safety, decreasing mental anxiety, and increasing gait symmetry.

Still another object of the present invention is to provide a new and improved prosthetic ankle and foot system that provides cosmetic effect through better simulating proper natural human locomotion, allowing the foot to plantar flex during sitting, and features a more cosmetically shaped foot shell which may selectively be chosen from a variety of styles.

Another object of the present invention is to provide a new and improved dampening mechanism for artificial joints comprising MR fluid or other fluidly characterized system. The mechanism may be utilized on other prosthetic or orthotic joint systems. Furthermore, the mechanism may allow for retrofitting to prior art, readily available prosthetic feet and ankle joints.

An even further object of the present invention is to provide a new and improved prosthetic joint system, which may provide instantaneous communication from the prosthesis to the user wherein feedback is provided such that a sense of spatial and angular orientation of the prosthetic joint is achieved, as well as a sense of resistance to that angular change.

Still further, an object of the present invention is to provide a new and improved prosthetic joint system wherein instantaneous communication from the user to the prosthesis is achieved for better regulating, controlling, or positioning the prosthesis.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference would be had to the accompanying drawings and descriptive matter in which there are illustrated preferred embodiments of the invention.

BRIEF DESCRIPTION OF THE DRAWINGS

FIG. 5 is a side view of a preferred general construction of an inner cylinder in accordance with the present invention.

FIG. 5A is a partially exploded perspective view of a preferred general construction of an inner cylinder in accordance with the present invention.

FIG. 5B is a side view of a preferred general construction of an inner cylinder in accordance with the present invention.

FIG. 5C is a partially exploded perspective view of a preferred general construction of an inner cylinder in accordance with the present invention.

FIG. 5D is another side view of a preferred general construction of an inner cylinder in accordance with the present invention.

FIG. 10 is a side view of a preferred general construction of a keel and bracket assembly in accordance with the present invention.

FIG. 10A is a perspective view of a preferred general construction of a keel and bracket assembly in accordance with the present invention.

FIG. 12C is a general illustration depicting elements of a natural human system for proprioception feedback pathway.

FIG. 12D is a general illustration of a flow chart depicting elements of a natural human system for proprioception feedback pathway.

FIG. 12H is a sketch or schematic representation generally depicting a preferred embodiment of the invention wherein sensory feedback is supplied from the invention to a user.

FIG. 13 is a general illustration depicting a preferred construction of the invention throughout gait cycle.

FIG. 14B is a graphical presentation showing general characteristics of natural human muscle ankle angle during a gait cycle.

FIGS. 15A and 15B depict two embodiments of a two chamber system, comparing equivalency between them.

FIG. 16 is a general illustration depicting a two chamber damper with offset axis of rotation with respect to the mechanical embodiment.

FIGS. 22A and 22B illustrate two views of a damper mechanism used to convert rotary to linear motion within a two chamber design.

FIG. 23A is a general illustration depicting a medial view of a keel design; and FIG. 23B depicts a lateral view of the keel design.

FIG. 33 is a general illustration depicting a patient or user information page for a control program.

Figure 38:
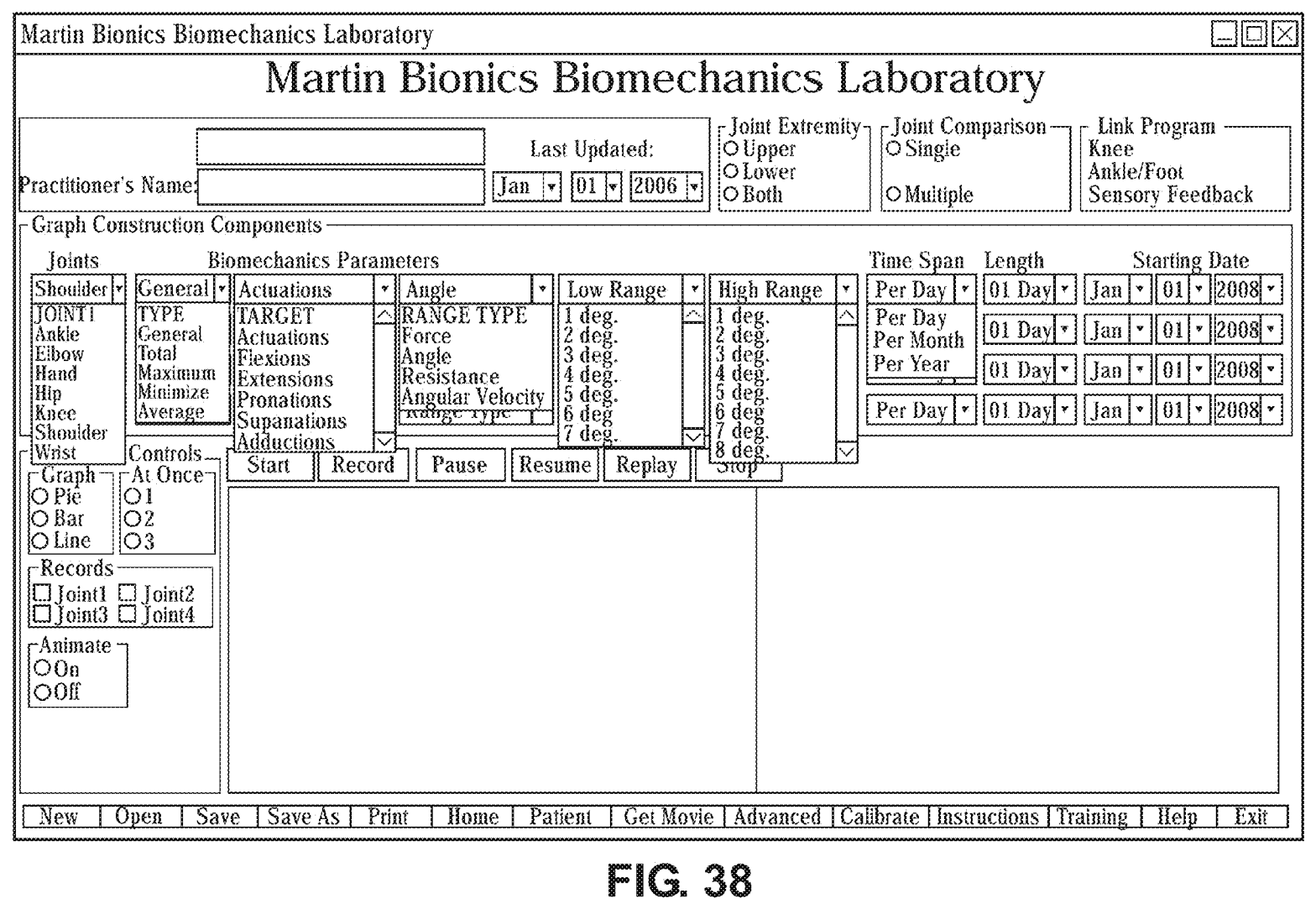

FIG. 38 is a general illustration depicting further variables for a biomechanics data capturing system.

Figure 41:
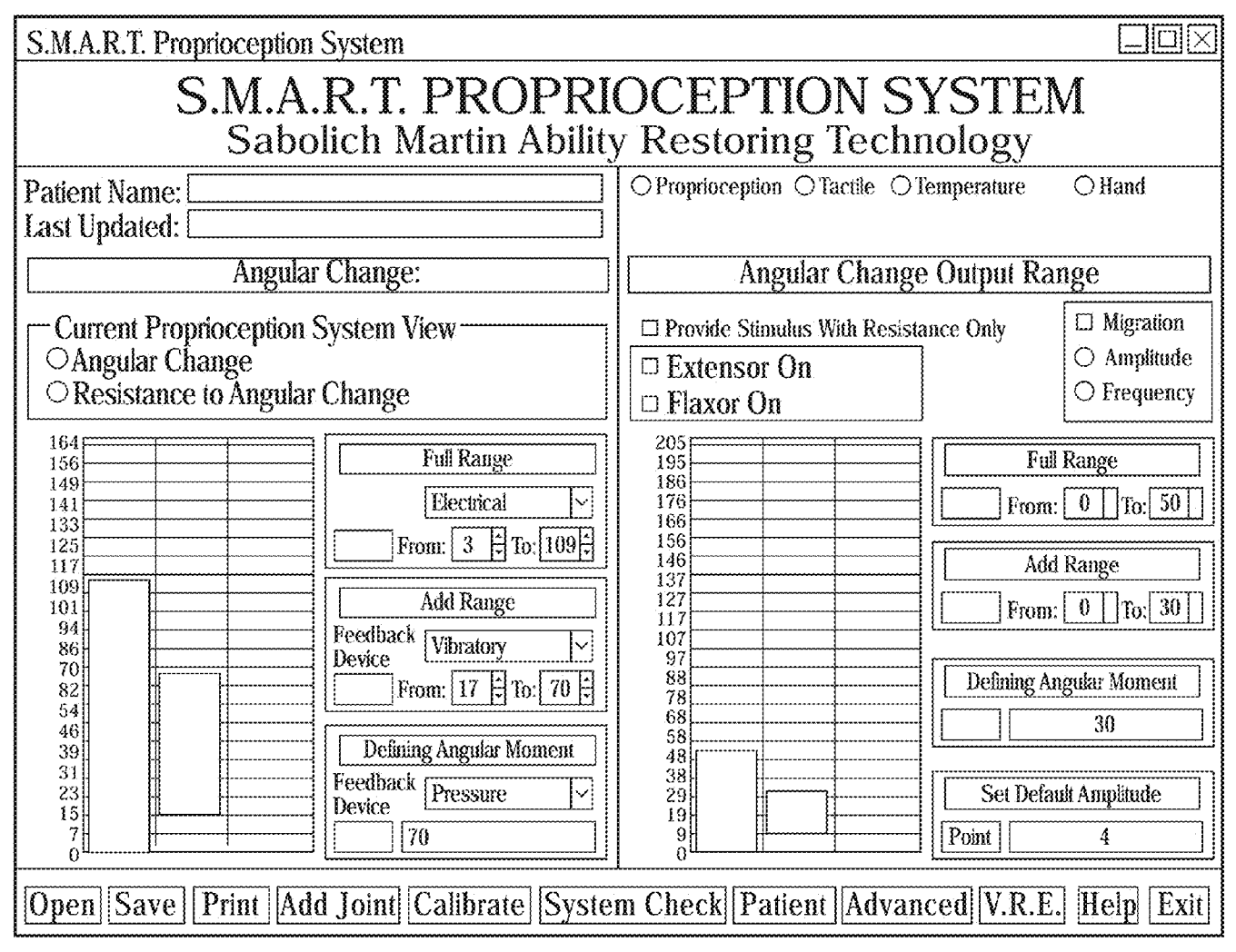

FIG. 41 is a general illustration of a sensory feedback tailoring software system that can be used to refine the feedback to the user based off of sensor information from the device and its function.

FIG. 42 is a general illustration of further control variables of a sensory feedback system.

FIG. 43 is a general illustration depicting the relation of inner and outer cylinders for various illustrations of the same disclosure overlaid.

FIG. 44 is a general illustration depicting an inner and outer cylinder equivalent in motion with two fluid chambers, an axis of rotation, and valve system. This implementation offers equivalency to other depicted designs.

FIG. 45A and FIG. 45B are general illustrations depicting two fluid filled compartments, an inner and outer cylinder equivalent in motion with an axis of rotation, and valve system. FIG. 45A is a side view of the embodiment, and FIG. 45B is an end view.

DETAILED DESCRIPTION OF THE PREFERRED EMBODIMENTS

Figure 1:
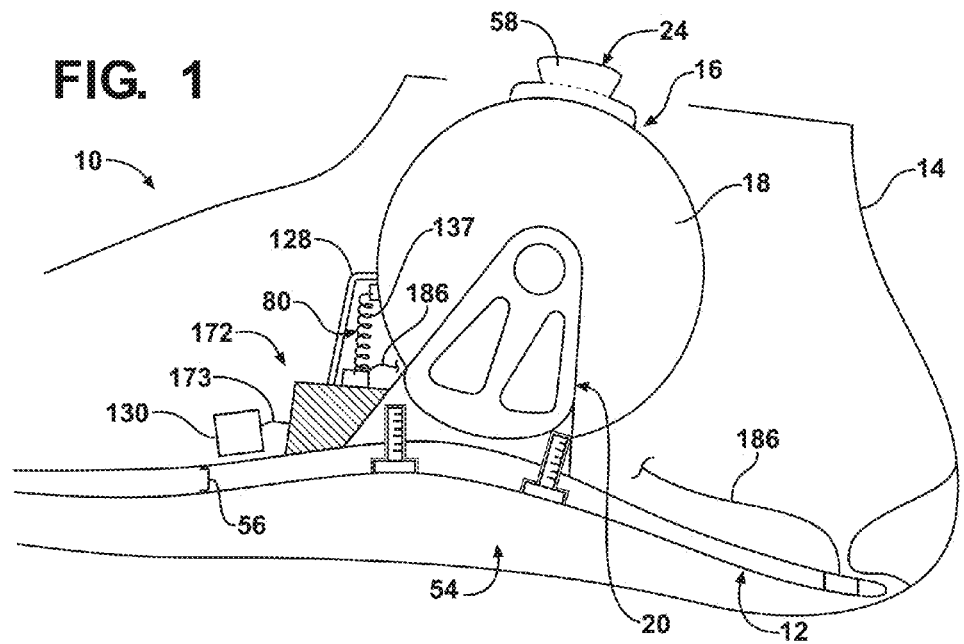
FIG. 1 is a partial cut away side view of a preferred embodiment of the invention.
Figure 2:
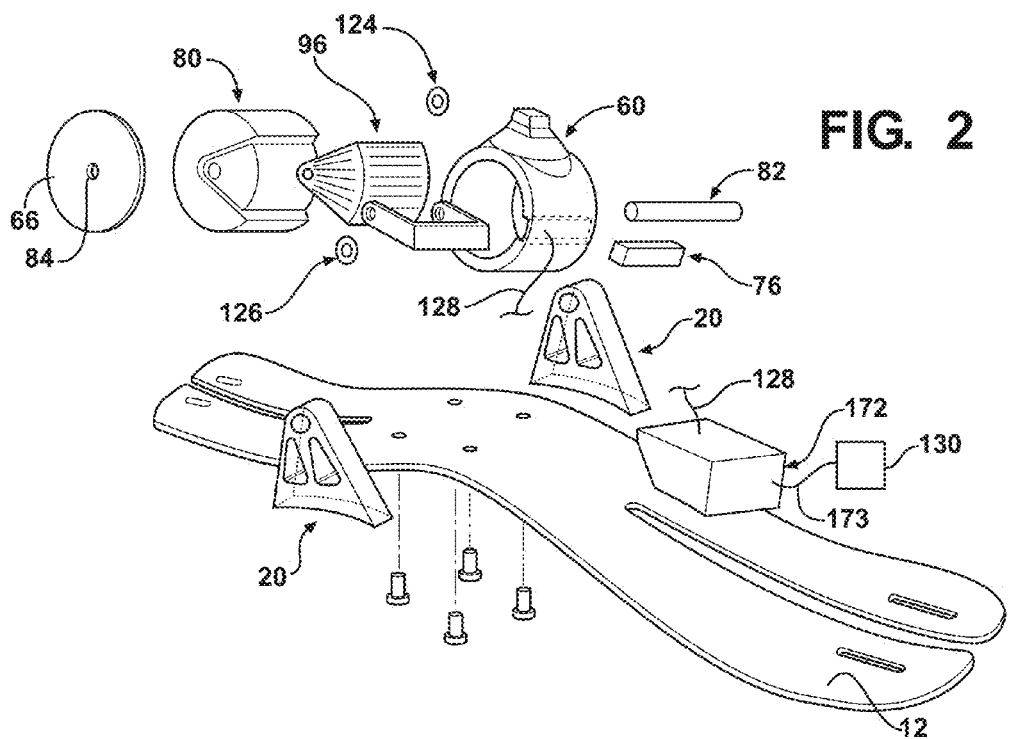
FIG. 2 is a partially exploded perspective view of a preferred general construction in accordance with the present invention.

Referring now to the drawings, wherein like reference numerals designate corresponding structure throughout the views, and referring in particular to FIGS. 1 and 2, reference numeral 10 generally refers to a new and improved prosthetic foot with ankle system, hereinafter referred to as prosthetic foot collectively, in accordance with the present invention. Invention 10 generally comprises keel 12, foot shell 14, ankle joint assembly 16, dampening means or system 18, a bracket assembly 20, sensor system 22, and attachment means 24. It should not be considered limiting what order certain components are depicted in the attached drawings. For instance, attaching either the inner or outer cylinder to the keel should be considered to be within the scope of the same invention, and does not depart from the intended disclosure. It should be understood that there are a number of orientations that various components may be placed to provide a similar benefit to the end user.

Furthermore, invention 10 is generally shown in a configuration for a right foot. It is understood that a left foot configuration is considered. It is further understood that invention 10 may be used on other joints and associated appendages such as but not limited to a knee, hip, elbow or others. The term appendages should not be considered limited to limbs such as arms and legs. Still furthermore, the term joint generally refers to rotationally attached members. Still furthermore, the invention should not be considered limiting solely to prosthetics or orthotics applications, but should include any anthropomorphic limb movement of robotic devices, as advanced prosthetics are anthropomorphic robots that work in conjunction with the human body.

Keel General Construction

Figure 3:
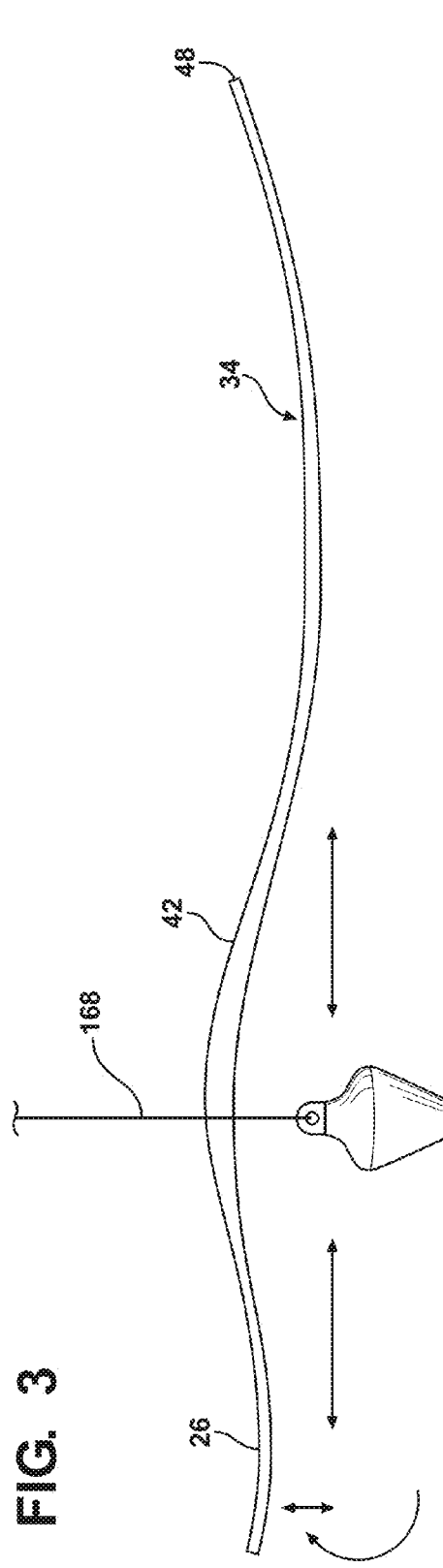
FIG. 3 is a side view of a preferred construction of a keel in accordance with the present invention also generally showing a natural weight line.
Figure 3A:
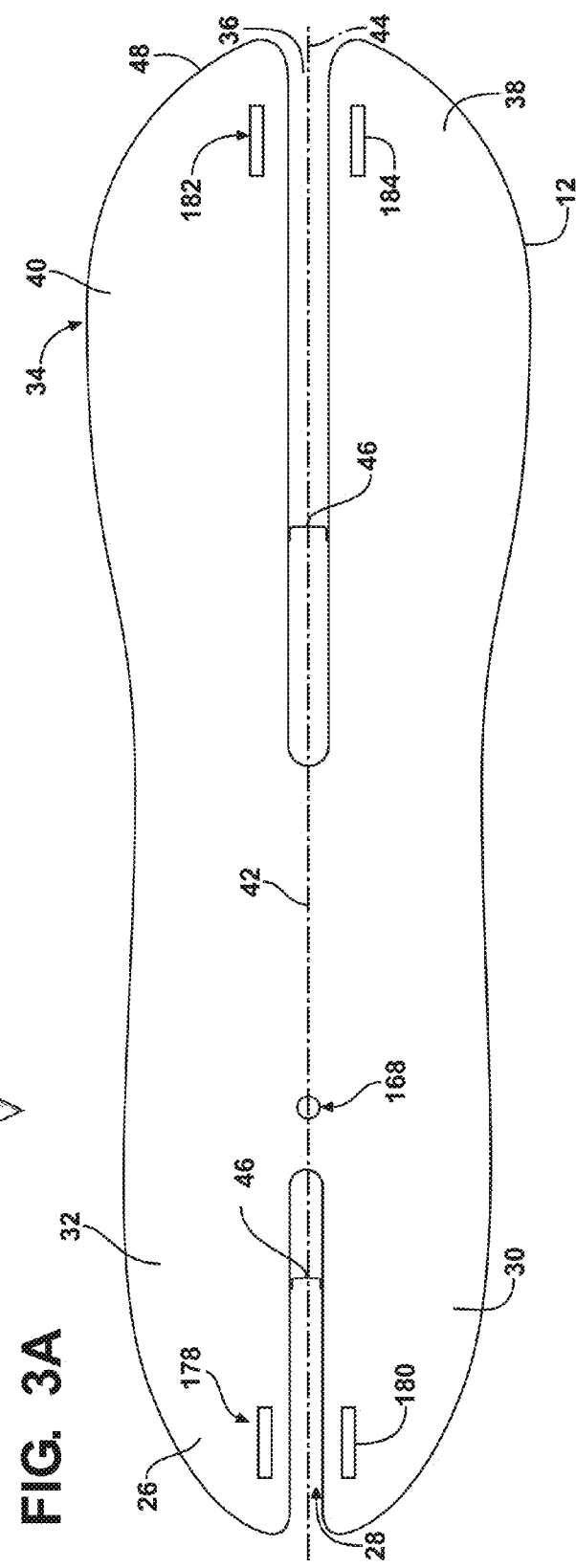
FIG. 3A is a top view of a preferred general construction of a keel and a bracket assembly in accordance with the present invention also showing the intersection of the weight line.

Referring to the drawings and in particular FIGS. 3 and 3A, a preferred construction of keel 12 is generally depicted having a heel portion 26 with posterior split 28 that generally separates the heel portion 26 into a medial segment 30 and a lateral segment 32. Furthermore, keel 12 further includes a forefront or toe portion 34 with anterior split 36 that generally separates the toe portion 34 into a medial segment 38 and lateral segment 40. The area generally between heel portion 26 and toe portion 34 is generally referred to as middle portion 42 although it is understood that the term middle should not necessarily be construed as meaning the actual middle point of keel 12.

It is further understood that a keel 12 may include the posterior split 28 and/or anterior split 36 or neither. It is also understood that anterior split 36 and posterior split 28 may run the full length of keel 12 such that keel 12 is generally of a two piece construction (not depicted). Furthermore, both anterior split 36 and posterior split 28 are generally along the midline 44 of keel 12. It is understood that general split construction of keel 12 may generally improve ambulation over uneven ground among other beneficial ambulation.

In a preferred construction, anterior split 36 and posterior split 28 should be of sufficient width 46, respectively, that a reasonable torque on keel 12 should reduce or prevent toe portion 34 medial segment 38 and lateral segment 40 and heel portion 26 medial segment 30 and lateral segment 32, respectively, from contacting or rubbing past the respective segments. Such construction may reduce or prevent a "clicking" noise during walking from said contact. It is also understood that rubber or other flexible material-based pieces (not depicted) may also be included to reduce or prevent clicking and generally located in posterior split 28 and/or anterior split 36.

The keel shape and dynamics are a vital component of the full and proper functioning of the ankle joint. While the controllable functions and intelligent control system of the ankle joint can accommodate for varied types of keels, the system as a whole is best optimized with proper keel function and biomechanically similar characteristics. In a preferred embodiment, the keel may be highly compliant or highly non-compliant, and the ankle joints function should provide a smooth roll-over through the stance phase of the gait cycle, however, to fully replicate natural biomechanical movement with the greatest efficiency and natural feel, a keel designed with similar biosymmetrical shapes, compliance areas, roll-over characteristics, and physical segment proportions. These characteristics, as described herein, are meant to characterize this general embodiment with a certain degree of particularity. These are not meant to be limiting to the disclosed characteristics only, but rather to illustrate the highly anatomical replication that this keel design exhibits. This quality, of having a more highly anatomical replication, allows for this system as a whole to function to a higher degree.

In another preferred embodiment, keel 12 may utilize a split toe design wherein the split may be offset toward one side in order to allow a cosmetic foot shell 14 with a separated big toe area in order to allow the user to wear sandals. It is understood that keel 12 may not include any split portions and generally remain with a full non-split keel 12. It is further understood that invention 10 may be adapted to utilize, retrofit, or integrate with existing known keels 12 in the prior art.

Curvature

In a preferred construction, curvature is contemplated at the end 48 of toe portion 34 and/or at end 50 of heel portion 26 such that a natural rollover during ambulation may be created and to provide keel 12 with correct positioning with respect to the ground to optimize energy return characteristics of keel 12. According to FIG. 23, the anterior and posterior ends of the foot shell may exhibit upward curvature to allow for initial heel strike and terminal stance phase smooth transition, as well as to decrease the load forces experienced between the foot shell and keel, to enhance durability. These curvature areas as well may produce enhanced roll over characteristics during ambulation.

At the anterior end of the keel, this curve up may be at or near the anatomical metatarsal head location. An additional curvature at the distal end of the toe location may assist in smoothness of roll-over at terminal stance phase of the gait cycle. Still furthermore, in certain embodiments, the general anterior section of the toe may curl upward to allow for a forefoot rocker replication. This may functionally add to shorten the relative lever arm of the forefoot during late stance, but maintain in providing necessary balance.

Figure 24:
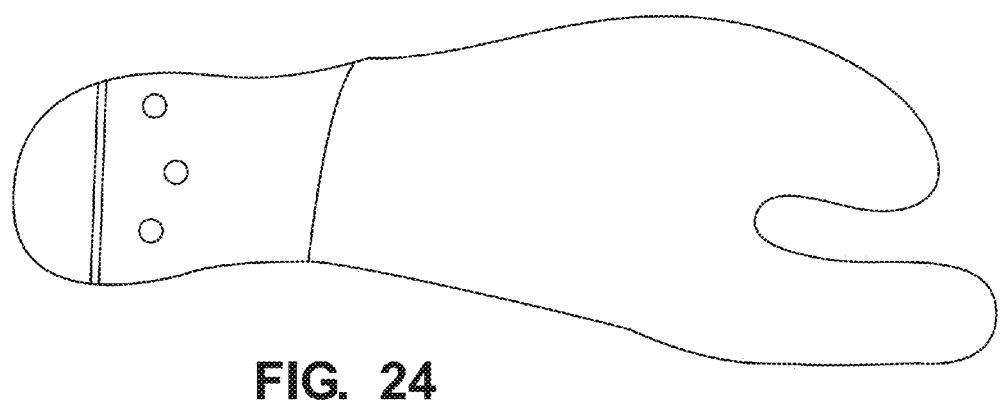
FIG. 24 is a general illustration depicting proximal view of a keel design.
Figure 25:
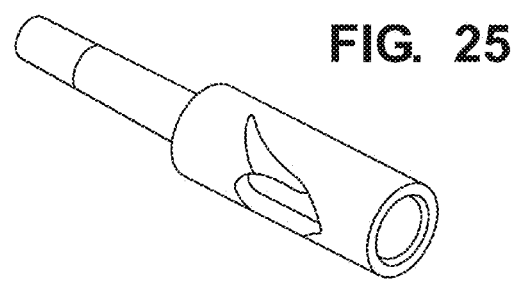
FIG. 25 is a general illustration depicting one embodiment of a valve design.

Still furthermore, as can be seen in FIG. 24, the keel may exhibit uniform or non-uniform arch(es), and variance in the transverse plane at the first metatarsal head to better simulate the arches of the plantar-surface of the anatomical foot.

It is still further contemplated that forefoot or toe portion 34 may be slightly wider than the heel portion 26 to provide additional stability for the user during later portions of stance phase of gait, as seen in FIG. 24.

It is understood that foot shell 14 should be able to accommodate a broader toe portion 34 such that a cosmetic appearance may still be achieved as well as more closely to approximate the shape of a natural human foot. It is understood that other keel 12 shapes may be considered.

Considering many shoes have a built in arch support that often causes a prosthetic foot to tilt laterally in a shoe, it is contemplated that arch 52 of keel 12 in the sagittal view will preferably be relatively high as generally depicted in the drawings. In a preferred construction, a high arch 52 will allow an appropriately tailored foot shell 14 also having a relatively high arch 54, to sit flat in shoes with high arches. Additionally, the curvature will provide smooth rollover characteristics and provide the appropriate positioning of keel 12 with respect to the ground for loading keel 12 to provide appropriate biomechanical simulation. Other heights of keel 12 arch 52 and foot shell 14 high arch 54 may be considered.

Materials

In a preferred embodiment, keel 12 may be made from but is not limited to carbon fiber and/or carbon fiber laminates, carbon laminate thermoplastics, thermoplastics, thermosets, or other. It is understood that other materials may be used that provide light weight, high strength, high energy return spring characteristics, and may generally have relative simplicity of manufacturing. It is understood that carbon fiber usage allows for some energy return. Still furthermore, carbon fiber or other likewise materials may generally reduce the overall weight, which may be important to assist in decreased energy expenditure through limiting the inertial effects on the musculature of the residual leg.

Compliance

It is understood that keel 12 may generally consist of a thickness 56 to allow sufficient bending movement during stance phase of gait (heel strike through toe off) yet will be sufficiently strong or stiff enough to prevent breaking per the user's weight and activity level. Furthermore, unlike conventional prosthetic designs, the movement and roll-over characteristics of the foot in this design are not dependent on the flexibility of the keel. Though the addition and flexibility of the keel do allow for increased energy return, slight accommodation of uneven ground, and general compliance, they are not essential for perceived smoothness of gait in this design. Through the use of the control system as described in greater detail below, this design may allow for perceived smoothness of walking through controlled ankle movement versus simply keel compliance. This may greatly benefit this design by allowing for the use of a stiffer, and therefore more durable keel design, while maintaining the perceived smooth gait sense and natural feeling ground accommodation. It is still further understood that in a preferred embodiment, keel 12 may be altered to accommodate the resistant nature of bending during walking at different speeds, with varied impacts, and for various terrains through various methods of actuation or material characteristic alteration methods.

As will be discussed in greater detail below, a preferred construction of keel 12 allows for more natural and intentional mimicking of NHL and may provide the energy return at the appropriate time during the gait cycle as with NHL, predominantly at or just before toe-off to simulate gastrocnemious contraction.

In a preferred embodiment, middle portion 42 of keel 12 may have a non-uniform thickness to allow additional strength and durability for attachment to ankle joint assembly 16. It is also contemplated that keel 12 may be flexible enough to have sufficient bending of keel 12 to compensate for NHL shock absorption mechanisms which may have been lost due to amputation such as the movement that can be found in the structure of the human foot like the ligamentous and fibrous bands, as well as with the compressibility of the meniscus pad found under the calcaneus.

It is an object of this invention as well to at least partially reproduce the natural shock absorption through controlled plantar flexion after heel strike. Instead of solely relying on keel compression, as conventional technology requires to produce shock absorption during ambulation, the controlled ankle movement allows for smoothness and shock absorption of gait. Thus, through keel compliance and/or control system accommodation, it is understood that such construction may allow for a potentially smoother gait. Additionally, increased keel 12 flexibility may allow for better uneven ground accommodation and enhanced energy return. The keel 12 thickness and compressibility may also be tailored to the user's weight and activity level to provide optimum characteristics.

Keel Shape Fabrication

In another preferred and complimentary embodiment, the keel may better mimic the natural stance phase of gait ground contact signature in shape. The keel may be fabricated from standard shapes or may be custom fabricated for each user. In a preferred embodiment, conventional or alternative scanning or impression techniques may be used to fabricate a biomimetic natural stance phase of ground contact signature in shape during static, dynamic, or static and dynamic movement. The replication of the natural ground contact signature shape is important not only for cosmetic symmetry, but also for natural roll-over characteristics and balance. In a preferred embodiment, the user's sound foot, or if not available, a donor or standard system template foot, may be scanned for plantar surface signature during standing, walking, or other activities to provide information for keel shape and/or dynamic properties. Additionally, the scan may be used to capture the foot shape for the cosmetic covering. In a preferred method, the scan may be taken of the plantar and shape signature, imported into a computer or other digital methods, it may be manipulated in software to modify the shape, thickness, cutouts, or other qualities, then may be imported to a fabrication device or method to output a physical keel. Through modifying the dimensions, thickness, rigidity, cutouts, ground contact signature from standing or moving, and bracket/damper attachment locations, amongst others, the keel may be tailored to best match the dynamic qualities of the user's gait, as well as may help to optimize the cosmetic appearance.

Attachment Location

The attachment location of the bracket or general damper assembly may be positioned in relatively near proximity to the keel's posterior section. This may allow for a slight amount of keel compliance in this area, or may allow for a fully stiff keel heel in this region. Additional rigidity may be implemented through rigid keel components or bracket systems implemented within the design. The use of a short keel lever posterior to the attachment point allows for the function of the heel rocker after heel strike of the prosthetic foot. This allows for better biomechanics replication of the natural foot post heel strike. Additionally, the keel may be integrated as one with the damper mechanism as well.

Still furthermore, it is understood that keel 12 may be integrally formed with foot shell 14. It is further understood that invention 10 may utilize an attachment means (not depicted) wherein invention 10 may be attached to existing keel 12 designs available in the art.

Shock Absorption

As in the biomechanics found in natural gait, there is a minimal compliance of the heel bony and ligamentous structure in this area. The majority of the movement and shock absorption comes about through meniscus pad compression, controlled ankle plantarflexion, and from other joints such as stance flexion of the knee, and minor hip movement, amongst others. The use of a semi-compliant foot shell, as well as engineered compliance between the foot shell and the keel, allows for replication of the compliance naturally found in the heel bony and ligamentous structures, as well as the slight shock absorption found in the meniscus pad. The meniscus pad compliance may as well be replicated through the keel compression in this area, but is more appropriately is mimicked by foot shell and foot shell/keel compliance.

Additionally, the arch of the foot may be higher on the medial side of the foot, medial longitudinal arch, than the lateral side, the lateral longitudinal arch, as can be observed as illustration in FIG. 23. This would allow for a more natural positioning in the shoe, as well as for more of an anatomical replication of the stance phase ground contact signature. Still furthermore, the keel may exhibit a slight transverse arch in shape, similar to the anatomical foot structure. These three arches are important to allow for appropriate bio-symmetrical functioning of the plantar foot bony and ligamentous structure during the stance phase of gait and for shock absorption.

Ground Contact Compliance

Furthermore, the amount of relative distance from the transverse plane centerline of the keel distally may vary for various locations on the keel. This may be in replication of the natural contouring of the anatomical foot. For instance, the area under the first metatarsal head may be slightly lower to allow for increased ground contact force during walking in this area. This as well stands to enhance a natural ground contact compliance and balance abilities. Other areas of the foot may be contoured with more or less curvature in these areas as well to provide an increased or decreased ground contact force compliance.

Still furthermore, the keel may provide one, two, three, or four splits in the anterior section to replicate the movement of the toes, and provide increased compliance in those areas. These splits may run a portion of the length of the keel.

Still furthermore, the entire keel may exude, in certain embodiments, less compliant nature than conventional prosthetic foot keels. In conventional designs, the keel is often made to be relatively flexible so as to provide ground and ambulation compliance. This is largely necessary due to there not being an ankle joint in the design, and the ankle motion is exhibited through keel compliance solely. Since the preferred embodiment exhibits a dynamic moveable ankle joint, and intelligent control thereof, the keel may be fabricated to be relatively stiff, and allow the vast majority of the compliance to come about through controlled ankle motion, and not through a highly compliant keel. This is somewhat similar to that of the anatomical ankle joint, where the bony and ligamentous structure of the foot provides very slight compliance, with more at the metatarsalphalangial joints of the toes, and the majority of the movement through ankle motion.

Rockers

During the stance phase of the gait cycle, the foot exhibits three rockers, or pivot points around which the body's mass rolls across a relatively fixed point to the ground. These three characteristically defined phases in the gait cycle are the heel rocker, ankle rocker, and forefoot rocker.

The heel rocker is exhibited from heel strike to foot flat portion of the gait cycle. As described in the previously filed application of the same technology, this is controlled through eccentric, or lengthening, contraction of the anterior tibial muscles of the lower leg. Here, the calcaneus is largely stationary compared to the ground, and the ankle joint rotates in the plantar direction, in a controlled manner. As discussed in the preceding filed patent application, this is being replicated, in a preferred embodiment, through altering the state of the damper system attached to the keel. After heel contact with the ground, the damper begins to change its state in a manner such as but not limited to closing a valve in a hydraulic or MR fluid control device, increase current to a linear actuator, or other mechanically or fluidly resistive devices. As the damper resistance increases, it slows the plantarflexion movement of the forefoot to make controlled contact with the ground. This damper practically functions as the ankle joint equivalent. From the heel strike to the foot flat portions of the gait cycle, the keel may provide slight or no compliance, but rather rely on active ankle motion to provide this movement. As stated previously, in a preferred embodiment, the center of rotation of the ankle joint may be positioned at or near the anatomical position, which allows for a short lever arm from the posterior aspect of the heel to the center of rotation, thus providing a plantarflexion moment after heel strike. The amount of lever arm may be varied to provide a greater or lesser moment depending on the desired effect. This may be modularly altered to allow for variance. The movement of the damper during this portion of typical gait cycles is providing a resistance to angular change, versus requiring powered actuation. In certain instances during some gait patterns, active powered control may be necessary, as will be discussed in further detail below.

After the heel rocker occurs, the ankle rocker begins. This occurs after foot flat portion of the gait cycle. At this stage, there is a direction change of the ankle motion from plantarflexion to dorsiflexion direction. This information may be used, in a preferred embodiment to effect the control system parameters, as will be discussed in greater detail below. From foot flat through later stages in the stance gait cycle, the ankle motion provides resistance to change in the dorsiflexion direction. The amount of this change is relative to the amount of resistance in the damper mechanism, as well as the stiffness of the keel. Regardless of the keel compliance abilities, the keel will provide a loading response during these later portions of the gait cycle, which may be unloaded in a spring-like manner at terminal stance—thus providing greater energy return, and less energy expenditure of the user.

The dorsiflexion resistance during this stage is increasing, in a preferred embodiment, to allow for optimal tibial progression, smoothness of stride, and stability. In a preferred embodiment, the medial and lateral longitudinal arches of the foot as well provide a loading response as the ankle joint becomes increasingly stiff during later portions of the stance gait. The particular shape—biomimetic in plantar surface contact signature, and contoured nature— provide increased balance, spring return, and proper rollover characteristics.

Additionally, the forefoot rocker may be further exhibited, in a preferred embodiment, through continued resistance in the final portions of the stance gait cycle through allowing minimal to no movement of the ankle joint, and relying on the roll-over characteristics of the keel. The leg (keel, ankle, and shin) rotates about the metatarsal head areas at this stage. The specific contouring, as discussed earlier, of the anterior keel, in a preferred embodiment, allows for increased compliance at or near the toe area of the keel to assist in this forefoot rocker.

Keel Length

Additionally, in a preferred embodiment, the curvature of the anterior portion of the keel may be such that it may curve upward toward the end to better mimic the natural toe movement. The toe area of the keel to footshell connection, in a preferred embodiment, may be a relatively loose positioning whereas to allow the anterior keel to migrate up and down in the anterior portions of the keel so that a more cosmetic toe motion may be realized, without having to lessen the stiffness, and hence durability, of the anterior keel section. In an alternative embodiment, the anterior keel may be affixedly or otherwise connected at the anterior portion to the footshell. Additionally, the anterior end of the keel may be shortened compared to conventional keel lengths to allow for the foot shell to bend in a realistic manner at the toes. This is only possible due to the ankle joint allowing for varied resistance during the gait cycle. Because the ankle provides varied resistance, and hence varied angle for that resistance to occur at, the keel with respect to the shin may be increasingly stiffened at a slightly more plantarflexed angle compared to conventional systems, thereby allowing for similar anterior support during the latter portions of the gait cycle through maintaining a shortened keel length.

Still furthermore, alternative keel shapes, designs, contourings, and the like may be implemented within this design to allow for microprocessor, computer, or other control of an ankle joint to be realized in conjunction with a foot mechanism.

Still furthermore, the keel 12 may, in a preferred embodiment, may extend to, or just past, the forefoot rocker location of the foot. Past the forefoot rocker area, a more flexible means may be utilized, such as the foot shell, cosmesis, foam, or any other flexible type of material to fill in the forefoot and toe areas. During the late portion of terminal stance (at end of single limb support), the body weight rolls across the forefoot rocker of the anatomical foot—near the metatarsophalangeal joint. During this portion of terminal stance, where the ankle torque amount is the greatest and this is where the greatest amount of pressure on the plantar surface of the foot is observed during stance phase of the gait cycle. Anterior to this area, the toes provide balance, and minimal weight support. Therefore, by providing the keel to extend to just at or past the forefoot rocker area and providing a flexible anterior section, the biomechanics of the anatomical foot may be further replicated and enhanced. Furthermore, the torque exhibited at the ankle joint will be less than what is found in conventional prosthetic feet, due to the terminal single limb stance pressure not extending as anteriorly. This will benefit this design by allowing for less torque to be found at the ankle joint, therefore increasing durability. With conventional prosthetics feet, the keel extends to the anterior most aspect of the foot, while providing a spring return through terminal stance from the keel bending. This causes there to be an excessive amount of torque at the ankle location, and on the keel. Because this innovation allows for a dynamic nature to the ankle joint—altering the angle of the ankle and angular resistance in real time—the proper orientation of the ankle joint corresponding to the transversed terrain can be optimized, and there is not the need for the full length keel extension to the anterior most portion of the foot.

With conventional prosthetic feet, the angle of the ankle joint is not altered during the stance phase of the gait cycle; therefore, the support of the body is dependent on the keel extending out to the anterior portion of the keel. Rather, what is found in the anatomical foot, is proper resistance at the time that the forefoot rocker is being utilized, along with a proper ankle of the shin with respect to the foot (ankle angle), resulting in the ability to appropriately support the body over the forefoot section without having to have a keel that extends to the anterior most portion of the foot.

Still furthermore, the use of altering stiffnesses in the toe section that extends out past the keel may be utilized to further enhance the support at this area. This may come about through state changing materials, actuators of various types, or other means to provide an altering to the toe stiffness or resistance to angular change, and hence, optimize balance. These may as well be utilized in conjunction with sensors, electronics, microprocessor, or other electronic means of providing intelligent control of the toes of the prosthetic device to optimize energy return, and balance, among other qualities.

Foot Shell

In a preferred construction, foot shell 14 may be generally anatomically correct and may further include a sufficiently high arch 54. This may include a medial longitudinal arch, lateral longitudinal arch, and/or transverse arch, or any combination thereof. The keel 12 foot may lock, snap, or form into the foot shell 14. It is understood that a SPECTRA, or functionally similar, sock may be used over foot keel 12 to reduce or prevent squeaking noises arising from the keel rubbing against the foot shell 14. The same internal design of this said foot could be used with either a left or right foot shell 14 for simplicity in manufacturing.

In a preferred embodiment, it may be desirable to provide a foot shell 14 that is generally thin as to not limit the motion of the foot design through stiffness. It is contemplated that a thinner foot shell 14 allows for full keel 12 dynamics although the invention 10 should not necessarily be limited to such.

In a preferred construction, keel 12 is removably attached to foot shell 14. It is contemplated that conventional means known in the art may be utilized. In a preferred construction, keel 12 may generally attach to foot shell 14 by having a small protrusion extending out within the inside of the foot shell 14 in which keel 12 snaps in place underneath.

In an alternative embodiment, the keel may be integrally encapsulated within a cosmetically molded foot shell, which may be customized to the individual user. This method of fabrication may be similar to silicon restoration, or other complimentary procedures to capture a biomimetic foot shape. Still furthermore, in a preferred embodiment, the shape of the cosmetic covering may be replicated from the end user's sound limb via scanning, impression, or similar shape and/or color matching techniques used in the field. Additionally, there may be a multi-durometer footshell utilized, in an alternative embodiment, which may allow for greater plantar-surface durability due to that area being a high-stress area of the foot. Other areas may as well exhibit higher durometers, such as but not limited to, the posterior heel, anterior, toes, top surface, or sides of the foot. The characteristics of a scanned image may be modified through a user interface system on a computer or other electronics device, much like how the keel may be modified through a user interface system. Various characteristics of shape, coloring, durometer, size, weight, keel attachment location, and other characteristics defining the final cosmetic product may be altered in the user interface and used to ultimately define the fabrication procedure of the product. This image then may utilize a rapid prototyping method to form either a cosmetic cover or the mold to make the cover.

Attachment Means

Invention 10 generally includes attachment means 24 to a user's lower extremity (not depicted). Attachment means 24 may be but is not limited to a male pyramid 58. It is understood that other conventional attachment means 24 known in the art may be used such as but not limited to threaded screws that matingly engage removable and non-removable bolts, removable pins, and so forth may be utilized. Furthermore, it is understood that male pyramid 58 may be of a female configuration and so forth.

Ankle Joint Assembly Inner and Outer Cylinder Relation

Referring once again to the drawings and in particular FIGS. 4, 4A, 4B, and 4C, ankle joint or joint assembly 16 generally comprises a housing or outer cylinder 60 that is generally connected to attachment means 24. In a preferred construction, outer cylinder 60 is generally in a fixed position or non-rotational position relative to lower extremity and attachment means 24. Outer cylinder 60 generally includes an interior cavity 62 and a center axis 64, which may or may not be located in the geometric center of the unit. Furthermore, outer cylinder 60 may or may not include first side cover 66, second side cover 68, and a range of rotation restrictor mechanism 70. In a preferred construction inner cylinder 80 generally attaches to keel 12 in a fixed or non-rotational manner such as but not limited to bracket assembly 20 which will be discussed in greater detail below. It should be understood that alternatively, outer cylinder may be in a fixed position relative to keel. Conversely, inner cylinder would then be in a fixed position relative to attachment means and lower extremity. In the art of prosthetics, it should be understood that having the outer cylinder for instance being in a fixed position to the lower extremity or to the keel is one and the same and should not be considered limiting in any way. Each illustration is equivalent in nature to the scope of the invention.

Still furthermore, the prosthetic, orthotic, or robotic system is shown with an energy transfer mechanism with variable resistance that can variably restrict fluid flow through an orifice.

It is further contemplated that range of rotation restrictor bar 70 may include cavity 72, which may generally be located along perimeter 74 of outer cylinder 60 such that electromagnet 76, which will be discussed in greater detail below, may also generally be installed in a relatively fixed position relative to lower extremity and attachment means 24. In a preferred construction, outer cylinder 60 may be generally constructed of non-magnetic non-conductive material as will be described in greater detail below. In a preferred embodiment, electromagnet 76 is generally disposed in cavity 72, which may also be generally disposed in range of rotation restrictor bar 70.

Once again referring to the drawings and in particular FIGS. 5, 5A, 5B, 5C, and 5D, generally disposed in outer cylinder 60 interior cavity 62 is inner cylinder 80. It is understood that inner cylinder 80 generally rotates around outer cylinder 60 axis 64, though axis may not be located at geometric center of unit. Furthermore, the term cylinder should not be considered limiting, and is used for simplicity of explanation to describe any arc-like movement path of the members, and may include non-uniform or uniform arc paths.

It is further understood that inner cylinder and outer cylinder rotate in a relative motion with one another, and may or may not be in contact with one another.

Shaft

Figure 6:
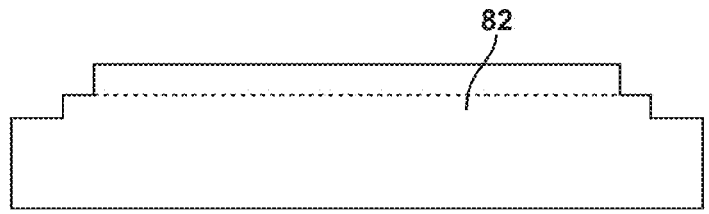
FIG. 6 is a side view of a preferred general construction of a shaft in accordance with the present invention.
Figure 6A:
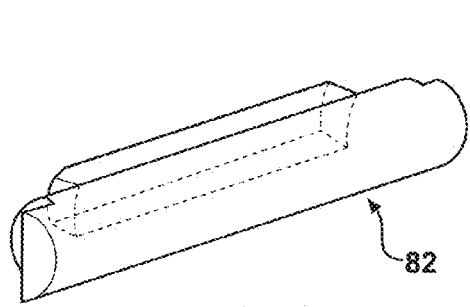
FIG. 6A is a perspective view of a preferred general construction of a shaft in accordance with the present invention.
Figure 6B:
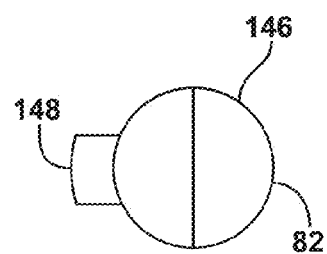
FIG. 6B is another side view or end view of a preferred general construction of a shaft in accordance with the present invention.

Referring to FIGS. 6, 6A, and 6B, in a preferred construction, shaft 82 generally is positioned and aligned along the interior cavity 62 of outer cylinder 60 along axis or rotation 64 whereby inner cylinder 80 is generally attached to shaft 82. Whether shaft is at center of geometric unit or offset does not depart from the scope of the invention, as the axis defines location of rotation of inner cylinder with respect to outer cylinder. Furthermore, shaft 82 generally aligns inner cylinder 80 and outer cylinder 60. Shaft 82 is generally axially aligned and connected by outer cylinder 60 first side cover 66 aperture 84 and second side cover 68 aperture 86. Shaft 82 may be made from non-magnetic material or magnetic material. Furthermore, at least one side cover may be non-removably connected to outer cylinder.

Center Axis and Inner and Outer Cylinder Definition

The term "center axis" should not be considered limiting to define the geometric center, while the term axis always describes the rotational center of movement. Still furthermore, the center axis of the system may reside outside any structural members. Still furthermore, the axis may generally describe the center of angular movement of the invention as a whole, and therefore may include any fluid filled, or other, assembly that allows for altering a proximal and distal, inner and outer, or other orientation means of controlling dorsiflexion and plantarflexion. For instance, using a keel member with a more proximal strut or structural member that rotate in relation to each other about a fixed or moving rotational point, further constitutes two cylinders, or similar, rotating with respect to each other. While the described invention may illustrate structural members in many of the figures, they are used for explanatory purposes only, and should not be considered limiting in any way. The relative rotary movement of these two members may constitute "inner and outer" cylinders, as the movement pathway of each member creates a cylindrical or similar shape when moved through its arc. FIG. 15 further depicts this equivalency. Still furthermore, FIGS. 45A and 45B demonstrate the relationship between the inner and outer cylinder, axis of rotation, and other characteristics for the equivalency between various depictions of the two chamber damper mechanism.

Shaft may furthermore run along axis of both inner and outer cylinder, however, axis of the inner and outer cylinders may not run in the geometric center of the damper unit, nor may the axis of the inner cylinder be aligned with the axis of the outer cylinder. The inner and/or outer cylinders have an arc segment of a larger circle whereas a portion of the larger circle is not encompassed in the geometric damper area. Additionally, the arc segment of inner and/or outer cylinder may be of a CAM shape.

As discussed above, outer cylinder 60 may remain in a relatively fixed position relative to lower extremity of user and generally secures shaft 82 such that shaft 82 may rotate along axis 64. Inner cylinder 80 is generally attached to shaft 82 and rotates relative to user lower extremity, or vice versa. In a preferred embodiment, shaft 82 is in a relatively fixed attachment to inner cylinder 80. It is understood that other conventional rotational means may be provided wherein outer cylinder 60 is in a relatively fixed position relative to user lower extremity and inner cylinder 80 is generally free to rotate respective to user lower extremity.

Range Of Motion

Inner cylinder 80 is generally constructed such that rotation along center axis 64 is limited. In a preferred embodiment, inner cylinder 80 includes top stop 88 (FIG. 7) which contacts outer cylinder 60 range of rotation restrictor bar 70. Furthermore, inner cylinder 80 may include bottom stop 90 (FIG. 7) which contacts outer cylinder 60 range of rotation restrictor bar 70.

It is understood that the range of motion limiting mechanism may be depicted in numerous ways, all of which are considered one and the same as the desires range of motion of the device is limited.

Figure 7:
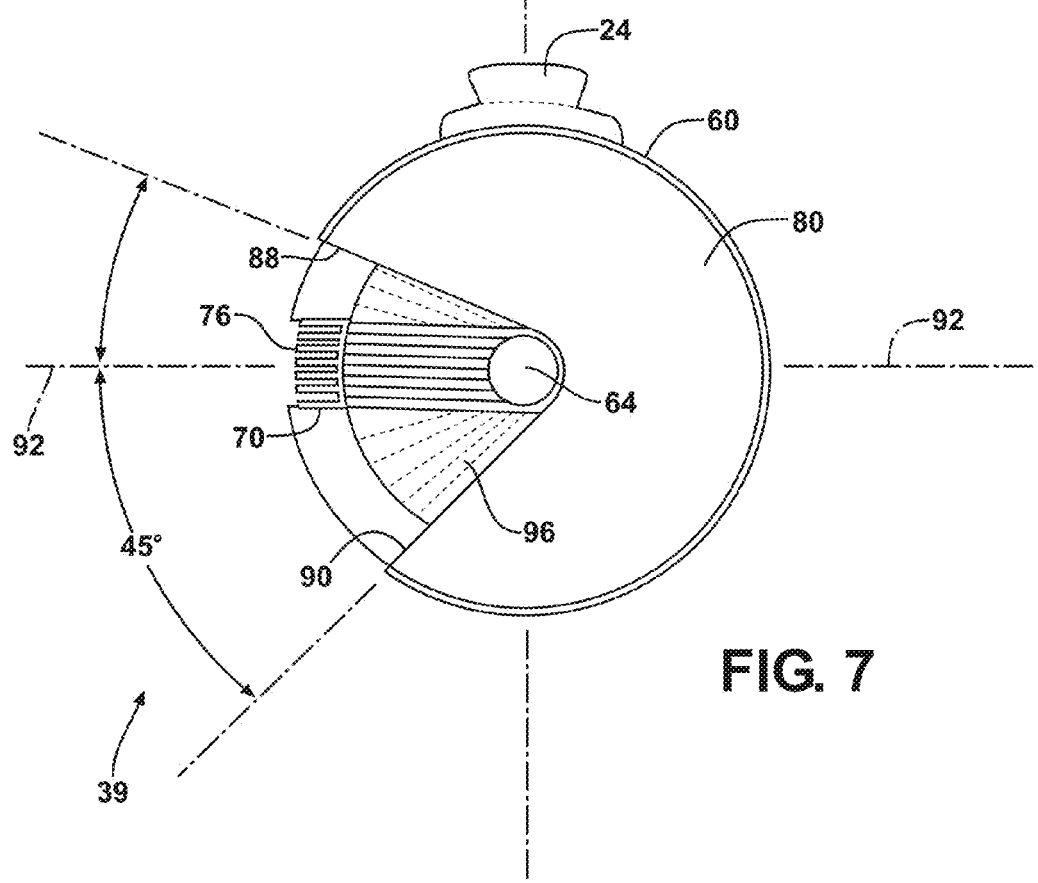
FIG. 7 is a partial cross-sectional side view of a preferred general construction of a joint assembly in accordance with the present invention and also generally depicting the horizontal.

Referring generally to FIG. 7, it is understood that the human ankle has a general range of rotation of about 15 degrees up (from horizontal 92) and a general range of rotation of about 45 degrees down (from horizontal 92). In a preferred embodiment, inner cylinder 80 is generally restricted from rotating up past 15 degrees by top stop 88 contacting outer cylinder 60 range of rotation restrictor bar 70. Furthermore, inner cylinder 80 is generally restricted from rotating down past 45 degrees by bottom stop 90 contacting outer cylinder 60 range of rotation restrictor bar 70. It is understood that the general range of rotation may be increased or decreased and the above example should not be considered limiting. It is contemplated that greater range of motion or rotation may be desired for certain activities requiring more general flexibility and, likewise, more restricted range of motion or rotation for other activities where less flexibility may be desired.

Cavity

The inner cylinder 80 may be made hollow or with lightweight core to decrease weight. It is understood that inner cylinder 80 may be weighted, filled with a deformable semi-solid material, fluid filled, or other such means where the center of gravity (not depicted) of the inner cylinder 80 may move relative to the ankle joint assembly 16.

It is further contemplated that inner cylinder 80 may include a cavity 78 for locating elements of the invention 10 and for possibly providing a water tight compartment for electronics, sensors, fluid control devices and methods, or power source 130 used in association with invention 10 which are discussed in more detail below.

It is contemplated that any combination of the above described design and orientation may be utilized without departing from the scope and function of the device. These above described orientations of the various sub-components should not be considered limiting in any way, as numerous illustration are possible using inner and outer moving components. It is understood for instance that the outer cylinder may be connected to the keel, and rotate about the center shaft, which may be connected to the lower extremity. In this preferred construction, the outer cylinder 60 is generally in a fixed position or non-rotational position relative to the keel.

Outer cylinder 60 stays in a relatively fixed position relative to keel and generally secures shaft 82 such that shaft 82 may rotate along center axis 64. Inner cylinder 80 is generally attached to shaft 82 and rotates relative to keel. In a preferred embodiment, shaft 82 is in a relatively fixed attachment to inner cylinder 80. It is understood that other conventional rotational means may be provided wherein outer cylinder 60 is in a relatively fixed position relative to keel and inner cylinder 80 is generally free to rotate respective to keel. Inner cylinder may then be attached to lower extremity via bracket or other attachment systems.

Additionally, in a preferred embodiment, the center of rotation of the ankle joint assembly should fall at or near the anatomical center of rotation. It is understood that from user to user, the anatomical center of ankle rotation may fall at slightly different locations with respect to the ground, proportions of leg segments, or other comparative methods. It is therefore understood that the anatomical center of rotation may not be exactly met through using this device, but that in general the ankle joint falls in the anatomical center of rotation intended area whereas a natural looking ankle motion is apparent.

Additionally, it is understood that design may be fabricated using various types of materials, including metals, allows, thermoform plastics, thermoset plastics, nanotechnology, carbon nanotubes, or any other material known in the art.

Dampening System

Figure 8:
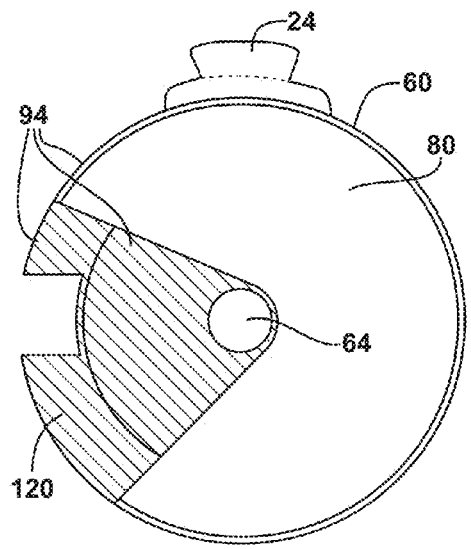
FIG. 8 is a partial cross-sectional side view of a preferred general construction of a joint assembly in accordance with the present invention and also generally depicting the MR fluid.
Figure 8A:
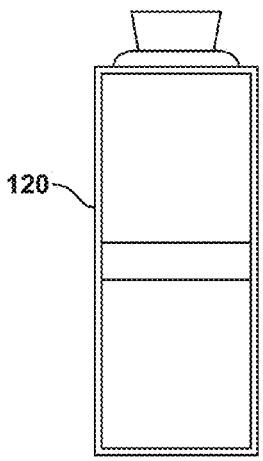
FIG. 8A is another partial cross-sectional side view of a preferred general construction of a joint assembly in accordance with the present invention.

Once again referring to the drawings and in particular FIGS. 8 and 8A, dampening means or system 18, generally refers to a means for controlling keel 12 rotation in association with and respective to the user. Dampening system 18 may generally include electronic control, mechanical function, fluid dynamics, and combinations thereof. It is understood that invention 10 contemplates numerous means such as hydraulic, magnetic, mechanical or other constructions wherein the dampening, general control, or characteristics of the rotation of the joint assembly 16 is achieved.

Magnetorheological Fluid General

In a preferred construction, magnetorheological or MR fluid or other fluid types 94 is generally used for dampening the rotation of inner cylinder 80 around the axis 64 of outer cylinder 60 whereby the fluid 94 state of liquidity or viscosity is relatively controlled by selectively charging the MR fluid 94 via use of a permanent magnet or electromagnet or valving system 76. By example, where no or little dampening is desired, the MR fluid 94 is not charged and generally stays in a relatively liquid state thereby creating little to no impediment for inner cylinder 80 from relatively freely rotating around center axis 64 of outer cylinder 60. When dampening is desired, the MR fluid 94 is selectively charged to harden or somewhat solidify the MR fluid 94 so that generally a viscous clutch, brake or impediment is created whereby the rotation of inner cylinder 80 around center axis 64 of outer cylinder 60 is slowed and/or halted.

It is also contemplated that MR fluid 94 may further act as a general lubricant for ankle joint assembly 16 outer cylinder 60 and inner cylinder 80. It is still further contemplated that invention 10 may be utilized with hydraulic or other adjustable damper means to control plantarflexion and dorsiflexion. It is understood that the current invention 10 may incorporate other means such as generally fluid type dampening other than MR fluid 94. Likewise it is understood that invention 10 may be carried out with no per se fluid and relay on magnetic and/or mechanical dampening.

Surfaces and Construction of Magnetic Pathway

In a preferred embodiment, inner cylinder 80 further includes a conductive surface 96, which may integrally be part of inner cylinder 80 or formed in as cover 98. Conductive surface 96 should generally be made from a material that is capable of carrying or conducting an electric or magnetic charge and the term conductive should not necessarily be considered to be limiting. Conductive surface 96 may be made from metal, plastic with metal fibers, or other generally conductive materials or variations thereof. Conductive surface 96 may include a first side 100 and a second side 102 such that a generally larger surface area is contemplated for interaction with MR fluid 94.

Furthermore, conductive surface 96 may be generally near or in communication with shaft 82. Conductive surface 96 may include apertures 104 and 106 for generally attaching with shaft 82. It is contemplated that shaft 82 may be of a conductive, metallic, or the like material whereby MR fluid 94 would also interact with shaft 82 in possible relative conjunction with conductive surface 96. Still furthermore, conductive surface 96 may have serrations 108, ridges or the like.

Figure 4:
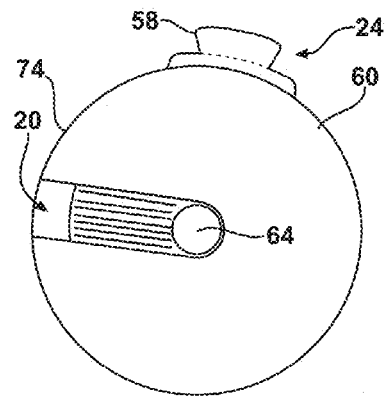
FIG. 4 is a side view of a preferred general construction of a joint assembly in accordance with the present invention.
Figure 4A:
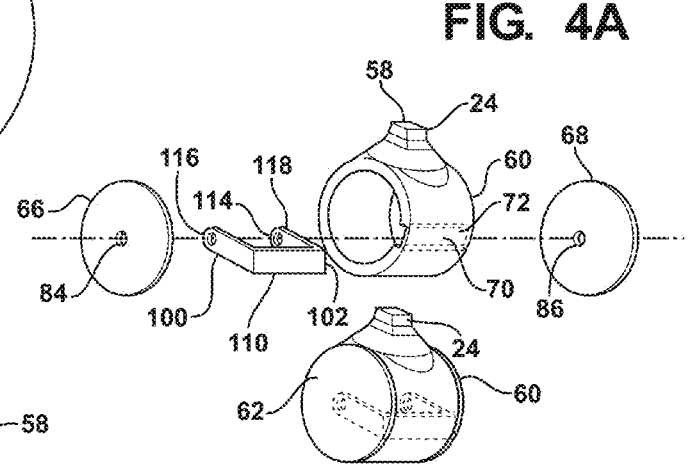
FIG. 4A is a partially exploded perspective view of a preferred general construction of an outer cylinder in accordance with the present invention.
Figure 4B:
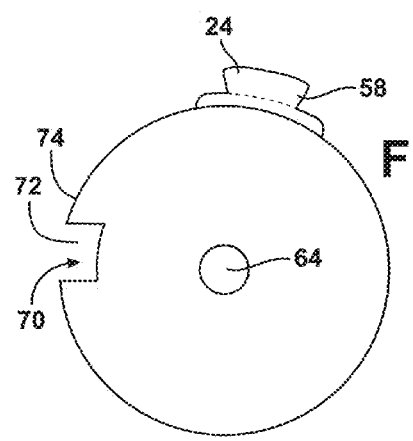
FIG. 4B is a side view of a preferred general construction of an outer cylinder in accordance with the present invention.
Figure 4C:
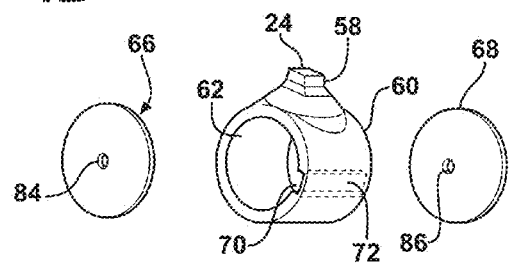
FIG. 4C is a partially exploded perspective view of a preferred general construction of an outer cylinder in accordance with the present invention.
Figure 4D:
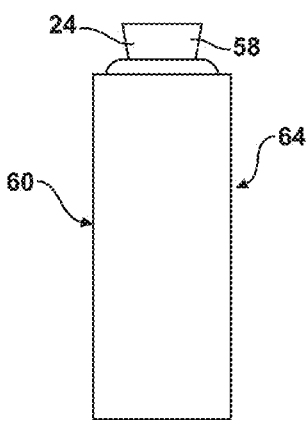
FIG. 4D is another side view of a preferred general construction of an outer cylinder in accordance with the present invention.

As discussed above, outer cylinder 60 is generally formed from non-magnetic or conductive material. In a preferred construction, outer cylinder 60 includes conductive surface or strip 110, which may be integrally formed with outer cylinder 60 or as separate element 112 as generally depicted. Furthermore, conductive surface or strip 110 may have serrations 114, ridges or the like (FIG. 4A). In general, outer cylinder 60 strip 110 is aligned with inner cylinder 80 conductive surface 96. In a preferred construction, strip 110 may further include a first side 117 and a second side 119, which may generally interact with inner cylinder 80 conductive surface 96 first side 100 and second side 102, respectively. Still furthermore, strip 110 may generally connect or be in contact with shaft 82. Conductive strip 110 may include apertures 116 and 118 for generally attaching with shaft 82.

The inner cylinder 80 conductive surface 96 and outer cylinder 60 conductive strip 110 may include serrations 114, ridges or the like in a generally radial direction from center axis 64 in order to increase or help MR fluid 94 lock down in the presence of an electric or magnetic field and thereby increases direct shear mode response. It is further contemplated that such construction would additionally increase the surface area for MR fluid 94 communications and interaction.

It is contemplated that void, space, or cavity 120 is generally created between outer cylinder 60 and inner cylinder 80 and generally filled with MR fluid 94. In a preferred embodiment, inner cylinder 80 is generally disposed in outer cylinder 60 such that a general close proximity may be achieved to limit the amount of MR fluid 94 needed with possible exception to areas specifically where the given distance would be optimized for fluid dynamic characteristics. Furthermore, MR fluid 94 may act as a general lubricant to decrease friction between the inner cylinder 80 and outer cylinder 60 during rotation. It is also contemplated that having the inner cylinder 80 and outer cylinder 60 in a relative close proximity would increase or benefit the structural lateral torque stability of the dampening system 18.

It is still also contemplated that shaft 82 may be made of conductive or magnetic properties in order to assist or decrease or prevent possible leakage of the MR fluid 94. By example, such construction may generally make the MR fluid 94 generally more viscous and not as likely to leak through holes or potential holes in seals.

Figure 9:
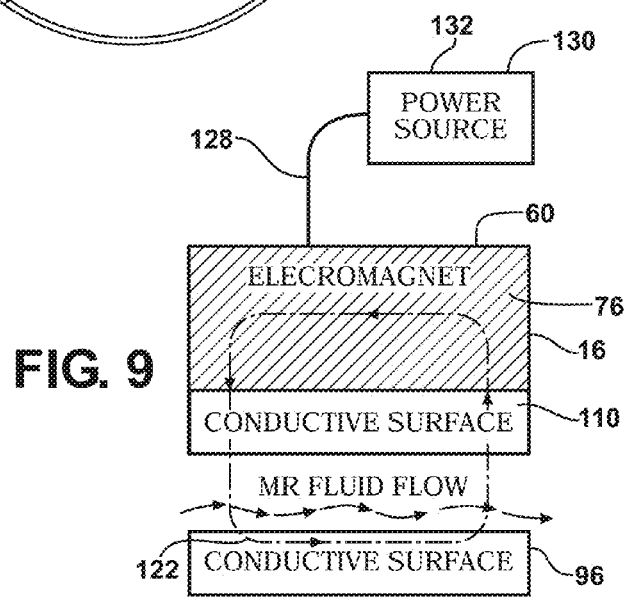
FIG. 9 is a partial cross-sectional top view of a preferred general construction of a joint assembly conductive circuit in accordance with the present invention.

Now referring to FIG. 9, in a preferred construction, electromagnet 76 is generally in communication or contact with outer cylinder 60 conductive strip 110, which is in communication with or contact with MR fluid 94, which in turn is in communication or contact with conductive surface 96 of inner cylinder 80, thereby forming electric or magnetic flux circuit 122. This may be illustrated in any number of ways to form a magnetic pathway.

Spacers 124 and 126 made from but not limited to nylon may also be utilized in a preferred construction and generally be placed between inner cylinder 80 and conductive strip 110 to decrease or prevent completion of circuit 122 aside from charging the MR fluid 94 in completion of circuit 122.

Power Source

Power source 130 is generally in contact or communication with electromagnet 76 via wires 128. It is contemplated that the dampening system 18 may have a low draw of energy consumption, and thus a small battery 132 may be utilized. In a preferred construction, battery 132 would preferably be lithium ion in nature but is not limited to such. Power source 130 can be placed anywhere on the prosthesis for ease of replacement and may include an attachment port (not depicted) for recharging. Additionally, for optimizing the weight distribution, power source 130 can be placed externally such as on the socket or pylon. It is also contemplated that the power source 130 could selectively be placed higher, keeping a higher center of gravity for minimizing inertial forces during running. As discussed above, power source 130 may generally be located in cavity 78 of inner cylinder 80 or shaft or pylon. Additionally, battery may be charged using plug in style, inductive style, or other rechargeable battery methods.

Lock Out Safety Feature

Furthermore, electromagnet 76 may also incorporate a safety features to allow a manual lock such as but not limited to a permanent magnet for the event of power loss. It is contemplated that as a potential safety backup, wherein by example a power source 130 level were to decrease to a certain level, a reverse polarity may be created to cause the permanent magnet to slide into position to lock joint assembly 16 or dampening system 18 or means may also be used to de-gouse the MR fluid. By example, a permanent magnet may be slid into a desired position (manually or electronically) to create a positive lock at a fixed angle to allow the user to ambulate with some or all of the motion coming from the keel 12 compression such as may be found in prior art standard prosthetic feet. Once recharging or power source 130 returns to a relative normal condition, the polarity would again reverse back to its normal state, causing the permanent magnet to move out of position, and invention 10 may then operate via the electromagnet 76. As power levels become low, an indicator, such as audible or vibratory alert may be used. Still furthermore, manual of electronic means of largely locking out the ankle joint may be implemented in various methods and forms with any type of mechanical, fluidly, or otherwise controlled damper mechanism.

Fluid Restriction System

It is further contemplated that joint assembly 16 and dampening system 18 may include a magnetorheological or other dampening which may operate by either or both direct shear and pressure driven mode to generally increase the resistance ability of the joint assembly 16. As stated above, dampening system 18 may of numerous construction contemplated within the scope of invention 10.

Figure 9A:
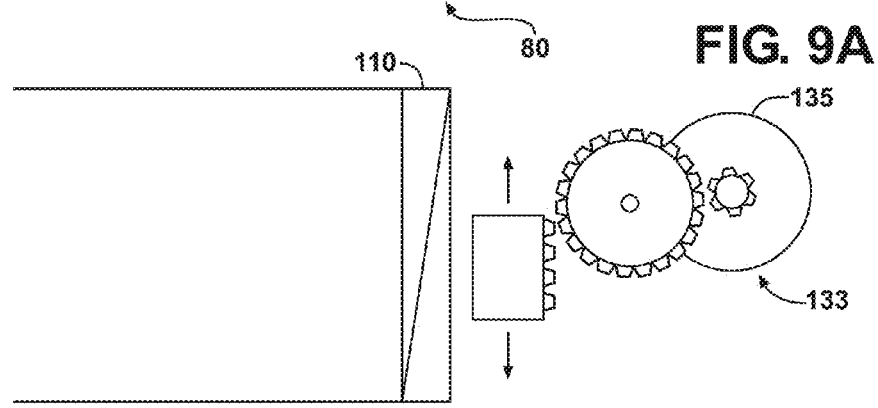
FIG. 9A is a general illustration of a preferred embodiment in accordance with the present invention.

Referring to the drawings and FIG. 9A in particular, it is still further contemplated that a mechanical based servo or permanent magnet system 133 may be used in conjunction with or as opposed to electromagnet 76. It is further contemplated that tapered magnetic and nonmagnetic pieces which are joined together with which the permanent magnet slides against, valve movement via a servo or motor, or other methods in order to vary the magnetic field interacting with conductive piece number 110, or adjust fluid flow characteristics in general. In a preferred construction, fluid restriction system 133 may include a small servo or motor mechanism 135, such as but not limited to one utilizing gears, to slide back and forth.

In general, the means for controlling fluid flow cumulatively may be considered one and the same, and generally can collectively be referred to as fluid restriction system.

Additionally, mechanical based servo/permanent magnet system 133 may include a hydraulic adjustable valve (not depicted) to control the amount of fluid passing between outer cylinder 60 and inner cylinder 80. The valve may be controlled as well by a small servo or motor mechanism or other actuation methods. It is understood that all known or novel actuation methods would provide equivalent function and purpose and method of actuation of fluid restriction device should not be considered limiting in any way. It is contemplated that electro-mechanical based servo system may require less energy consumption and may therefore be beneficial in certain applications.

Dorsiflexion Assist

Dampening system 18 may also generally include spring system, dorsiflexion means or dorsiflexion spring system 137. It is contemplated that dorsiflexion spring system 137 may cause the ankle joint assembly 16 to dorsiflex during swing phase of gait. Dorsiflexion spring system 137 may comprise a spring of conventional nature, hydraulic piston, combinations of both or other conventional spring biased devices or other actuation strategies known in the art including but not limited to active and passive power actuations strategies. The term dorsiflexion spring should not be considered limiting, but rather, should generally describe means of assisting to raise the foot into dorsiflexion through one of several means during the initiation of the swing phase of gait. Dorsiflexion spring system 137 may be attached or located anteriorly or posteriorly to the dampening system 18 or ankle joint assembly 16 (compression or extension spring, depending on the location for shortening or lengthening, respectively). Still furthermore, in a preferred embodiment, active powered control of the dorsiflexion may occur through hydraulic or other fluidly controlled means, mechanical motorized, linear actuator, or other means. In general, the use of dorsiflexion in a computer or electronically controlled ankle joint can be characterized by one of several means. As will be discussed below, the method and approach in general of initiating dorsiflexion during the appropriate moment in the gait cycle is an important element of the disclosed invention. Utilizing dorsiflexion in a passive (spring-like system) or active (powered hydraulic, electrical, or other) manner, as described in this invention, and the preceding patent, are unique elements of this disclosure. After the toe-off portion of the gait cycle, providing active dorsiflexion enables the user to gain a decreased change and occurrence of stubbing the toe or stumbling during the swing phase of gait. Further details of the method of initiating swing phase dorsiflexion will be discussed below.

The spring load resistance may be changed through adjusting the spring drive length, changing to a lighter or heavier spring, or adjusting spring placement. Additionally, it may be altered through electronic means such as but not limited to user interface systems, allowing the practitioner in the field, or patient to adjust the spring characteristics, dynamic movement characteristics including but not limited to angular change, timing, angular velocity, angular acceleration, force, and range of motion, or through embedded control using sensors, microprocessor, or the like. Still furthermore, the dorsiflexion mechanism may be initiated via sensor, mechanical, or software based systems, as will be discussed in further detail below. Still furthermore, information such as angular change, angular velocity, force during the gait cycle, ground contact information, or other biomechanics sensor related information may be used to initiate and control the rate of angular change over time, as well as the amount of angular change of dorsiflexion during the swing phase of gait.

Additionally, the dorsiflexion spring may only come into effect upon completion of specific parameters, such as but not limited to after toe off has occurred. For instance, if the user is going to sit down and prop their feet up, they may purposely not initiate a true gait cycle and hence not perform a true toe off, and therefore not allow the prosthesis to go into dorsiflexion so that it does not provide an uncosmetic effect during their activity. It should be understood that the above example is used for illustrative purposes only and that there are numerous defining methods of preventing the initiation of toe off, each of which may be customized to the particular user.

Compliant Hydraulic Mechanical System

Alternatively, the control of the ankle joint may come about through altering the state of the keel to shank sections through compliant fluid dynamic means. As opposed to conventional hydraulic or other fluidly actuated means, the use of compliant hydraulics allows for the actual housing compartments for the fluid be compliant in nature, thereby allowing for natural give to occur while managing forces and movement.

In a preferred embodiment, one or more fluid filled damping systems may be utilized to prevent motion in the plantar and dorsiflexion directions, or other movements for other joints. In order to more clearly explain the workings of such a system, a description of two fluid filled dampers will be explained in order to provide a simplicity in explanation, but should not be considered limiting in any way. In such a system, these compliant fluid filled hydraulic dampers may be fabricated with compliancy to their movement, or may be more conventional damper methods as are used in the hydraulic industry.

With using a compliant natured device, the fluid filled damper may be fabricated out of rubber, plastic, laminate, or other flexible or semi-flexible (compliant) material selection. The damper compartment may have one or more grooves or contouring built into it in order to assist in the flexibility or compression of it. Additionally, it may have volumetric limiting agents associated with its design to limit the amount of expandability it has in certain directions. Still furthermore, these fluid filled compartments may be fabricated so that compression of the system may occur in one direction only, or in more than one direction to provide additional compliancy. These fluid filled compartments may be attached to the keel, the keel and the outer struts or structural members, just the outer struts or structural members, or neither. In general, the compression of the outer struts or members in relation to the keel may cause pressure on the fluid filled compartment, and may force fluid to travel from one compartment to the other through a fluid line. As this fluid may be constricted in its ability to travel from one compartment to the other, such as would occur in closing the valve system, the compressed strut in general may become increasingly tougher to bend, and therefore provide a more rigid, less compliant system, though the compliant nature of the fluid cavities may provide a smooth transition of the movement and forces. In essence, as the valve closes, the fluid is unable to travel from the compressed fluid filled compartment to the other, the strut is therefore not able to be pushed closer to the keel, and in general, the ankle joint is not moved. It is further contemplated that a conventional hydraulic system may encompass an embedded compliant member in order to provide equivalent benefit.

In a preferred embodiment, the fluid filled compartments may be attached to both the keel and the associated strut or member, although is not necessarily limited to such and may be attached to one or the other, or neither. By doing this however, while the posterior strut for instance is being compressed and moving closer to the keel during fluid expulsion, the anterior fluid compartment may be filling with fluid, forcing the anterior strut away from the keel. By attaching the fluid compartment with the keel and strut, it may prevent excessive movement of the strut from the keel—in essence, holding the strut to the keel through vacuum-like force within the fluid filled compartment during biomechanically attempted extraction of the system.

The fluid filled compartments may be located within an enclosed unit, or within an open unit, all together being equivalent in nature to a rotary unit as a whole with inner and outer cylinders. FIGS. 15A and 15B illustrate some specific embodiments. In FIG. 15A, a two chamber rotary unit is depicted with an inner and outer cylinder, which moved about an axis of rotation. Furthermore, the two chambers 501 and 502 are fluid filled compartments, and valve system restricts fluid flow from one chamber to another. The FIG. 15A embodiment comprises a two chamber design with an inner and outer cylinder and an axis of rotation using sealed fluid compartments to maintain the fluid within the space between the structural members. FIG. 15B depicts the same two chamber design using an inner and outer cylinder, and an axis of rotation of the two. FIG. 15B uses enclosed fluid compartments to maintain fluid within the appropriate space.

It is still further contemplated that various chamber elements may have different functions, including but not limited to power generation, power storage, energy storage, spring-like mechanisms, or other methods discussed in this disclosure.

Still furthermore, the system may use spring loaded wiper seals or other seals commonly used in the sealing industry. Additionally, it may use close tolerances to achieve sealing.

The compartments may be sealed using flexible material with an opening orifice for connecting to a valve system, and may reside within the enclosed structural members, or may reside outside or among the structural members. In either case, the fluid movement is controlled by variable fluid pressure within the fluid compartments by means of valves opening and closing, and not solely by means of variable fluid viscosity. It is understood in addition that through using MR fluid, inherently, the fluid is controlled via variable fluid viscosity.

While the above mentioned illustrations may appear slightly different in practice, the function, means of actuation, strategy, overall design, and other aspects are equivalent in nature, and should not in any way be considered limited to such expressions. Many equivalent means of depicting such a concept are contemplated, including but not limited to changing from a two chamber design, to a one, three, four, or other number of chambers, which remain in equivalency to a two chamber design in function and performance.

Through using compliant members, a more natural movement and feel will occur in the system. Still furthermore, the sealed compartments within structural members, and through using seals such as but not limited to O-rings, are by nature compliant compartments, in that the overall shape of the compartments may change shape as the system goes through a range of motion. Additionally, using fluidly controlled systems as well have compliance as the fluid may compress, the structural members may flex, and the valves may have a transition of restriction gradient as it may close or open.

The use of a valve in the fluid line may allow the fluid flow to be restricted in either, or one, direction. The use of electronic means to adjust the fluid flow may allow integration of the control system to such a mechanical and fluid dynamic system.

Still furthermore, the use of no electronic means may allow for a user selectable alteration in heel and toe load compression of the foot adjustments. Still furthermore, with a mechanical type of system, separate settings may be used for dorsiflexion and plantarflexion settings.

Strut or Structural Members for One Embodiment

The struts or structural members (term used interchangeably) may be fabricated out of flexible or non flexible members. There may one anterior and one posterior struts, or there may be more than one anterior and more than one posterior struts in order to provide additional inversion/eversion compliancy. The struts, in general, in a preferred embodiment, may be concave in nature, meaning, curved inward toward the center of rotation of the system. It should be understood however, that the struts may be generally straight or curved out as well, and not depart from the overall function of the system. By having them curve inward, a better cosmetic appearance will occur. These struts may run, in a preferred embodiment, from the attachment point of the foot to the shin, to the keel. The posterior strut may generally attach to the posterior aspect of the proximal keel. The anterior strut may generally attach to proximal keel anterior to the center or rotation. The length of keel, which the anterior strut attaches to, may be adjustable to the particular user, or may be set in a fixed location. These struts may exhibit compliancy to assist in plantarflexion and dorsiflexion of the system, or may be fabricated with more rigidity and rely on flexible members within the struts to provide bending, such as but not limited to a hinge or hinges.

Still furthermore, the keel in such a system, may have general compliancy built in, or may have little to no compliancy. Because the simulated ankle joint has so much inherent compliant nature to it, there may not be a need to rely on compliancy from the keel, as is found in conventional systems.

The use of fluid, such as but not limited to water, oil, solution, air, or other fluids may be used to provide the damping method of the fluid filled compartments. Altering the fluid flow of any one, or all, of the compartments may in general affect the observed stiffness of the struts and keel during ambulation or other activities. With the valve system fully open, the system may in general have a relatively loose feel, while when the valve system in fully closed, the system may exhibit a relatively stiff feel.

Axis of Rotation and Center of Rotation

The center of rotation, or equivalently an axis of rotation of the system may occur outside the actual mechanical components, in free space, or within the boundaries of the mechanisms. It is understood that the net effect of an axis of rotation outside of or at a non-geometric center of a mechanical device ultimately results in the equivalency of a center of rotation of the movement, as the term center by definition is the point at which the rotation is centered. Having the axis of rotation offset from the mechanical geometric center still allows for the mechanical components to rotate and have a center of rotation equivalent.

Figure 17:
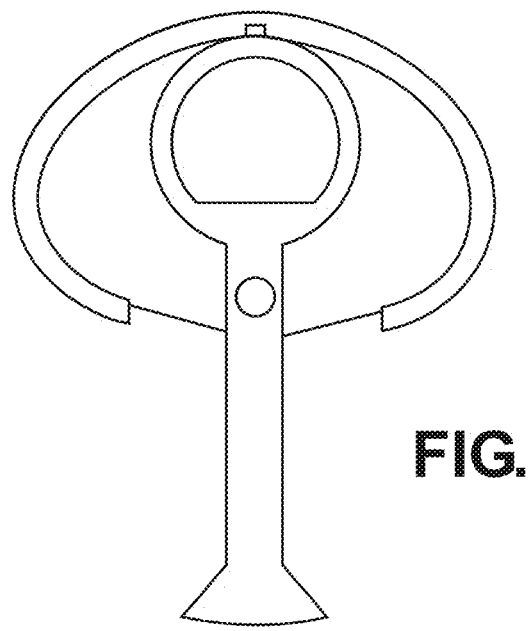
FIG. 17 is a general illustration depicting a two chamber damper with offset axis of rotation with respect to the mechanical embodiment.
Figure 18:
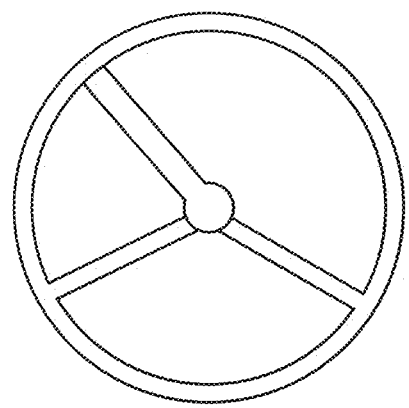
FIG. 18 is a general illustration depicting a two chamber damper.

FIG. 16 depicts a center of rotation offset from the mechanical structure geometric center, and depicts an outer cylinder with a comparable axis of rotation. This design should be considered in equivalency to other depicted two chamber systems. Still furthermore, FIG. 17 demonstrates an axis of rotation, and hence range of motion center of rotation, outside the structural member center of mass. Still furthermore, means of inducing a moving axis of rotation, or moving center of rotation may be implemented in equivalency.

Other Methods of Implementation

Figure 19:
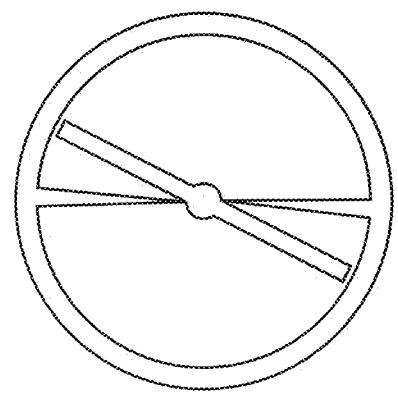
FIG. 19 is a general illustration depicting a two chamber damper.
Figure 20A:
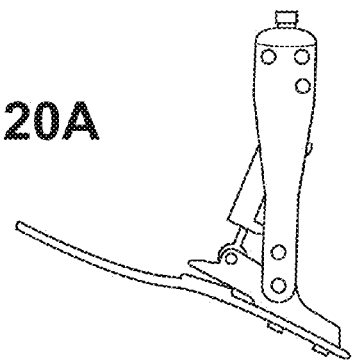
FIGS. 20A-C illustrate the use of a linear actuator to control a prosthetic system.
Figure 20B:
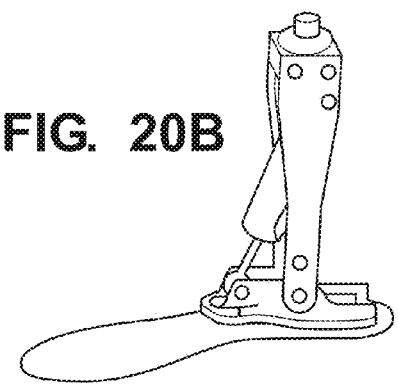
Figure 20C:
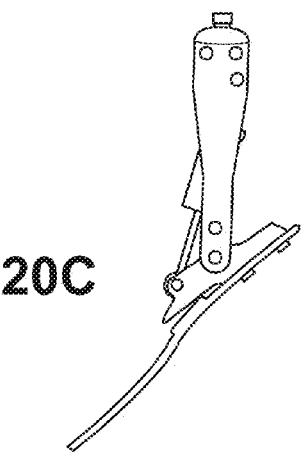

FIGS. 19 and 20 depict variations in the size and shape of the inner and outer cylinders, and hence the fluid compartments. Each of these, as well as other illustrations depicted, should be considered one and the same in equivalency, and should not be considered limiting in any way.

Figure 21:
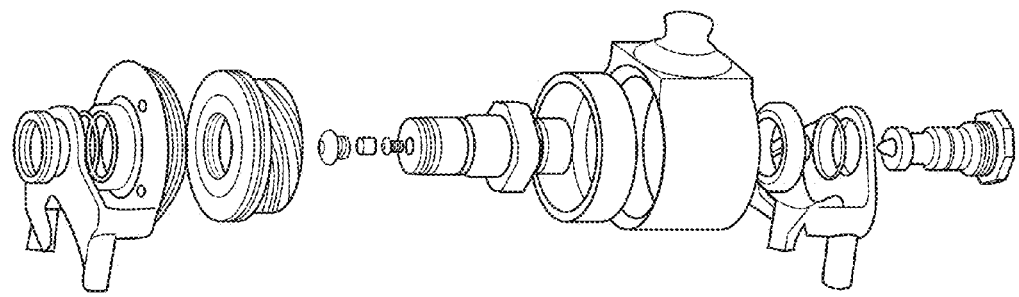
FIG. 21 is an exploded view of a damper mechanism used to convert rotary to linear motion within a two chamber design.

Still furthermore, it is contemplated to use a linear damper method to create the equivalency of an inner and outer arcs of rotation about an axis point. This method of implementation may encompass other attributes shown in FIGS. 21A-C, though not to be considered as limiting to such. As illustrated therein, a linear damper 600 is disposed so as to control the rotation of the foot, through a range of motion.

Still furthermore, the use of rotary to linear motion may be accomplished according to FIGS. 22 and 23. In a preferred embodiment, the two chambers may be located side by side, though are not limited to such methods.

Still furthermore, the use of hinged segments may be used to compress compliant fluid compartments or actuators, which may allow for movement of the device. Still furthermore, this design encompasses the same inner and outer rotatory cylinders, axis of rotation, and two fluid chambers. The method of compressing the fluid compartments may be by compliant or non-compliant members to force fluid from one compartment to another. These illustrations are used for explanatory purposes only and should not be considered as limiting in any way.

Sealing

In a preferred embodiment, the damper may use fluid of various types to control movement, as fluid may flow from one chamber to another. The fluid may be restricted through a valve type of system known in the art. Furthermore, seals of any nature may be used to prevent fluid flow from one chamber to another. The seals may be single, double, or other in number, and may be made of various materials known in the sealing industry, and may be fabricated specially for static of dynamic nature. Additionally, the fluid compartments may be fabricated out of fluid sacks, or the like, which may reside within structural members, or may reside amongst structural members. Whether the fluid is held within compartments by standard or custom seals, or within sealed sacks, the function is equivalent in nature. The term sacks is not meant to be considered limiting, but rather is used for explanatory purposes only, and is to include other forms of containing fluid, such as but not limited to seals, chambers, balloons, structural members, compliant containers, and the like. Still furthermore, the fluid sacks may be fabricated out of any compliant material, and may encompass a means for attaching the fluid sack to valve system(s). The use of fluid filled sacks, as opposed to using standard seals, may further assist in durability of the device. The compliant nature of the fluid compartments, or sacks, is to allow for the fluid to be moved from one chamber to another. Whether residing within structural members, or amongst structural members, the fluid flow characteristics is the same, and the fluid compartment must account for fluid moving from one compartment to another, and therefore must change shape. It should be understood as well that the term compliant may encompass the characteristics of expandability, or may not be expandable, but only compressible in nature.

Bracket Assembly

Referring to the drawings and in particular FIGS. 10 and 10A, in a preferred embodiment, bracket assembly 20 would generally comprise a medial bracket 134 having aperture 136 and lateral bracket 138 having aperture 140 wherein aperture 136 and aperture 140 are generally axially aligned and receive shaft 82. Furthermore, medial bracket 134 aperture 136 and lateral bracket 138 aperture 140 may be generally in a circular shape 142 with a flat portion 144 for matingly engaging shaft 82 circular portion 146 and flat portion 148 (FIG. 6B).

In a preferred construction bracket assembly 20 is pivotally connected to outer cylinder 60 such that the rotational movement is along center or rotation axis 64. It is understood that other attachment means may be contemplated wherein bracket assembly 20 is connected to inner cylinder 80 in a generally fixed manner and yet in a pivotally rotational manner with outer cylinder 60. It is contemplated that bracket assembly 20 is attached to keel 12 by attachment means 150 such as but not limited to screws 152, 154, 156, and 158. Other conventional attachment means 150 may be used wherein keel 12 may be easily and quickly be removed for other configurations of keel 12.

It should be further understood that connecting outer cylinder to the keel, and providing brackets to attach shaft to lower leg section of the prosthesis characterize the equivalent function of the system, and should not be considered limiting or altering from the previous patent application disclosure. This synonymous method may lend to providing increased durability of the system. Again, conventional attachment means may be implemented to attach bracket assembly, outer cylinder, and other such components of the system. In either case, the brackets are utilized to provide a connection between the components, such as but not limited to the keel, damper, pylon, fluid compartments, struts, etc. The brackets are designed such that they do not impede the range of motion of the damper.

It is further understood that bracket assembly 20 may be of a single piece construction (not depicted) wherein medial bracket 134 and lateral bracket 138 are joined in the middle on the distal aspect to possibly provide additional stability. The contouring of the brackets assembly 20 is preferred to minimize weight and optimize strength. In a preferred construction, apertures 160, 162, 164 and 166 are formed to reduce the material used in generally forming bracket assembly 20.

In a preferred construction, bracket assembly 20 is made from material that is light weight and provides minimal torque movement. Materials may be but are not limited to composites, plastic, laminated material, aluminum, titanium, or other metals. It is understood that alterations to the shown design of the bracket assembly 20 may be contemplated to provide other configurations for optimal strength and minimal weight.

Washer (not depicted) may be used between the outer cylinder 60 and bracket assembly 20 to generally decrease friction. Washer may be recessed into the brackets and/or outer cylinder to allow more precision fit of components against each other.

Joint Assembly Placement

Figure 11:
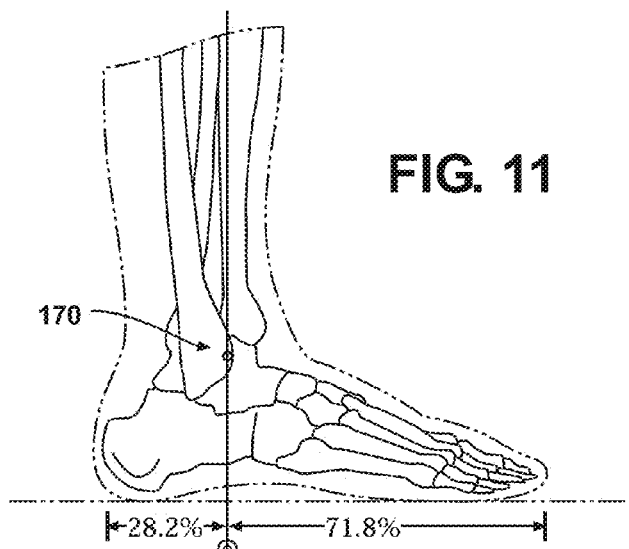
FIG. 11 is general side view of a natural human foot also generally depicting the natural weight line and rotation axis of an anatomical ankle.
Figure 11A:
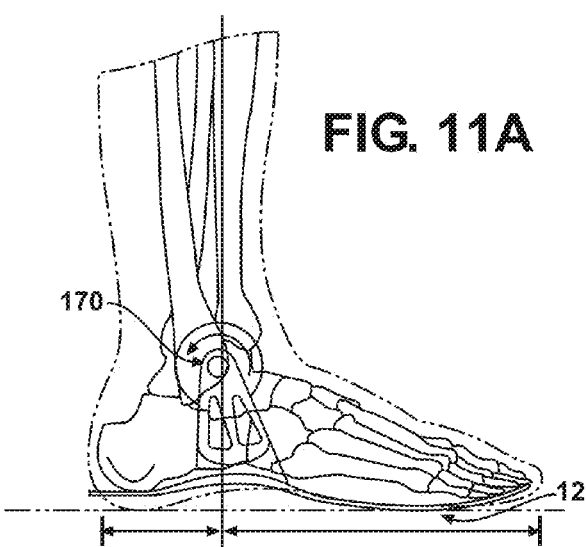
FIG. 11A is general side view of a natural human foot generally depicting the natural weight line, rotation axis of an ankle, and a preferred placement of a keel with MR dampening system center of rotation generally matching up to anatomical center of rotation as well as keel design mimicking the anatomical skeletal plantar surface of the foot in accordance with a preferred construction of the invention.
Figure 11B:
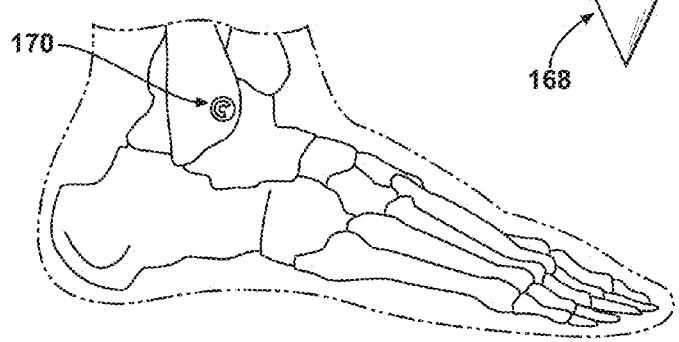
FIG. 11B is general side view of a natural human foot generally depicting the rotation axis or point of a human ankle.

Again referring to the drawings and in particular FIGS. 11, 11A, and 11B, in a preferred construction, the placement of the joint assembly 16 will be such that center axis 64 of rotation will generally fall through an anatomical weight line region 168. It is understood that typically according to the anatomical chart, weight line region 168 is approximately 28.2% of the foot length anterior to the posterior aspect of the skeletal structure of the foot. It is contemplated that joint assembly 16 rotation along center axis 64 rotation is generally along an anatomical center of rotation 170 of a natural ankle joint. It is understood that this position is in relatively close proximity to the posterior aspect of the foot, and as such the bracket assembly 20 for joint assembly 16 may begin just posterior to the weight line region 168 and run forward for support. It is further contemplated that positioning of the joint assembly 16 will provide additional keel 12 heel portion 26 compression abilities and uneven ground accommodation.

Still furthermore, the bracket or outer cylinder may attach at or near the posterior aspect of the foot, lending to little to no compression of the keel at that region. Additionally, the center of rotation of the damper may fall further posterior, anterior, distal to, or proximal to the anatomical center of rotation. It is understood that providing a joint center of rotation near the anatomical center of rotation may have significance in replicating the biomimetic nature of the design, however, through design constraints, optimization of system performance, and other reasons, there may be benefit to alter the location of the joint center of rotation. For instance, placing the damper center of rotation further anterior to the anatomical position may assist in providing a longer lever arm to increase plantarflexion moment after heel strike. Still furthermore, this may as well lend to functionally shortening the toe load lever arm and hence minimize the joint torques experienced during later portions of the stance phase gait cycle.

It should also be noted that while the keel 12 heel portion 26 may provide some compressibility from heel strike to foot flat, the majority of the plantarflexion action will come about through true plantarflexion of the keel 12 through the damper in order to better mimic NHL and provide for optimal push off characteristics at toe off, which is discussed below.

Furthermore, an inversion/eversion damper system (not depicted) may be utilized at the base of the dampening system 18 to further accommodate uneven ground. This may include bumper systems, compressible materials such as urethane or the like, joint systems, and the like. Also, other conventional inversion/eversion systems or methods may be implemented into this design to further provide uneven ground accommodation.

Finally, the use of electronically characterized means may be implemented to provide inversion and/or eversion characteristics. To do this, the use of additional damper systems, actuators, hydraulics, MR fluid, motors, springs, gears, sensors, microprocessor, or other means may be used to control the movement.

Feed Back Sensor System

Figure 12:
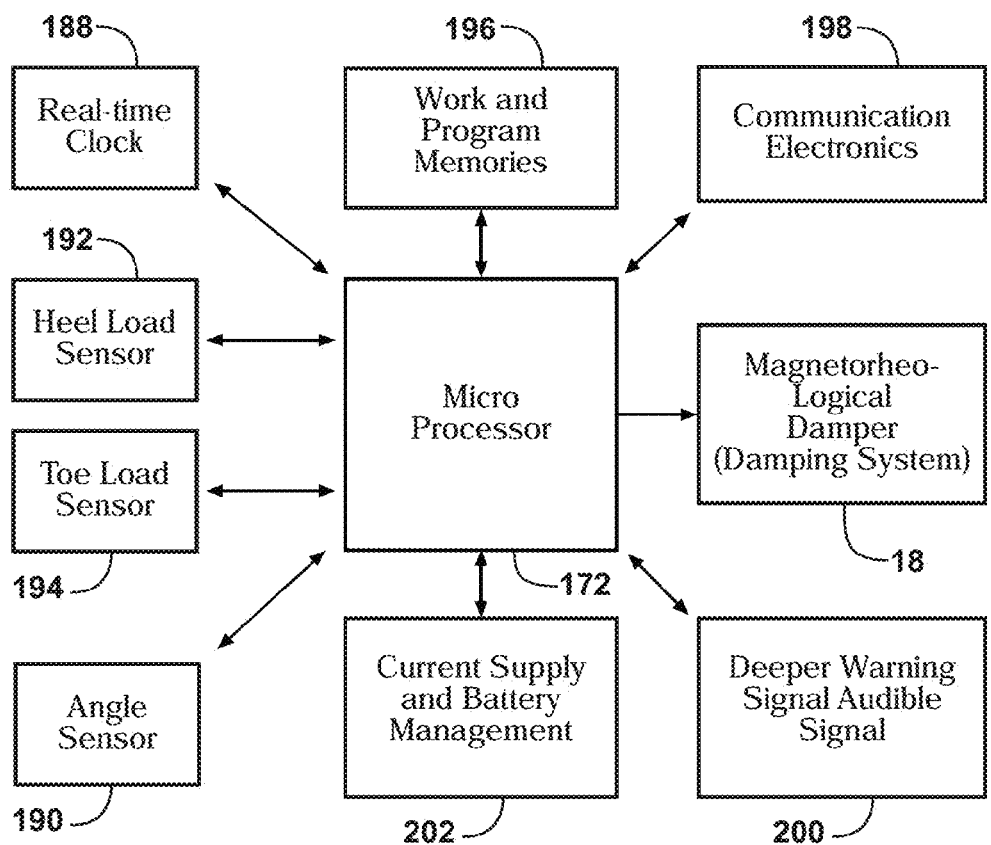
FIG. 12 is a general illustration of a flow chart depicting elements of control electronics in a preferred construction of the invention.

Referring to the drawings again and in particular FIG. 12, in a preferred embodiment, invention 10 may utilize a feedback sensor system 22. It is contemplated that feedback sensor system 22 will provide the dampening system 18 either directly or indirectly information such as but not limited to weight distribution on keel 12, forces generated on keel 12, impact times on portion of keel 12 and so forth for determination of user gait cycle to automatically control joint assembly 16 operations. Sensor system 22 may also include a strain sensor, moment sensor, pressure sensor, gyro sensor, accelerometer, or the like that may communicate with microprocessor unit 172 via wires 186 or wirelessly, as well as power source 130. Furthermore, feedback control system 22 may include a time sensor or real time clock and angle sensor, of various kinds, to compare angular velocity and acceleration (linear and/or angular) relative to center axis 64 of dampening system 18 to further assist in control of joint operations.

It is contemplated that invention 10 may further but not necessarily include a microprocessor unit 172, or other electronic systems, which communicates with sensor system 22 and in turn generally controls or communicates with the dampening system 18 of joint assembly 16 which will be discussed in greater detail below. It is understood that the term, feedback sensor system, should not be considered limiting.

It is contemplated feedback sensor system 22 may be generally located on keel 12, damper, bracket assembly, within damper or bracket assembly, on or in pylon system, or other locations. It is still further contemplated that feedback sensor system 22 may include heel sensor system 174 generally located on or in relation to heel portion 26 and toe sensor system 176 generally located on or in relation to toe portion 34, or alternatively located on or within brackets or damper to provide equivalency of information of toe and heel pressure, contact, movement, force, and other sensor related information.

Furthermore mechanical or liquid pressure/force sensors may be included within or part of dampening system 18 to determine force generally on heel portion 26 and/or toe portion 34. It is understood that other types of known sensors in the prior art may be used such as sensors that measures microscopic bending of the titanium tubular pylon to determine pressure on heel and forefoot, and others.

In a preferred construction, heel sensor system 174 may further include sensor 178 and 180, on heel portion 26 medial segment 30 and likewise on heel portion 26 lateral segment 32 respectively. Furthermore, toe sensor system 176 may further include sensor 182 and 184 on toe portion 34 medial segment 38 and likewise on toe portion 34 lateral segment 40, respectively. It is contemplated that more sensors may be utilized and located around other portions of keel 12, brackets, or damper joint to provide additional information to further enhance the control of the system as a whole. Other types of information such as but not limited to gravity, linear accelerations, rotational accelerations, sound, vibration, temperature, may be provided through other types of sensors, to again, further enhance the function and control of the system. In a preferred construction sensors and sensor systems communicate with dampening system 18 and/or microprocessor 172 via wires 186 or wireless means (not depicted in figure). It is understood that the term damping system should not be considered limiting, and encompasses all methods of altering movement of the keel with respect to the limb, and may include both resistive and powered actuation methods.

It is contemplated as well that the addition of more than one accelerometer may be used in combination to detect movement in various directions, such as but not limited to inertial elements of gait, notably foot position with respect to the ground such as but not limited to incline and decline. Accelerometers may as well be used in conjunction with gyros to combine movements of more than one joint simultaneously and in general to coordinate movement, orientation of movement, and other characteristics during usage of the device(s).

Microprocessor Real-Time Feedback

It is contemplated that microprocessor unit 172 will give real time gait analysis throughout the gait cycle as well as control the MR fluid 94 liquidity, solidification, or viscosity, or equivalently, provide control of other types of damping systems such as but not limited to hydraulic, compliant fluid systems, electronic or other valves, etc. It is contemplated that microprocessor unit 172 may function as the "prosthetic brain", but should not be considered limited to such. This design may incorporate, but not be limited to, time sensors or real time clock 188, angular sensor 190, heel portion 26 load, force, strain, or moment sensor or sensors 192, and toe portion 34 load, force, strain, or moment sensor or sensors 194. It is also contemplated that moment sensors or strain gauges may be utilized.

Time sensors or real time clock 188 may be utilized to regulate events such as allowing invention 10 to lose all, or much of the plantarflexion resistance when the user is sitting, thus, allowing the foot to be at a natural angle which is discussed in greater detail below. Still furthermore, force, angle, moment, and other sensors may be used to provide information to control plantarflexion resistance during sitting.

Furthermore, time clock 188 could regulate aspects of gait based on a profile of optimal timing for the user. Timing, as meant here, refers to providing appropriate angle, resistance to angular change, and dynamic biomimetic movement throughout the gait cycle, and in normal daily activities—providing movement that replicates the timing of the natural limb for those various functions. The timing of the joint's movement may be a function of its resistance and angular change over time. It is further contemplated that some of the discussed functions may not necessarily only be based on time factors, but may also be based on movement, such as but not limited to angular change, rotary acceleration changes, linear acceleration changes, location reference changes, or other information, or time and movement input to microprocessor.

Still furthermore, the term microprocessor should not be considered limiting, and may encompass other types of electronics, software, computer technology, nanotechnology computing, reconfigurable computing, and other systems, all of which should be considered as one and the same.

Angle Sensor

In a preferred construction, angular sensor 190 may be incorporated within the inner cylinder 80 and/or outer cylinder 60 or its equivalent to determine the relative angle of the keel 12 to user lower extremity. Angle sensor 190 may be fixed in the joint assembly 16 to determine the degree of rotation between inner cylinder 80 and outer cylinder 60. It is further contemplated that a level device (not depicted), such as an accelerometer, may be used to generally determine the keel 12 angle relative to ground.

Control Of Gait

It is still further contemplated that microprocessor unit 172 could be programmed to control speed and amount of plantarflexion at keel 12 heel portion 26 striking of the ground also referred to as heel strike. It is also contemplated to utilize existing prior art such as OTTO BOCK C-LEG for control mechanisms, through combining function of the this foot and ankle system to conventionally available prosthetic knees. In another preferred embodiment, invention 10 may work in conjunction with an artificial knee wherein microprocessor unit 172 could be utilized for both joint functions, as will be discussed in further detail below. Furthermore, it is contemplated dynamic factors could be programmed to denote how "hard" a patient generally walks. The general amount (angle and force) of plantarflexion used in walking may be set to determine push off characteristics. For example, the speed and amount of dorsiflexion of the foot after toe off may be set. Each of these characteristics may be set for normal walking as well as adapt to change as the user gait changes. The sensory feedback systems 22 may cause the microprocessor unit 172 to change the damper characteristics as speed increases or decreases, or when walking on non-level terrain. Each aspect of ankle and foot gait characteristics may be modified through in order to appropriately tailor the user's gait for perfect symmetry, safety, and function of all activities.

Programming

In a preferred embodiment, microprocessor unit 172 may be programmed with various memories or programs 196, include communication electronics 198 for interfacing or programming, and provide audible signals 200 or vibratory signals for warnings of malfunction, power level, etc.

Location

Microprocessor unit 172 could be located just anterior to the ankle joint assembly 16 on top of keel 12 or may be located on the inside of the inner cylinder 80, within pylon, or other locations as generally discussed above. It is further contemplated that microprocessor unit 172 may be located on a lower extremity prosthesis wherein a user is missing possibly above knee or below knee but above ankle.

Power Source

As generally discussed above, power source 130 is contemplated for electric supply for dampening system 18. It is further contemplated that power source 130 may be located in or integrally formed with microprocessor unit 172 and provide power for microprocessor unit 172. Power source may as well be located on any location in or around prosthesis including in or on prosthetic pylon, within foot shell, within cosmesis, or other locations. In a preferred construction, wires 173 may connect microprocessor 172 to power source 130.

It is still further contemplated that microprocessor unit 172 may include a current supply and power or battery management system 202 for further optimizing power consumption. System 202 may include on and off timers for powering down while the invention is at rest for periods of time. Typically, unless the user is sleeping or doing other non-moving activities, there will be some change in angle or force at any given time frame when the user is supporting weight, however it is known that "rest" periods of time may be for more or less than one second intervals, on regular or non-regular interval time basis. It is contemplated that invention 10 may include an automatic system (not depicted) such that if no force change is detected on sensor system 22, during a designated time, invention 10 may power down to conserve energy. In a preferred embodiment, invention 10 would power down automatically when not being worn by the user whereby the user would not have to manually turn invention 10 off. System may as well automatically turn back on when user intends to use the prosthesis. This may be accomplished through means such as but not limited to on switch, accelerometer sensor, movement sensor, system angle sensor, force detection sensor, or other means.

Still furthermore, the user may be able to check the battery level with a handheld electronics device, computer interface, initiating specific sensor readings on the device (for instance, but not limited to: tapping the foot in a particular manner, or other such activity that may initiate specific sensor response sequence), or other methods, which may provide audible, visual, vibratory, or other signals to portray battery level, or other such information.

Power Generation

It is also still further contemplated that power source 130 may be of a regenerating nature wherein the power source 130 is re-supplied through mechanical means such as but not limited to a Faraday type device. Furthermore, known technology for self-winding mechanisms with rotors, as found in self-winding or self-powering watches may be utilized. Still furthermore, fluid power or mechanical power generation methods may be implemented. It is understood that through the course of normal daily activities of using lower extremity limbs, there is a considerable amount of force used to prevent movement of the joints within the limb. Through a prosthetic device, this movement may be limited through damping mechanisms. The resistive force that is used to prevent the motion of the joint angle, may as well be used to store energy (mechanical or electrical) to power the device. This may as well come about through a system such as hydraulic reservoir or other such mechanical or fluidly controlled means, but not limited to such. Additionally, electrical power generators may be implemented to provide additional power for the system, including all or some power required for operation.

Wire/Wireless Connection

In a preferred embodiment, microprocessor unit 172 may be wirelessly programmed or controlled such as through wireless technology. It is contemplated that a user could wirelessly regulate, command, or program specific functional parameters on demand such as modifying the dampening system 18 incrementally and selectively through a remote control. Likewise, invention 10 may include a hard-wired controller (not shown) generally mounted in a relatively accessible manner on the invention 10.

Connection with Other Components

As will be discussed in greater detail below, microprocessor 172 may be used in conjunction with a myoelectric sensor system 400 and/or a sensory feedback or proprioception system 300. In a preferred construction, microprocessor 172 may be utilized as the primary and only electronic control and processing device for invention 10. It is understood, however, that multiple units may be used that work in conjunction or separately to perform the various tasks. Still furthermore, one central microprocessor may encompass various control programs, functions, such as but not limited to proprioception, sensory feedback, myoelectric, functional level alterations, and others, which may be accessed through the user or practitioner opening the option for use of that particular control program, given the systems application. A given device, ankle, knee, hip, or other, or any combination thereof, may have one microprocessor, or its equivalent, which may encompass various forms or illustrations of control programs, which may be selected from to match up with the needs and desires of a particular user. Still furthermore, a knee or hip design for instance may use the microprocessor from the ankle, which may have embedded or associated control program(s) for the more proximal joints.

Proprioception/Sensory Feedback Stimulator

Figure 12A:
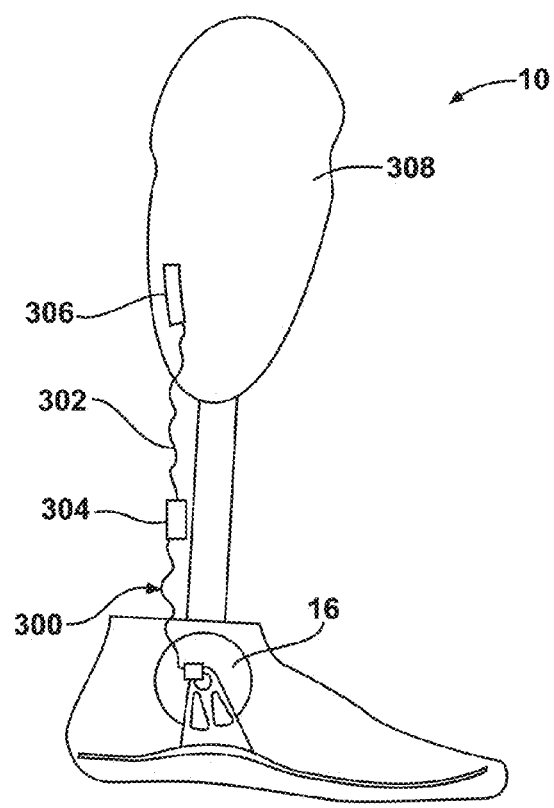
FIG. 12A is a sketch or schematic representation generally depicting a preferred embodiment of the invention wherein sensory feedback is supplied from the invention to a user.

Referring again to the drawings and in particular FIG. 12A, in a preferred construction of invention 10, prosthetic proprioception system 300 may be included. The term proprioception generally refers to general communication from the prosthesis to the user, including but not limited to angle, force, resistance to angular change, temp, and other feedback modalities. Still furthermore, proprioception system inherently includes information from sensors to the microprocessor, or its equivalent, to control movement. In either case, information from the extremity is relayed to the control mechanism, whether human or prosthetic brain, to initiate a response in intended movement alteration and knowledge.

Figure 33:
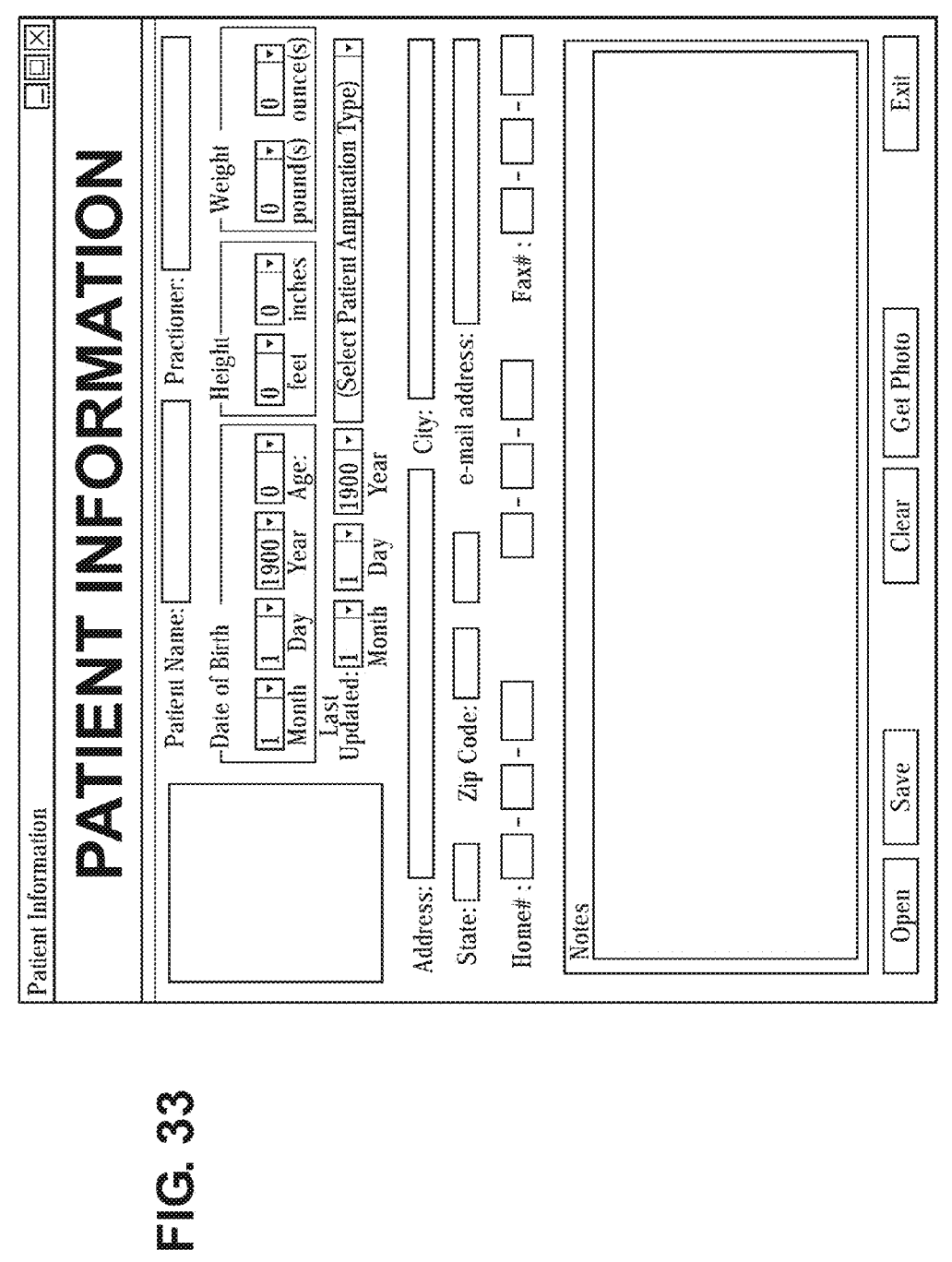

The more feedback information that the prosthesis can provide to the user, the greater the external physiological proprioception may be. With conventional prosthetics, the ability to understand external physiological proprioception is relatively simple because the prosthetics movement is consistent. With a device that has the ability to change its state—angle, resistance to angular change, etc.—the need for greater feedback is essential because the user has no other way of knowing the prosthetics state, and the external physiological proprioceptive sense may be inherently limited. According to FIG. 33, the prosthetic, orthotic, or robotic system as a whole may function in a similar manner as to the anatomical sensory feedback mechanisms, which include input from the user, actuation control of angle, angular change, resistance to angular change, force, and other parameters, and then relays information from the extremity back to the user, brain, controller, microprocessor, or their equivalent.

It is contemplated that the invention 10 may provide instantaneous communication or signals from the prosthesis to the user wherein feedback is provided such that a sense of spatial and/or angular orientation of a prosthetic joint is achieved, as well as other proprioceptive information such as resistance to angular change.

For reference, FIG. 12C generally illustrates elements of a natural human system for proprioception feedback pathway. Furthermore, FIG. 12D general illustrates a flow chart depicting elements of a natural human system for proprioception feedback.

It is understood that in the human body, the brain analyzes the required movements of our extremities as well as has knowledge of the positioning and resistance to change of our joints and orientation in space. Small proprioceptor sensors in the human muscles and joints, such as joint kinesthetic receptors, neuromuscular spindles, and neurotendinous receptors, send sensory information to the brain to tell it where the limb is orientated in space as well as its movements such as stretching of the muscles or bending of the joints.

Prior Art

It is also understood that there are systems in the prior art which relate to pressure sensor on the prosthetic foot or hand which may relay information through a small microprocessor and then stimulate the limb in a similar fashion, thus tricking the brain in thinking that the wearer is "feeling" with the prosthetic limb. It is contemplated that invention 10 may provide information relating to the angular position and change, including resistance to angular change, within the prosthetic joint and stimulate the limb 308 in a designated manner, thus providing what may become a subconscious feedback of the position and angle of the limb's spatial orientation. Furthermore, the resistance to that angular change may be characterized through proprioceptive feedback.

Safety and Energy Expenditure

It is contemplated that invention 10 may provide greater safety through "knowing" the position of the prosthetic joint in space, as well as the resistance to that change. By example, "knowing" or "feeling" that the ankle joint is plantar flexing excessively due to wearer beginning to walk down a hill. This information may be especially important to the user due to the dynamic state of the ankle joint. Conventional prosthetics move in a fixed resistance about a fixed point, therefore providing movement that is expected by the user.

Furthermore, it is also contemplated that there will be a decreased energy expenditure through providing a more natural gait pattern as well as providing an enhanced mental confidence in the prosthesis and therefore greater functionality. Likewise, the user may have a sense that the prosthesis is more of a part of them through enhanced human/machine interaction.

It is contemplated that the user's brain will learn the sensory feedback from the system as subconscious proprioception or cerebral projections. While numerous methods of stimulus may be incorporated, some may provide more information that the user can comprehend.

It is contemplated that the user would generally connect, communicate and interact with joint assembly 16 via communication means or system 302. It is further contemplated that a separate microprocessor 304 may be utilized or microprocessor 172 or even a combination thereof. It is further understood that prosthetic proprioception system 300 may be utilized on other joints as well as ankle joints or other prosthetic joints, such as knee, hip, hand, elbow, and shoulder.

Furthermore, it is contemplated that the prosthetic proprioception system 300 may be utilized on an individual that has lost feeling or lost the sense of proprioception or control in their natural extremity.

The use of Sensory Feedback in prosthetics may assist the user in having greater safety, symmetry, and lifelike appearance in ambulating, as well as provide enhanced psychological connectivity between the prosthesis and the user.

Proprioceptive, and other Sensory Feedback information, may be used to further assist the microprocessor to function in the most appropriate manner possible, through providing additional information to the control program. Still furthermore, when considering that in a preferred embodiment, the prosthetic system as a whole should interact, connect, and communicate with the human body as one complete system. In doing so, with the user being able to "feel" and in general comprehend the happenings and environment conditions of the prosthetic system, the user may be able to further control the function, movement, and actions of the prosthetic system.

Types of Feedback

In a preferred construction, it is contemplated that feedback mechanisms 306 may include pressure variance with angular change or resistance to angular change, pressure movement with angular change or resistance to angular change, electrical impulse to limb 308 with angular change or resistance to angular change, vibratory variance with angular change or resistance to angular change, and other conventionally known methods. Furthermore, it is contemplated that prosthetic proprioception system 300 may utilize angle or positional sensor in conjunction or separately with a sensor to detect resistance to angular change of a prosthetic joint, and provide feedback thereof. It is further understood that alterations of the sensor signal of any of the above mentioned or other methods, of stimulation may occur to characterize more than one type of signal through a given mode of stimulation. For illustration purposes, altering amplitude and frequency of an electrical stimulus may provide at least two distinct pieces of information, relating to angular change and resistance to angular change. Other methods of altering signals may be used in equivalency to provide necessary or desired information to the user.

Figure 12B:
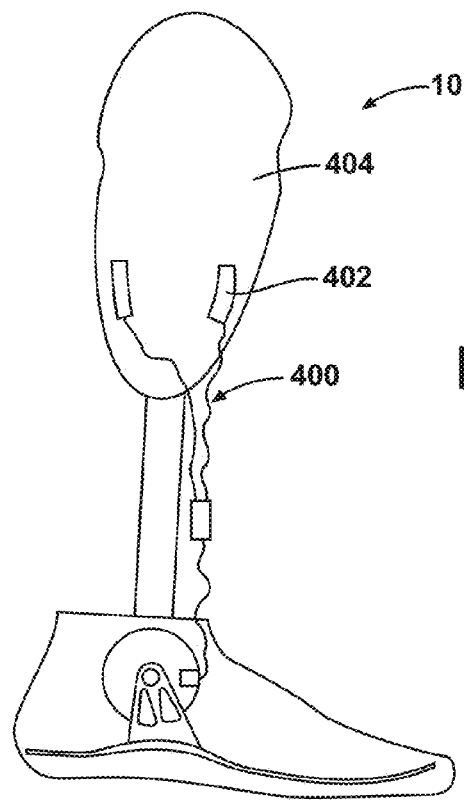
FIG. 12B is a sketch or schematic representation generally depicting a preferred embodiment of the invention wherein sensory feedback is supplied from the user to the invention.
Figure 12E:
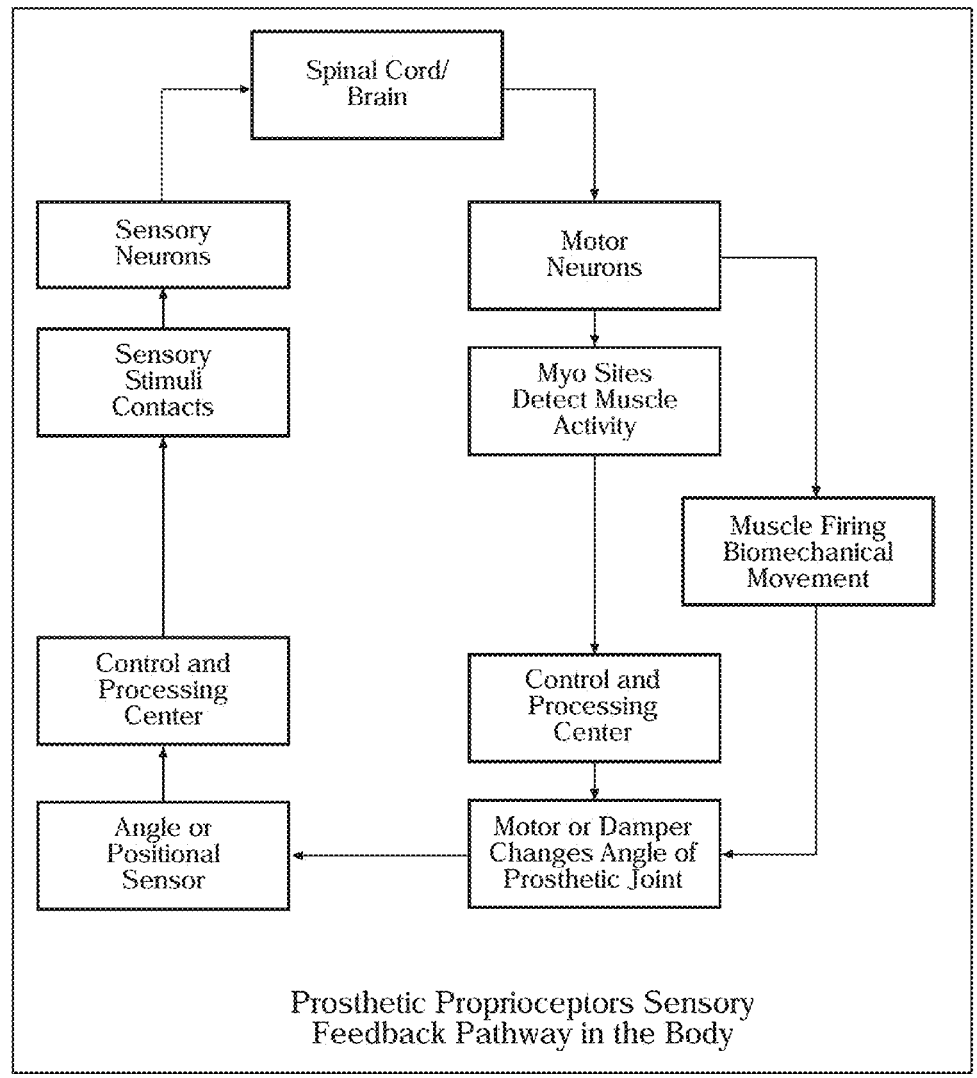
FIG. 12E is a general illustration of a flow chart depicting elements of a system for proprioception feedback pursuant to a preferred embodiment of the invention.

Now referring to FIG. 12E, generally illustrated is a flow chart depicting a preferred embodiment of invention 10. It is contemplated that integration of the various sensors and feedback may be controlled by microprocessor 172 or through an independent processing system or combination thereof.

It should be further understood that other sensory stimuli systems may be implemented in a similar manner, such as but not limited to force, vibration, tactile stimulation, direction of force, texture, shape, audible, and other stimuli—all defined by the term Sensory Feedback. The term Sensory Feedback should not be considered limiting, but should in general define providing information to the user of the actions, movements, sensor information, and other desired information that may be gained from the prosthesis to the user.

Connectivity

Figure 12F:
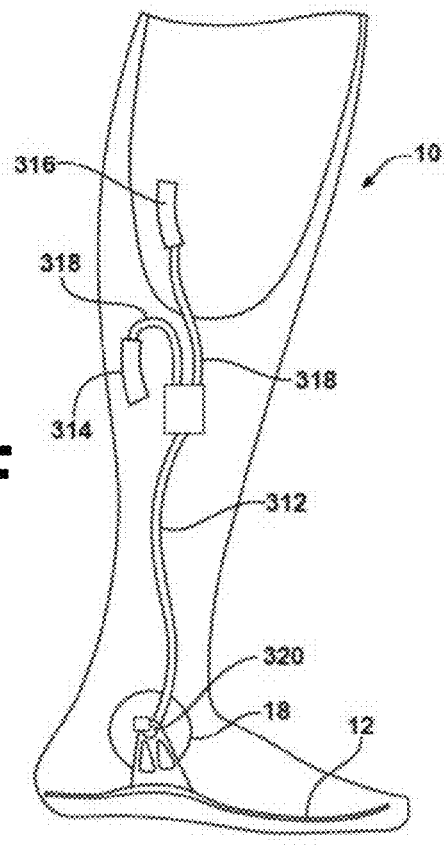
FIG. 12F is a sketch or schematic representation generally depicting a preferred embodiment of the invention wherein sensory feedback is supplied from the invention to a user.
Figure 12G:
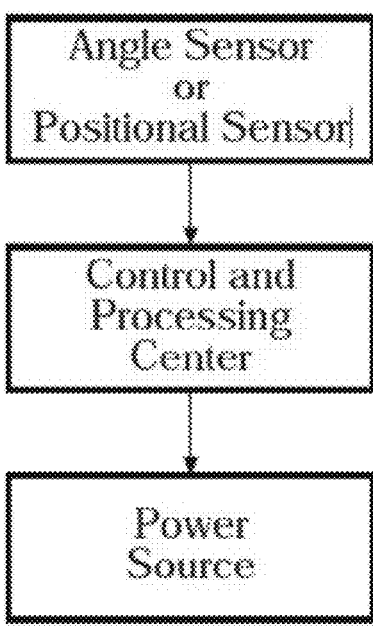
FIG. 12G is a general illustration of a flow chart depicting elements of a system for proprioception feedback pursuant to a preferred embodiment of the invention.
Figure 14:
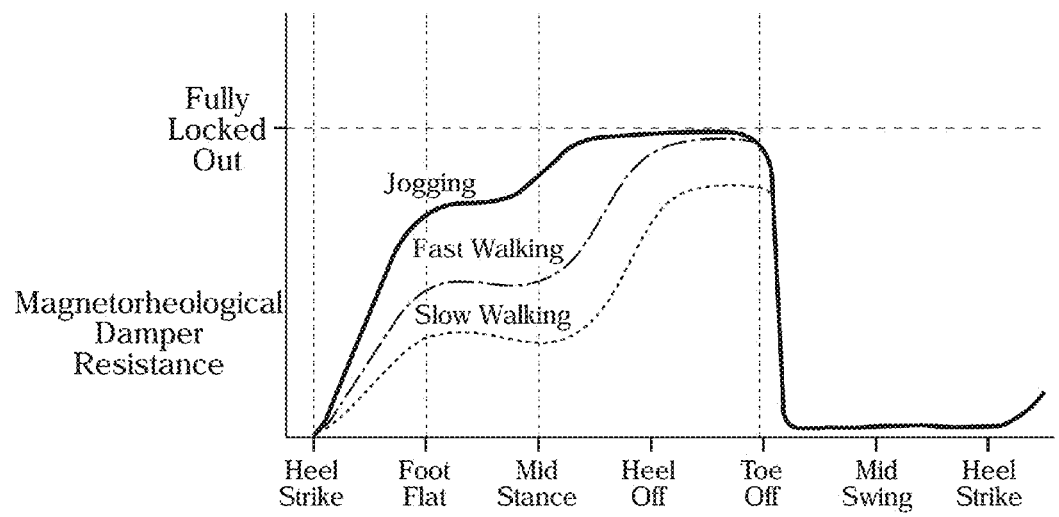
FIG. 14 is a graphical presentation showing general characteristics of magnetorheological fluid damper resistance during a gait cycle in a preferred construction of the invention.
Figure 14A:
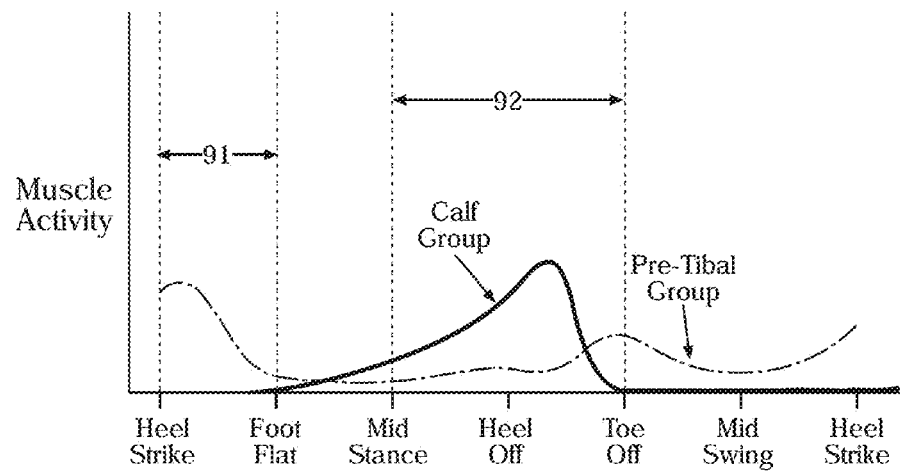
FIG. 14A is a graphical presentation showing general characteristics of natural human muscle activity during a gait cycle.

Referring now to FIG. 12F another preferred construction is generally depicted wherein keel 12, dampening system 18, ankle joint assembly 16, sensor system 22 is in general communication with wires 310, or through wireless means, through microprocessor 312, power source 314, sensory stimuli contact 316 and wires 318. It is understood that microprocessor 312 may be microprocessor 172 or through an independent processing system or combination thereof. Power source 130 may also be used. Sensor system 22 may include angle or position sensor 320, force sensor to determine resistance to angular change, or others. Likewise, FIG. 12G is a general flow chart of a preferred embodiment invention 10 as discussed.

Now referring to FIG. 12H, another preferred embodiment of invention 10 is generally depicted wherein the prosthetic is directed to a non-ankle joint although a prosthetic hand is generally illustrated, it is understood that invention 10 may be utilized on other joints, prosthesis, orthotics and combination thereof. Socket 322, frame 324, sensory stimuli contact 326, wires 328, cosmetic cover hand shell 330, internal hand components 332, hand motor 334, hand connector piece 336, power source 338, microprocessor 340, angle/position sensor 342 and other force and other sensors, and hand connection piece 344 are generally shown working in communication. Likewise it is understood that power source 338 may be utilized separately or in conjunction with power source 130 and may also be but is not limited to a myoelectric or other battery. It is also understood that microprocessor 340 may be microprocessor 172 or through an independent processing system or combination thereof.

The stimulatory feedback devices may be incorporated within the socket system to interact with the residual limb, outside of the socket system, mounted on or in the prosthetic frame or socket, mounted within a cuff or other embodiment for use as a housing, or other means.

Myoelectric Sensor System

Once again referring to the drawings and in particular FIG. 12B, a preferred construction of invention 10 may further include a myoelectric sensor system 400 wherein a generally closed loop sensory feedback system is contemplated. Myoelectric controls and/or myoelectric sensor system 400 may provide a prosthetic system wherein instantaneous communication or signals from the user to the prosthesis is achieved for better regulating, controlling, or positioning the prosthesis. It is understood that the human body produces electrical signal through muscular and other activity.

It is understood that the term myoelectric may generally refer to communication from the user to the prosthesis, and may include conventional technology to read nerve signals through surface or implanted means, or other methods such as but not limited to pattern recognition. Other methods of reading communication from the user to the prosthesis are actively being developed, including but not limited to implanted peripheral or cortical nerve sensors, which may be used to control such a device. Still furthermore, information from the sound limb may be used to control the movements of or inputs to the device. This may be done during a training session, or may be done for typical use.

This control program, in a preferred embodiment, may utilize signal analysis, signal decoding, pattern recognition, neural control, or other methods of processing the myoelectic signals to effect the damper. The myoelectric signals as well may come about through surface, implanted, or other methods of characterizing myoelectric signals from the body. It should be understood as well that other methods of taking information from the human brain or efferent nervous system, and applying that to control prosthetic movement may be utilized as well, such as but not limited to implanted electrode arrays, nerve grafting with electronics elements, or other means. In general, any method of controlling a prosthetic device through intended human initiation, conscious or subconscious may be utilized.

The control program may allow for myoelectric, neural integration, pattern recognition, or other such human to prosthesis, orthotic, or robotic interface to have an alterable effect on the control. For instance, the neural integration strategy may provide up to 100% control of the devices movements, or may provide 0% of the movements. The amount or percentage of the influence that such devices may have can be adjusted manually through any available means including but not limited to the GUI, or may be automatically altered through control program parameters, such as but not limited to be correlated with the user's available strength, abilities, functional abilities, neural sensor signals, sensor signals, or may be altered gradually over time, as well as other methods. By altering the effect that the neural integration strategy may have over device control may be advantageous during training of the user for the device. This may allow someone with poor neural integration control of the device to gain greater functioning slowly over time as the system may force the user to have increasing control of their neural signals.

Still furthermore, the prosthesis system may employ pattern recognition to differentiate between different user inputs or to analyze the historical data stored in its memory bank to recognize different gait or terrain patterns. This functionality may be present initially, or may be a feature, which is unlocked at a later time, or may be installed separately as an update. This is only meant to be an example, and the presence or absence of this feature is not meant to be limiting in any way.

The prosthesis system may use learning algorithms for pattern recognition such as Hierarchical Temporal Memory algorithms or any other algorithms applicable to that purpose.

Virtual Reality Training

Still furthermore, the user may place any of the available neural input strategies on the sound limb in a manner as to extract necessary data, integrate a virtual reality, or its equivalent, system to control the functions of the prosthesis. This may include, but is not limited to pattern recognition, myoelectric input, accelerometers, and other such sensor data. Still furthermore, the use of data and neural input capturing devices may be used on other parts of the body not including the extremities, including but not limited to the brain. It is further contemplated that the user may move his/her sound limb in a manner in or out of the virtual reality system that is typical for a given activity, and the neural information may be processed to ultimately control the prosthetic device in a similar manner. The user may use imagery as well to gain symmetrical neural inputs to both sides, of which may be processed to better control the limb. This may be done as well to incorporate pattern recognition systems into control of the device.

Control Of Gait

It is contemplated that in a preferred construction, dampening system 18 is generally controlled by the myoelectric sensor system 400. It is understood that myoelectric sensor system 400 may or may not necessarily cause movement of the ankle joint assembly 16, but rather is allowing the user to adjust the rotation or slow down the angle progression during stance or swing phase of gait. The joint assembly 16 movement may still generally be achieved through natural biomechanical movement during ambulation besides or in addition to the inclusion of myoelectrics. The dampening system 18, corresponding sensor system 22 such as pressure, and myoelectric sensors system 400 generally may limit the speed or movement, such as angle change, of the ankle joint assembly 16 as it rotates. It is contemplated, therefore, anatomical musculature control of the lower extremity prosthesis, or more specifically the ankle joint assembly 16, is achieved. It should be understood that the term damping system should not be considered limiting, and should include any such method of articulating, moving, changing the state of, expanding, contracting, bending, or any other means of adjusting the mechanical assembly to initiate and cause joint movement or simulated joint movement.

It is further understood that myoelectric sensor system 400 may be utilized on other joints as well as ankle joints or other prosthetic joints, such as knee, hip, hand, elbow, and shoulder, as well as orthotics. Likewise, it is understood that myoelectric sensor system 400 and proprioception system 300 may be both included in a preferred embodiment or separately. It is understood that some myoelectric systems are known for use in upper extremity prosthetics and knee systems.

Myoelectric sensor system 400 may include stimulators or controls 402 which may be placed on the residual limb 404 of a user (i.e., on the pretibial and gastrocnemious group for transtibial amputees) or other areas outside of the prosthesis, to control or manage dampening system 18. By example, as the user fires their gastrocnemious muscle group, such as they naturally would during the midstance to toe off portion of the gait cycle at the beginning of midstance, invention 10 may increase resistance in the dampening system 18 and therefore provides greater resistance toward toe off portion of the gait cycle. User may then actively control their joint angle during ambulation as with a real foot.

Powered And Resistive Control

Furthermore, it is contemplated that damper may be dynamically or actively controlled, passively controlled, or a combination of dynamic and passive control through myoelectric or user input. Dynamic control refers generally to providing active power to initiate and change, at least partially, the speed, angle, or resistance to angular change of the damper. This method may provide all or partial, augmented power, to the damper to assist control. Passive control generally refers to the ability to altering the resistive nature of the damper only—whereby preventing angular change, and hence effecting speed of the damper during gait. A combination of both active and passive power may utilize times of damper control using a resistive nature and active powered nature during various times of the gait cycle. This may be beneficial through mimicking the eccentric and concentric contractions of the leg during walking.

For instance, the user may want to provide 100% power to the user, so that the device lifts them up a flight of stairs with little to no power generation of their own. Conversely, the user may want to provide 70% of power (or 70% of body weight) so that they have to provide the resulting 30% with their thigh or other muscles. This would enable for an "augmented power" system and force the user to use his own muscles to provide movement, resulting in improved musculature, circulation, and proprioceptive control. Furthermore, the control system could be set to provide less and less power over time so that the user slowing strengthens his muscles by forcing him to perform the same action with less power from the device. This would be beneficial during rehabilitation.

During the gait cycle, the anatomical leg may eccentrically contract to resist angular change, such as between heel strike and foot flat, when the tibialis anterior muscle eccentrically contracts to slow the plantarflexion of the foot. Alternatively, the anatomical leg may concentrically contract during the gait cycle, such as after toe off when the tibialis anterior muscles cause the foot to dorsiflex during the swing phase of gait for instance. It is understood that a combination of active and passive power may be beneficial in a preferred embodiment to best simulate full gait biomechanics and dynamic properties. Still furthermore, it is understood that the utilization of active, passive, or a combination of active and passive control may be utilized to characterize ambulation. The use of myoelectics to control such movements may be used in combination with a control program to best characterize intended movement. Still furthermore, the user of a sensory feedback or proprioception system may be used to characterize the movements from the prosthesis to the user.

Augmented Power

Still furthermore, augmented power may generally be realized through providing partial dynamic or active power of the device for the intended movement. It is contemplated that it may be beneficial to provide a portion of the power necessary for intended movement of the prosthesis, and rely on the user to provide the additional power. For instance, when transversing up a flight of stairs, it is contemplated that providing a portion of the power to raise the user up each step may come about through initiation of dynamic, active power of the knee, and rely on the remainder of the power necessary to raise the user up the step from the user themselves. This may be beneficial by allowing the user to maintain the need for utilization of their own musculature to maintain strength, coordination, and provide inherent proprioception of their intended movements through the prosthetic device. The level of augmentation of the power of the prosthesis may be controlled through a control program, which may be set by a practitioner or user, and may be manually or electronically altered over a period of time for training and user ability purposes. The amount of power that the prosthesis provides, versus the user, may be varied over time, in correlation to the user's myoelectric signals, in correlation to the user's muscle strength, through use, or other systematic alterations. In addition, the level of power that the prosthesis may provide may decrease a certain amount over time so that it systematically causes the user to rely more and more on their own muscle strength. This may be a beneficial therapy tool.

Benefits

It is contemplated that a preferred construction may enhance muscle tone and muscle strength in residual limb 404 and consequently may improve circulation. Of note, 70% of amputations are secondary to circulatory insufficiencies. Invention 10 may therefore prevent higher level amputations as is often the case with patients with severe circulatory insufficiencies.

Accordingly, invention 10 may also provide control for the user, increases safety, symmetry, confidence during ambulation, and further controls plantar-flexion and dorsiflexion. Likewise, it is contemplated energy or power required myoelectric sensor system 400 and/or proprioception system 300 would be minimal relative to other power generally contemplated by invention 10.

Functions/Ambulation

Generally referring to the drawings and in particular FIGS. 13, 14, 14A, and 14B, the following changes to the invention 10 in general or dampening system 18 in specific may be allowed to best mimic natural human locomotion during ambulation. It is understood that the control program and its associated functions, characteristics, methods, methodologies, implementation, and the like, may be equivalently utilized in other joints such as knee, and hip, for prosthetic, orthotic, and robotic applications. Still furthermore, the control program uses means of taking any number of sensor signals that characterize limb motion and may process the sensor signals, along with time signals, and may use that information, amongst others, to characterize limb defining moments, and may hence compare to typical limb motions during ambulation and non-ambulation activities. It is understood that the DOUBLE HUMP GRAPH as depicted in the original patent application is characterized by these characteristics, as the general patterns of the graph demonstrate a change in resistance levels associated with defined moments in the gait cycle, which must be comprehended or understood or defined by the sensor's data.

Furthermore, as described in the original patent application, the double hump graph illustrates the general resistance, and hence relative inverse relationship to angular velocity, of the ankle angle during the gait cycle.

In a preferred embodiment, the plantarflexion angle may be increased during the gait cycle corresponding to increase in speed.

Control System Calculation Strategies

The control system in general may operate through any number of mathematical models, artificial intelligence programs, equations, neural networks, or other methods of controlling such a device, and should not be considered limiting. In one embodiment, the system's control may be based off of approximating nonlinear functions using methods such as neural networks to provide feedback controllers for systems where the weights of the neural network are updated based on the critic function. In a preferred embodiment, defining points may be used with equations as stated below to control such a system, but should not be considered limiting in any way.

Ambulation and Defining Points

It is understood that during the walking gait cycle, there are defining points, which illustrate the normal locomotion parameters. These defining points generally include Heel Strike, Foot Flat, Midstance, Heel Off, and Toe Off. It is understood that between Heel Strike and Toe Off the limb is generally in a Stance Phase of gait. It is also understood that between Toe Off and Heel Strike, the limb is generally in a Swing Phase of gait. It is known that, in general, these described defining points fall in progression, but that it is also sometimes observed that these defining points may occur in various other orders through various abnormal or other gait activities. These defining points may be used in the below descriptions for illustrative purposes, and should not be considered limiting in any way. They are meant for clarity of reading and comprehending the complicated functions of the control program. Furthermore, it should be understood that other gait dynamic characteristics occur, such as but not limited to ankle rocker, heel rocker, forefoot rocker, and others. These various biomechanics parameters of the gait cycle should be largely replicated through the functions of the control program in general.

Types of Actuations Strategies

It is understood that invention 10 may include various forms of actuation, such as but not limited to hydraulic, mesofluidics, pneumatic, regenerative, MR fluid, active or dynamically powered, passively powered, mechanical, or other methods, including but not limited to Newtonian and non-Newtonian based fluids. The described control program for invention 10 should not be considered limiting when describing a particular means of activation or actuation, but rather, it should be understood that the described methods in general depict a contemplated form of actuation in conjunction with the control program. Other expressions of actuation strategies may be implemented in conjunction with the described control program, and do not depart from the scope and purpose of the described invention. The control program may be modular to work in conjunction with various expressions of actuation strategies.

Still furthermore, the system may provide spring-type, elastic-type, resistive-type, and/or powered-type actuation, or any combination of the above during the gait cycle. This may be accomplished through altering the state of various, or numerous, valves or their equivalent, to control the fluid flow between various chambers in order to allow the fluid to travel from one method of actuation area to another within the system. Still furthermore, other components may be added to allow, for instance, the hydraulic fluid to fill a spring loaded, or other resistive methods, compartment during high pressure within the system. This would allow for storage of energy during the portions of the gait cycle where there is excessive energy being dissipated, and stored for release at the appropriate biomechanical time when active muscular push off occurs for instance, such as but not limited to stair descent or at the end of the stance phase of gait. Still furthermore, it may be used for joint positioning. This may allow device to exhibit variable stiffness, spring, active power, and/or resistive motions depending on the valve and fluid flow path.

Valve Position and Resistance Correlation

Again, the description of valve position manipulation may as well be correlated to other actuation expressions such as through mechanical or other means. The description of valve position manipulation is meant for descriptive purposes, and should not be considered limiting. It is generally understood that in reference to a hydraulically, pneumatic, fluidly, or MR fluid actuated system (or other types of systems including a control valve), the valve position may be correlated with resistance. As the valve may tend to close, there may be a larger force required to initiate or sustain movement in the damper. Conversely, as a valve position may tend to open, allowing more fluid to pass through, there may a lower amount of force to cause or sustain movement in the damper. Likewise, the resistance of the damping unit is generally inversely proportional to angular velocity, $\omega$, during normal ambulatory activities. As the valve may tend to be in a more closed position, the unit may tend to move through a given angle more slowly, given a force, and therefore angular velocity may be lower. It is important to understand this general relationship in order to understand the general premise of the control program.

In a preferred embodiment, the valve position is being controlled. It is understood that equivalently, the resistance, angle, angular velocity, angular acceleration, or other parameters may be controlled by controlling the valve. Because each of these variables is highly related, for explanatory purposes, the discussion will refer in general to controlling valve position only. It is understood that the term valve position may be equally replaced with other variables, and methods of implementation, and not depart from the scope or intention of the explanation. The particular explanation is suited for readability and comprehension, and should not be in any way considered limiting. It is understood that many other equivalent methods of altering the state of such a damper mechanism may be expressed, resulting in similar effect, and does not depart from the scope of this disclosure. The term valve should not be considered limiting in any way.

Valve Types

It is contemplated that any number of valves may be used that reside in the prior art, to control such a device. In general, invention uses variable fluid flow characteristics of the valve system to manage movement of the device. This includes variable orifice size or contouring, or its equivalent, variable flow types through the orifice, and altering the thickness of a variable fluid within a valve, amongst others. These may include but are not limited to needle valves, rotary valves, servo valves, electronic valves, pressure valves, check valve, gate valve or any other type of valve that may be used in a hydraulic, fluidly actuated, pneumatically actuated, mesofluidic, or other system. Furthermore, these valves may be controlled by pulse width modulation or other known methods. One depiction of a preferred embodiment, though not limited to such, may be a valve similar to FIGS. 26 and 27, where a non-uniform, slanted, arched, screwed, or other groove, hole, opening, contouring, or other may be used to provide varied resistance of fluid passing through or by.

Valve Signal Strategies

Figure 32:
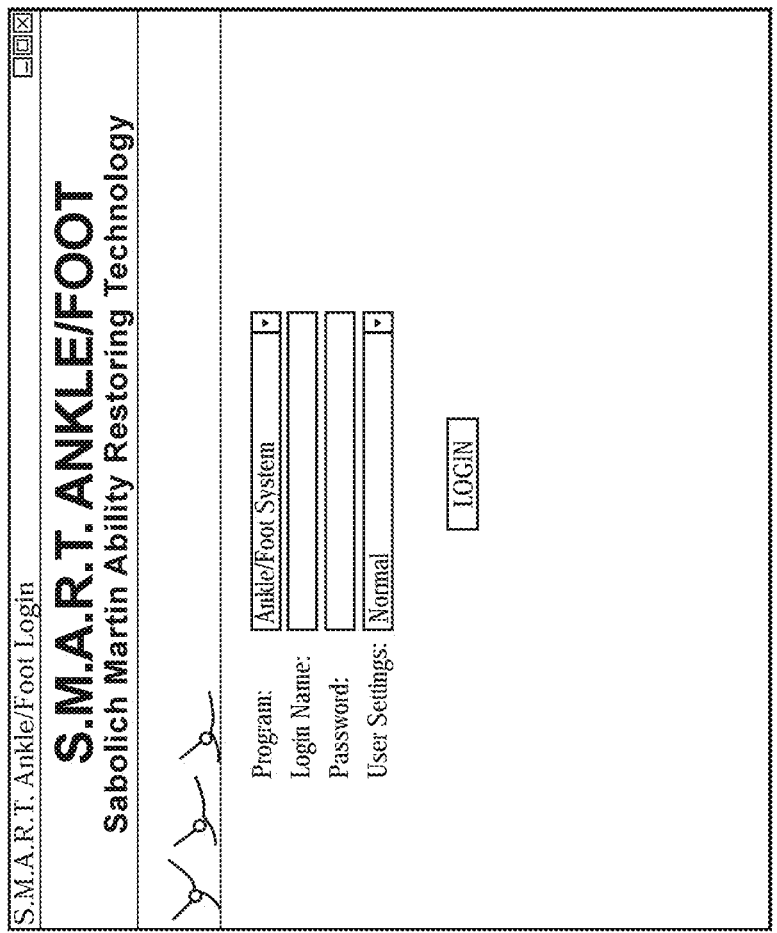
FIG. 32 is a general illustration depicting a login page for a control program.
Figure 34:
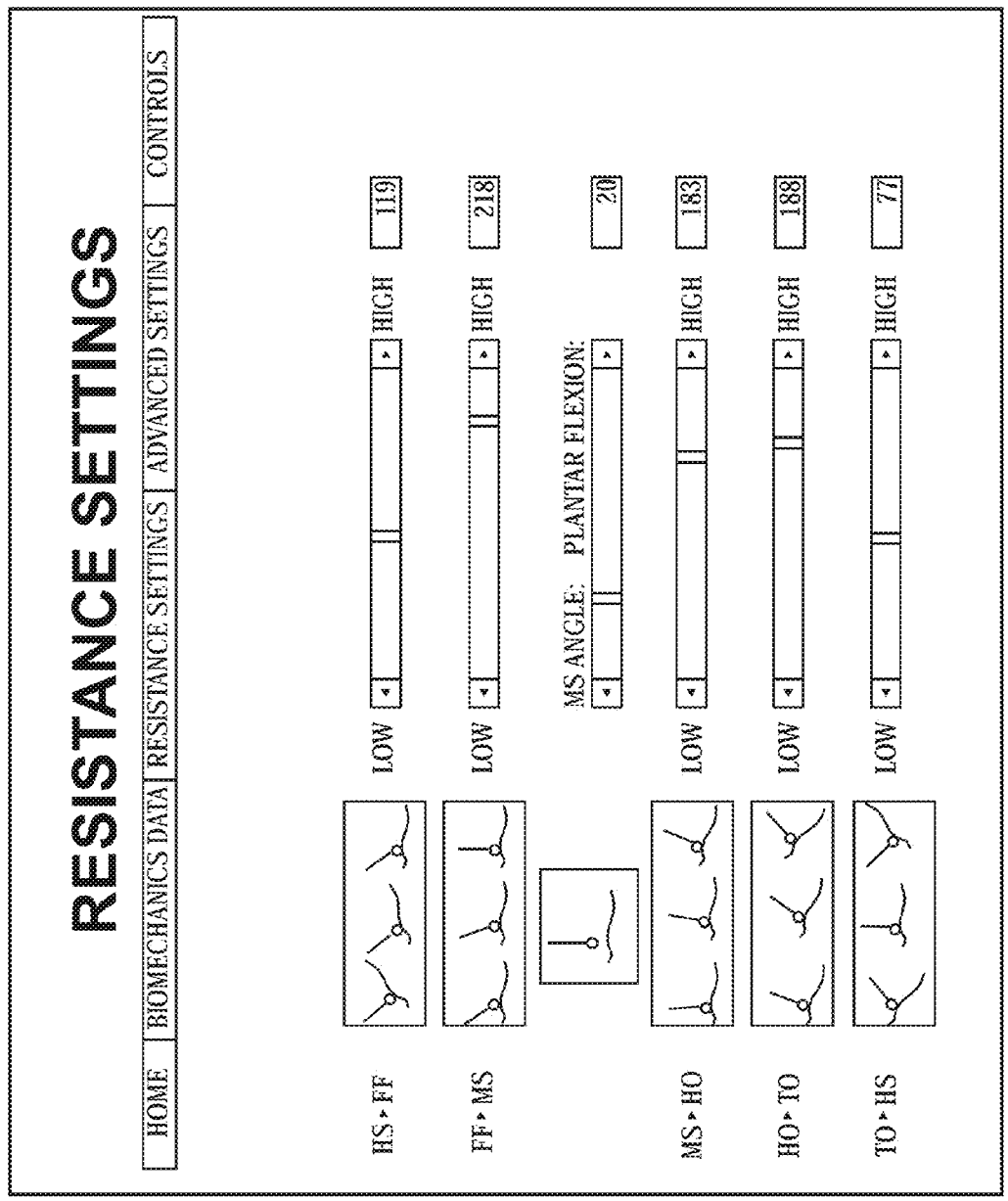
FIG. 34 is a general illustration depicting a resistance settings page for a control program, including possible adjustable variables, including but not limited to general plantarflexion angle experienced during midstance or other portion of the gait cycle.
Figure 35:
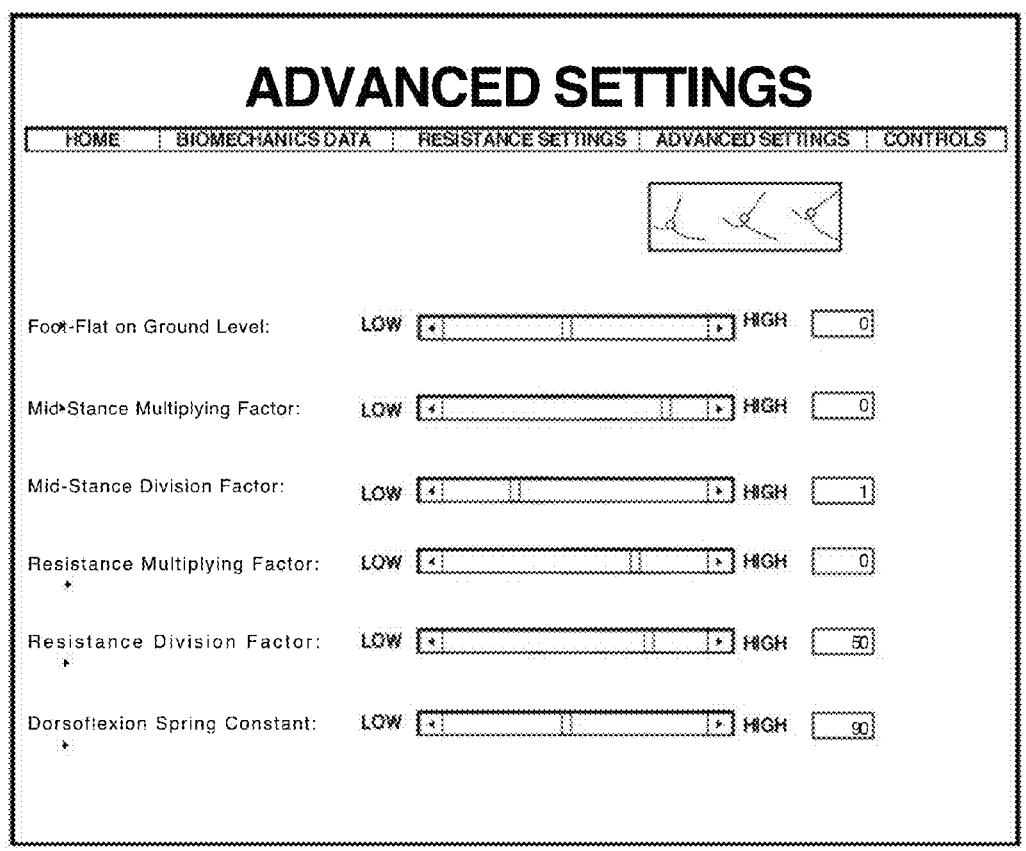
FIG. 35 is a general illustration depicting an advanced settings page for a control system.
Figure 36:
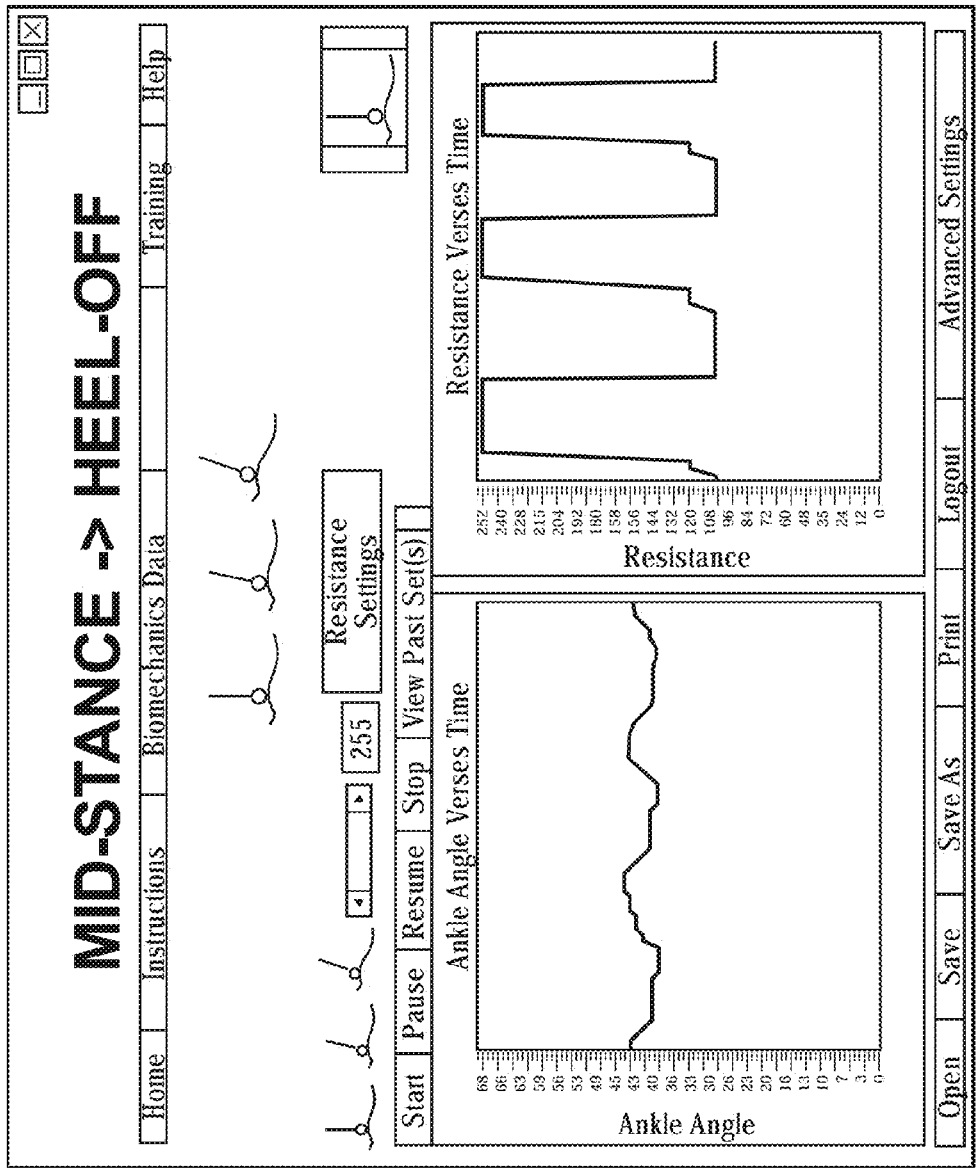
FIG. 36 is a general illustration depicting biomechanics data illustrated within a control program of actual movement of the device in real-time or past data.
Figure 37:
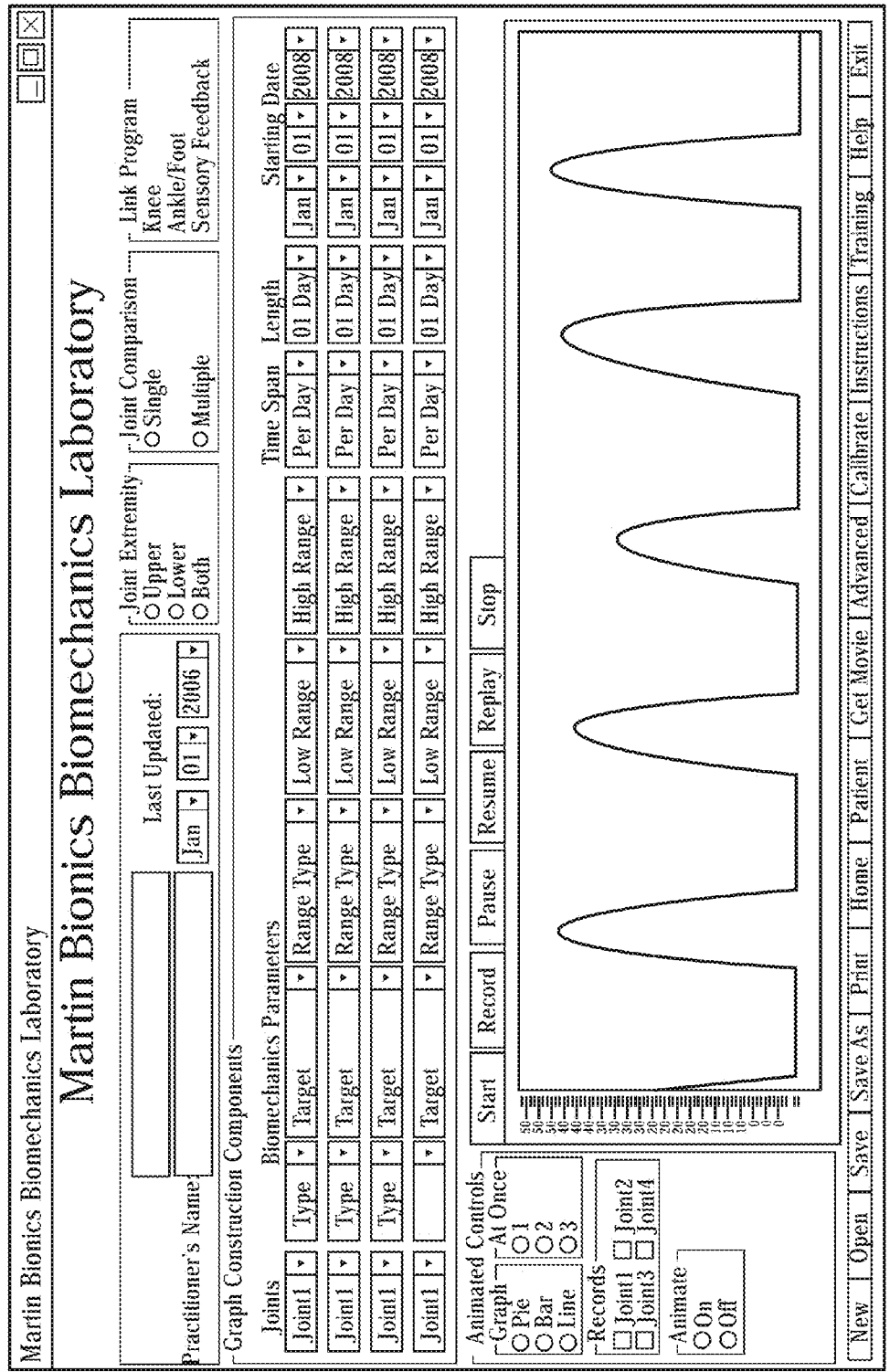
FIG. 37 is a general illustration depicting further biomechanics information that can be extracted from the device and displayed in various means and methods.
Figure 39:
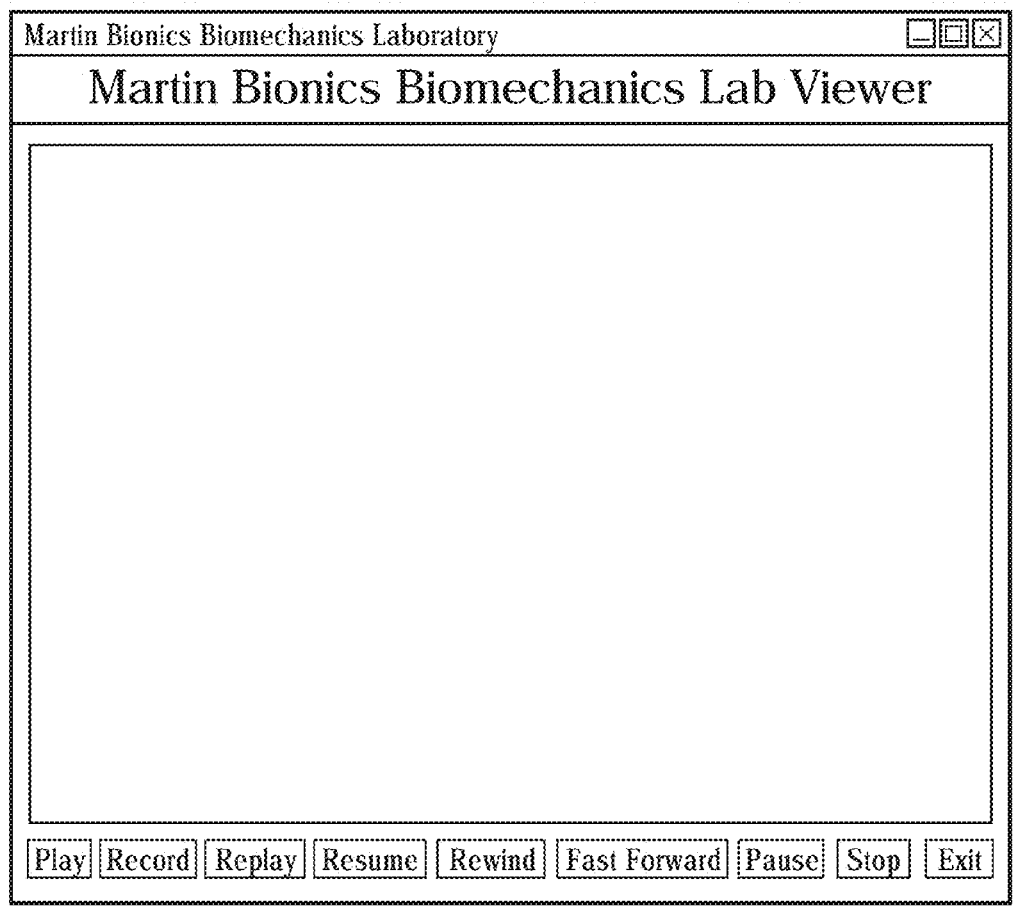
FIG. 39 is a general illustration depicting the ability to capture video, and video analysis of the user device's movement, which can be overlaid or viewed with other biomechanics graphical and pictorial illustrations.
Figure 40:
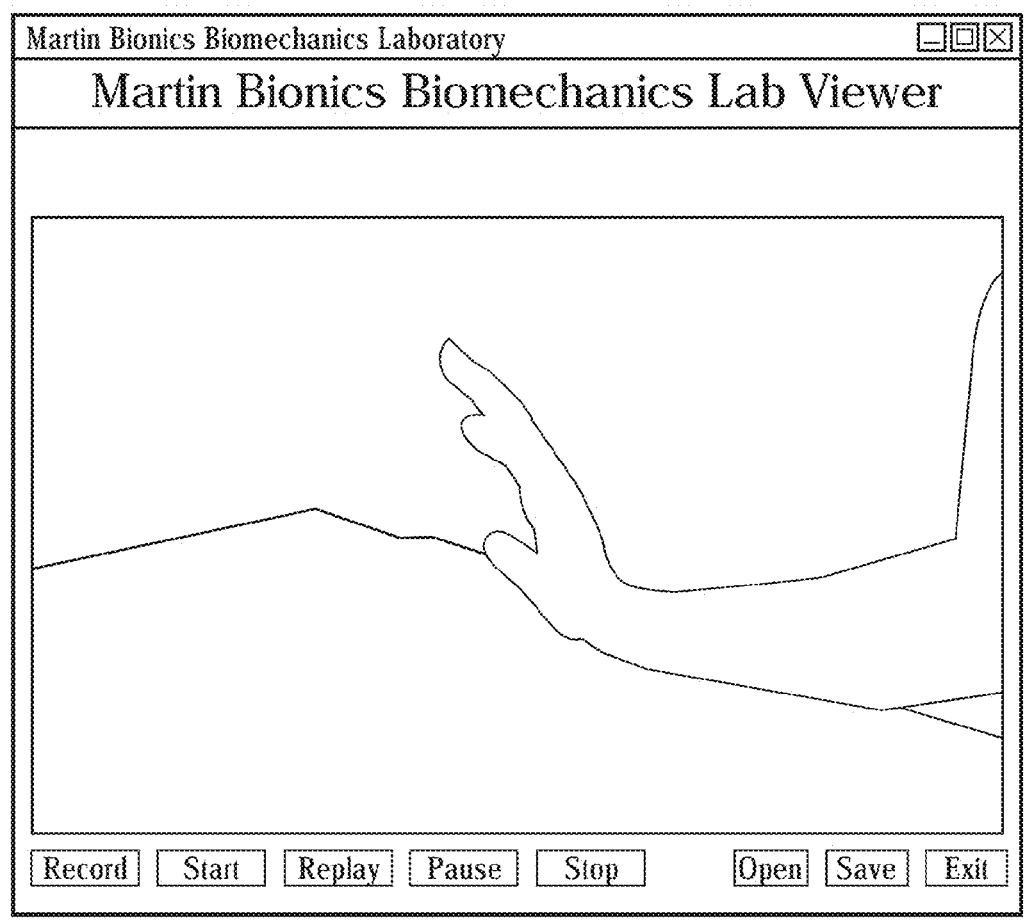
FIG. 40 is a general illustration depicting the ability to use virtual reality system in conjunction with the use of the device for training and control system, and system manipulation characteristics.

Still furthermore, the valve system may be controlled using pulse width modulation, as depicted in FIG. 32. Other methods of implementation may be used as well including but not limited to direct movement control, pulse code modulation, bi-phasic chopper drive controller, or other types of chopper drive controllers, current control, voltage control, modulated control, and others.

Compliance Control

It is further understood that mechanical and fluidly controlled systems often inherently have compliance and lag time associated with their functions. An associated control program may therefore account for such lag time or compliance in order to best suit the functions of mimicking gait biomechanics. This lag time enables for the processor to instantaneously make alterations to the end valve position, intending for a new fixed position of the valve, and rely on the slowness of such a valve to make it to that new valve position to provide a smooth transition of movement as the anatomical body would as well, for instance, have a gradual change in its state of resistance within a joint. It is understood though, that with faster mechanical or fluidly controlled systems with little to no lag time, the control program in general may provide a gradient to the valve position in order to "smooth" out the motion of the unit. It should as well be understood that the term valve should not be considered limiting but is used in general for explanatory purposes for those skilled in the art of robotics and prosthetics.

Calibration

It should be further understood that invention 10 may not require manual calibration of device for some sensor data. Instead, as the ankle joint, or other given joints associated with control program, goes through a given range of motion, the control program may set the maximum and minimum angles as end range points. If during ambulation, a greater or lesser angle is reached passed what may have already been established as an end range, the new value may take its place, establishing a new end range. Equivalently, other sensors, such as but not limited to force sensors, may provide their own input to the control program, microprocessor, or other, to set or initiate end range values.

Embedded Sensors

Because the use of numerous sensors in such a system may add cost and complexity, and lower durability and dependability, it is generally desired to use fewer sensors to control such a system, while maintaining consistency in control. In a preferred embodiment, the described control system may limit the associated control system sensors to an angle sensor, and force sensor, along with charting time with a real-time clock or alternatively similar device. It is understood that alternative sensors may be used, added, replaced with, or altered to provide similar outcomes, including but not limited to nanotechnology sensors, including carbon nanotubes, to determine force, force transition, temperature, pressure, vibration, or other information. In general, it is understood that sensors in general provide information to the microprocessor or other computer system to provide a "reaction" and affect the damper in a given way. Many various types or combinations of sensors may be used to provide similar outcomes. The described methods should not be considered limiting. Other types of sensors that may be utilized may include, but not be limited to, acceleration, gravity, magnetic, global positioning system technology in general, or others to provide a similar outcome as the described control program.

The described method of attaining appropriate information for the control program is through taking angle information to extrapolate angle, angular velocity, and angular acceleration information. Furthermore, a force sensor is used to determine if there is weight being applied to the foot, and in particular to the forefoot and/or heel regions. It is not necessary to have a highly calibrated force sensor, but rather to assess if there is weight being applied or not, especially at the forefoot region. This enables the sensor system to be more robust and less dependent on variations in sensor reading. It is further understood, however, that the precise information pertaining to the force data may be further assessed in biomechanics analysis, which will be further discussed below. Additionally, highly calibrated force data may be used to further accentuate the functions of the control program, or may be used to provide information to other joints, such as the knee or hip. Additionally, the use of multi-strain-gauge sensors may be used to provide force data in various planes to better control movement of the prosthetic, orthotic, or robotic system—which may include ankle, ankle and knee, ankle knee and hip, or other combinations thereof.

Still furthermore, force and/or torque data may be extrapolated from angle, angular velocity, or angular acceleration data, in possible conjunction with valve position data through mathematical equations. Because the control program sets valve position, it therefore has knowledge of valve orientation according to encoder or other sensor or electronics methods. Additionally, with known angle, and hence angular velocity and acceleration data, in conjunction with valve position data, other information such as force and torque data may be extrapolated through mathematical equations. There is a mathematical correlation between valve position, angular velocity/acceleration, angle, and other such parameters.

Furthermore, it should be understood that highly calibrated sensors may be used to assist the functions of the control program, but as sensors may fail, or provide faulty readings, the system as a whole may disregard the high calibration data set from the sensors and may rely on more general information from them, such as if weight is on the device or not. In such a system, and as may be used in general, the control program may look at sensor readings only above or between set thresholds in order to prevent stray or erroneous sensor readings from negatively altering the functions of the control program.

Still furthermore, it is understood that sensor data may be used in conjunction with other methods, equations, software, or the like, to extrapolate additional information such as but not limited to a method of maintaining the center of gravity of the device or user to be over the proper location of the foot via adjusting dynamically or passively the plantarflexion/dorsiflexion angle of the ankle, or resistance characteristics in general. This may require force sensor and/or angle information, amongst others to be analyzed to assess the force distribution, and force changing velocity in placement over the foot, gait cycle moments, and others.

Safety

In a preferred embodiment, numerous safety measures are constructed and programmed into the system. The below mentioned safety features are by no means exhaustive in nature. It is understood that numerous other safety measures are taken, which may or may not be described in detail, which are necessary to maintain sufficient reliable and safe use of the system.

In pertaining to the force sensor threshold in particular, control program should generally not allow the joint resistance, in particular ankle in this example, to substantially lessen if the force value on the device is above a designated threshold. This may assist in preventing the joint from too quickly loosening when the user intends for it to provide stability, and cause a fall.

Still furthermore, the control system may provide a limit to the speed, angular velocity, or angular acceleration of the joint movement during any or part of the gait cycle. In practical use, for instance, there may be an angle change threshold limit built in to provide a limit to the speed at which the angle is allowed to change according to the control program in order to maintain a more consistent transition from one state to another. This may be observed, for instance, after foot flat occurs, when weight is being applied to the foot. The ankle, in this example, may not be able to greatly, quickly, or otherwise largely lessen its resistance until the lower force threshold is crossed, allowing the device to then transition more quickly to its next determined stage, such as after toe off in transitioning to the swing phase of gait. This threshold may be set by the practitioner or patient, or may be pre-programmed into the system as a safety measure.

Still furthermore, through having an ankle joint that has the ability to accommodate for alterations in force, speed, and terrain, safety is even further improved. Through terrain accommodation for instance, as seen in FIG. 27A, the knee joint has inherently greater stability than what may be found in an ankle joint that does not appropriately accommodate for terrain variance, FIG. 27B. Similar benefits may be found for speed and force variations and accommodation through allowing the angle, angular velocity, angular acceleration, angular resistance, and other variables being most appropriate to best simulate natural biomechanics of not only the ankle joint, but also other joints such as the knee and hip.

Functions of Control Program

It is understood that the below explanations of the control system are to allow those skilled in the art of prosthetics, orthotics, and robotics to understand in detail what was submitted in the original patent application of this device. What is referred to as the DOUBLE HUMP GRAPH (though name should not be considered limiting, as the actual graph may not have two humps) that was originally illustrated in the patent application is characterized by the below descriptions. This further elaboration of explanation of that double hump graph is to assist those skilled in the art to understand its functions.

In a preferred embodiment, the control program should provide real-time control of the damper, correlated to force, speed, and terrain changes in the environment. This may be accomplished in many different ways. The below described goals and methods should not be considered limiting, but rather are illustrative of a possible method of implementation.

It is understood that the control program may work in conjunction with a prosthetic, orthotic, or robotic device to perform ambulation activities. It is further understood that for a prosthetic, orthotic, or robotic device, the control program may work in conjunction with an actuator system to control the general movement, force, speed, resistance, or other variables of the device or user. Still furthermore, the control program may be used in conjunction with active power actuation strategies to further enhance functional abilities of the system.

1. Alter Midstance angle with respect to force alterations. In a preferred embodiment, as force on the system increases, Midstance may occur sooner, in angle or time, to provide increased pushoff or spring return characteristics from the keel. It is further understood that force and speed of ambulation are highly related; hence Midstance position (angle or timing) may be altered according to speed of ambulation as well.

2. Alter Midstance angle with respect to terrain variations. Midstance may occur at a similar angle with respect to level ground no matter the terrain. It should be understood that the angle between the shin and foot may greatly alter for various terrains, but that the angle of the Midstance phase may be correlated to the terrain, whereas to provide a more natural Midstance resistance increase independent of the ambulated environment. As will be further discussed below, the foot may be able to have a compliant angular orientation to the terrain, while allowing a natural resistance of the ankle joint of the shin section at a natural angle corresponding to the terrain angle.

3. Alter valve position with respect to force. As the force increases for instance, the valve position closes more during heel strike or foot flat to midstance, midstance to heel off, and heel off to toe off, or whichever combination thereof that is relevant for the increase in force, in order to provide increased resistance to counter the force to maintain angular velocity near appropriate levels. When more of less force is applied that typical, the gait dynamics may additionally be purposely altered from normal ambulation characteristics by a certain factor or amount as will be accounted for in the equations below to better accommodate for necessary biomechanics alterations given the increased force. For example, as force increases, say when the user is carrying a heavy load, it may be preferable to allow the ankle angle to rotate during stance phase with higher angular velocity, angular acceleration, or a combination thereof, than with what would be found during normal ambulation. The converse of the same example may occur—with less force, and a more open valve position. The amount of alteration to valve position according to a given force amount may be predetermined, or learned through the control program.

4. Angular velocity may increase with increasing force, and decrease with decreasing force. As force may increase, and valve position closes more, it may be closed at an amount slightly less than necessary to maintain constant, similar, or adjusted angular velocity with respect to a normal force. This may be experienced, for instance, during running, when a greater force is experienced during the gait cycle, valve position is closed correspondingly to the increased force, but the final valve position may be altered slightly to provide a slightly higher angular velocity than would be tend to be experienced during normal walking, so as to better accommodate for a faster transition through the gait phase defining points needed in running. This may be a linear or non-linear function, and may be, in general, characterized by (constant angular velocity+function (angular velocity)). This may as well be characterized by the general function of N/X in the included equations.

5. The control program may as well offer a learning algorithm to adapt to the user over a longer period of time. Functionally, this may change the average angular velocity long term to effect midstance angle and valve position settings.

6. The control program may provide static and dynamic cosmetic benefits to the prosthetic system. The invention as a whole appropriately replicates biomechanics in all conditions and in all environments during dynamic movement—through accommodating for force, speed, and terrain changes. Additionally, the system offers plantarflexion during sitting, for instance, which results in a static cosmetic appearance that is more life-like than with conventional systems. Other custom tailored cosmetic related movements may be programmed into the system, which may or may not provide ambulatory functional significance, but that may allow for a more enhanced cosmetic appearance in general.

7. The control program may approximate or replicate normal angular velocity and general motion during ambulation throughout the various segments of the gait cycle, given no change in force, terrain, or speed. Functionally, the system will replicated the natural biomechanics of the specific individual's gait pattern. As described above, the system may also alter its angular velocity changes in order to accommodate for force, speed, and terrain changes. The control program settings may be manipulated by the practitioner or patient to provide a symmetrically equivalent gait pattern to the user.

Defining Points Definition

It is understood that there may be a plethora of variations or forms of noting the occurrences of the following descriptions of defining point definitions and therefore should not be considered limiting. Each of the gait cycle defining points occurs during normal ambulation, and the associated sensors, and their given combinations of data singly or in combination, may provide sufficient information to determine when, in time or angle, each of the defining moments occurs. The below descriptions may be used for general illustrative purposes to allow those skilled in the art to understand the general functions of the control program, and should not in any way be considered limiting.

In addition, in a preferred embodiment, when myoelectric or other central nervous system to prosthesis interaction takes place, signal analysis, EMG data, pattern recognition, or other similar methods may be used to determine intended movement, and therefore intended defining points during the gait cycle. It is understood that nerve or muscle signals may characterize intended movements of the limbs, and that information may be used to control the movement parameters of the prosthetic limb with enough definition to characterize the defining points. The following descriptions may illustrate a preferred embodiment, for little to no interaction with the central nervous system of the body, but alternative or complimentary approaches may be used as well as other neural signals may become available.

Direct Neural Control

Taking information from the user through sensors, versus solely through sensors in the device, may control the limb directly through direct neural control, or may control the limb through enhancing the functions of the control program, or a combination of both. Methods of capturing intended movement data from the body's central nervous system may provide information to the microprocessor, or its equivalent, which may allow for direct control of the prosthesis. In this case, the sensor or equivalent devices information may be provided to the controller. The controller may provide a predetermined or alterable correlation between the neural control data and the movement of the prosthesis, orthosis, or robotic device. As the user initiates a neural response for intended movement of the device, the device may exhibit that similar movement.

Heel Strike

Heel Strike may be defined by angular change in plantar direction, any time during the gait cycle, or during a selective period during the gait cycle. Alternatively, it may be defined by certain other timing, angular, or other ordered parameters.

Heel strike position 206 cushioning and invention 10 plantarflexion comes about mainly though true ankle plantarflexion and not simply through heel compression. It should be clearly understood that the control program detecting angular change in the system is functionally equivalent to detecting force, such as heel load or toe load forces because there is a correlation between heel or toe load forces, and angular change given a set valve position. The two terms therefore may be used interchangeably. While the heel portion of the keel 26 may compress slightly, the ankle joint assembly 16 plantarflexion will constantly be monitored to provide fluid, smooth, roll-over characteristics and provide optimal push off characteristics through keel 12 loading. As heel portion 26 load, moment sensor 192, or heel sensor system 174 or angular change sensor detect contact, foot plantarflexes with angle/time angular velocity using damper plantarflexor resistance. As the force of heel portion 26 contact increases, the damper resistance will increase to limit the force of plantarflexion and offer controlled plantarflexion.

It is contemplated that this will generally simulate the tibialis anterior essentric contraction in human biomechanics at and soon after heel strike position 206. Once the toe portion 34 load sensor 194 or toe sensor system 176 is greater than or near zero at foot flat position 208, the angle sensor 190 or sensor system 22 in general may predict angular change per time for heel portion 26 strike pressure sensor or heel sensor system 174. If angle/time is too slow, according to heel portion 26 strike pressure or heel sensor system 174, damper resistance decreases. This would generally correspond to the slowing down of gait speed. If angular change increases with respect to previous step (going down a hill for instance), damper may keep plantarflexing until toe portion 34 load sensor or sensor system 176 is greater than zero.

It is contemplated that invention 10 will generally adapt to the surrounding environment automatically, in order to maintain proper stability, safety, and function. A similar effect would occur if the user were wearing a high-heeled shoe. It should be noted that at heel strike position 206 with many other prosthetic feet designs, the plantarflexion movement is obtained through heel compression. In a preferred construction, invention 10 may allow slight compression for shock absorption and smoothness of gait, but just as occurs biomechanically, the plantarflexion movement occurs through the ankle joint assembly 16 movement with an eccentric contraction of the tibialis anterior and not necessarily entirely through heel compression. It is contemplated that, the dampening system 18 allows for the controlled plantarflexion, mimicking the tibialis anterior movement, while the heel or heel portion 26 compression may mimic natural heel fatty pad compression for general shock absorption.

Foot Flat

Foot Flat may be defined by an angular direction change from plantarflexion to dorsiflexion. Alternatively, it may be characterized by certain other timing, angular, or other ordered parameters, such as but not limited to when toe load force exceeds set value.

With increased heel sensor 174 pressure or angular velocity during heel strike position 206 to foot flat position 208, damper dorsiflexion resistance may increase from foot flat position 208 to midstance position 210 in order to provide increased plantarflexion during later portions of gait to allow increased spring off from invention 10 from heel off position 212 to toe off position 204. This may mimic the action of the gastrocnemious muscles during walking.

Mid Stance

Mid Stance may be defined by taking the average angular velocity experienced from heel strike to foot flat, subtracting the average angular velocity historically from heel strike to foot flat. Dividing that sum by X1 degrees per second. Multiplying that sum by N1. Adding to that the sum of the Foot Flat angle experienced minus the Foot Flat angle level ground plus the Mid Stance GUI setting. The Foot Flat angle level ground may be a GUI set parameter or may be self-learned through the control program, or a combination of both. The Foot Flat angle experienced may be the angle that Foot Flat occurs. This may be corresponding to the Foot Flat angle level ground plus the terrain angle. Furthermore to illustrate, in a preferred embodiment, what X1 and N1 are: For every X degrees per second difference in average angular velocity experienced between heel strike and foot flat for instance, minus average angular velocity historically between heel strike and foot flat for instance, change angle of Mid Stance by N degrees. This should functionally be a relatively small number. This equation accounts for both changing Mid Stance according to force alterations as well as terrain alterations. Each component may be used in conjunction with the other, or independently.

The term average angular velocity experienced between heel strike and foot flat for instance should not be considered limiting, and may be replaced by other sensor data to provide similar function.

Average angular velocity historically between heel strike and foot flat for instance, may be characterized by taking $\alpha(\omega 1(i-1)+(\alpha-1)Avg\ \omega exp\ (HS-FF)$, where $\alpha$ equals the factor of length of average decreasing, $\omega 1$ equals the average angular velocity historically from Heel Strike to Foot Flat for instance calculated previously, i equals current step, and (i−1) equals previous step.

It should be clearly understood that there are a number of mathematical methods of characterizing an average from a set of data, and what is being described is meant for descriptive purposes of how an average may be calculated for a given set of data for use in prosthetics, and should not be considered limiting. There are a number of alternative methods of calculating an average such as but not limited to taking the sum of values, and dividing by the number of values. In such as case, each value may have a relatively equivalent significance in correlation to the others. Equivalently, taking a random set of values, or equally spaced values (one out of every 1000 for instance) from a sequential list of values may be used to capture the data set for taking the average as well, amongst other methods. Methods as described in taking a moving or sliding average may be used to, in real-time, characterize the most appropriate characteristics of the user's gait pattern. Additionally, taking a non-linearly characterized significance of the values in a data set for taking an average may be used to better define short term or long term necessary alterations in the gait pattern as controlled by the control program. For instance, the user may gain weight over a several month period, and the average angular velocity historically value may be altered to account for that weight change. Additionally, a secondary component to the above equation may be used to characterized short term alterations such as if the person begins to run, and therefore the shorter term sliding average may account for altering the gait pattern characteristics based off of the most recent steps data set.

Still furthermore, the general control equations should not be considered limiting, as they depict one variation of illustrating such control parameters. Terms such as heel sensor system for instance, amongst others, should not be considered limiting, and can be illustrated in various embodiments such as but not limited to strain gauge(s), calculated force value out of other sensor input(s), or other force related sensor values.

With increased heel portion 26 sensor pressure or generally indication from heel sensor system 174 or angular velocity during heel strike position 206 to foot flat position 208, damper dorsiflexion resistance may increase to provide increased plantarflexion during gait until toe portion 34 load sensor or toe sensor system 176 equals zero during toe off position 204, or angular velocity equals zero, given open valve position. It is contemplated this may allow slight dorsiflexion to a certain angle for smoothness of gait but may remain in some plantarflexion for push off from heel off position 212 to toe off position 204. During this section of gait, the dampening system 18 may lock out to provide the necessary plantarflexion for push off; however, the angle which the dampening system 18 of ankle joint assembly 16 may lock out will vary according to angular sensor 190, heel load sensor 192 during heel strike 206, and angular velocity determination, etc. It is further contemplated that the system may not fully lock out the damper, but rather, may provide a sufficiently stiff system in order to provide only minimal angle change. During this portion of gait, the invention 10 may go into some dorsiflexion, however, the dorsiflexion is obtained in a preferred embodiment through keel 12 loading and some ankle joint bending, therefore leading to increased push off at toe off position 204.

Functionally, through the above equations, midstance may be set at more or less angle with respect to what may be otherwise observed, given a change in force per step, as well as through changes over a longer period of time. This may use a multiplying factor not provide a non-linear relationship between force changes and produced angular velocity changes from normal ambulation. Additionally, midstance may change in angle corresponding to terrain.

Heel Off

Heel Off may be characterized by a GUI setting of p degrees past Mid Stance and may include other sensor information such as with toe pressure above threshold. Utilizing data such as toe pressure above threshold may be used to prevent the system from accidentally becoming too instable for the user while weight is being applied. It may also be characterized by a set time past Mid Stance, or force past Mid Stance. Alternatively, it may be characterized by certain other timing, angular, or other ordered parameters.

In natural human locomotion, the plantarflexor muscles fire at this stage in the gait cycle to maintain ankle angle or provide slight plantarflexion for push off. It is contemplated that through invention 10, the plantarflexion is already obtained through the midstance phase of gait and having the dampening system 18 lock out or near lock out at a preferred or certain angle; however, it has been stored through keel 12 loading and is released in spring off from heel off position 212 to toe off position 204 thus simulating gastrocnemious induced plantarflexion of the foot.

Toe Off

Toe Off may be defined by when force experienced on the system dropping below a certain threshold. Alternatively, it may be characterized by certain other timing, angular, or other ordered parameters.

After heel portion 26 load sensor 192 equals zero and/or toe portion 34 pressure sensor approaches zero or a set threshold, or angular velocity with valve position is such that force is near zero, damper resistance goes to zero, or other low damper resistance setting and allows for dorsiflexion spring system 137 to dorsiflex foot during swing phase.

Equivalently, an active powered system or augmented powered system may be used to assist in foot and ankle dorsiflexion.

Generally referring to FIG. 13, as the user completes the toe off position 204 of the gait cycle, the dorsiflexion spring system 137, or complimentary dynamic alteration of joint angle may cause invention 10 to immediately begin to go into dorsiflexion, as occurs in normal human locomotion, to decrease the likelihood of stubbing the toe portion 34 during swing phase of gait. The term dorsiflexion spring should not be considered limiting, and in general, describes a method of passively or actively adjusting the ankle joint into dorsiflexion. Once full or predetermined swing phase angle occurs, resistance of dampening system 18 remains at or near zero or other predetermined valve setting, to maintain angle or angular change, until heel strike position 206 when heel sensor system 174 detect pressure or load greater than zero, or angle change is in plantar direction. The rate of dorsiflexion angle change can be programmed to allow for optimal safety and symmetry through varying the valve position.

The spring load resistance of dorsiflexion spring system 137 may be modified or changed through adjusting the spring drive length, changing to a lighter or heavier spring, altering the dorsiflexion actuation characteristics in general, and/or through increasing dampening system 18 resistance, in order to optimize this characteristic for the user's activities. Furthermore, dynamic movement of the dorsiflexion system may be adjusted through software, mechanical, fluid dynamics, or other means. By example, if the user intends to run, the dorsiflexion spring system 137 resistance characteristics may be increased to overcome the inertial effects of the invention 10 during running. This may be automatically accounted for through the control program or through externally adjusted means. Still furthermore, the dorsiflexion spring or method may work in a compressive or extension orientation, and may actively pull or push the device into dorsiflexion.

Throughout swing phase, invention 10 may remain in dorsiflexion until heel strike position 206 in order to generally shorten the extremity.

Furthermore, for midswing detection—this may use information of when toe off occurs, quickly bringing system into dorsiflection at a predetermined, or alterable rate. Can also use predetermined valve position of swing phase, compare angular velocity of device once in that valve position to what is typically found, possibly through an averaging mechanism, and alter the valve position accordingly to enable the foot to dorsiflex faster or slower. If the user is running for instance, the pendular effects of the foot may limit its ability to dorsiflex, so the angular velocity of dorsiflexion is too slow, and valve position opens up, and allows for it to dorsiflex faster. This provides a variable swing phase control. Can also use angular velocity within a certain timeframe within the beginning of the swing phase and then alter after that given time frame. Then, look at new angular velocity with new valve position, and compare to predicted or preferred angular velocity. System may store that value and use it to alter the "intended" angular velocity over time. It may learn the user's walking style. For instance, if the ankle is set it to dorsiflex at a certain rate, and the user begins to walk harder or faster and the foot is dorsiflexing too fast, the valve position may change during the step to slow it down, but if that still doesn't slow it down enough, system may learn to put valve position a little further to slow it down further next time—predicting gait style.

Valve Position Settings

Heel Strike or Foot Flat to Toe Off valve position settings may be calculated by taking the average angular velocity experienced between heel strike and foot flat for instance, minus the average angular velocity historically between heel strike and foot flat for instance, and dividing that by X2 degrees per second. Then multiplying that value by N2 and adding GUI valve position setting for HS, FF, MS, HO, or TO, given the gait cycle phase.

Equivalently, this may be characterized as well by taking Heel Strike or Foot Flat to Toe Off settings by taking the average angular velocity experienced between heel strike and foot flat up to current moment in time or angle for instance, minus the average angular velocity historically between heel strike and foot flat up to current moment in time or angle for instance, and dividing that by X2 degrees per second. Then multiplying that value by N2 and adding GUI valve placement setting for HS, FF, MS, HO, or TO, given the gait cycle phase.

Equivalently, force sensor information may be used to determine valve position setting from heel strike to toe off, and from toe off to heel strike. Even more, neural input from the user to the prosthesis may be used to characterize valve position setting during ambulation.

Functionally, the provided angular velocity of the angle change may be altered according to force, whereas force increases, the angular velocity may be allowed to increase during portions of the gait cycle in a linear or non-linear manner. This may be accomplished by opening or closing valve position more or less corresponding to sensor data of force, speed, or other measurable parameters.

Standing Up

When a user begins to stand, the control program may realize that weight is being applied to the foot, the foot may be moving in the plantarflexion direction, or begin to move in the dorsiflexion direction, in which case the resistance will inherently increase. Functionally, this provides increased resistance on the toe portion of the prosthetic, orthotic, or robotic system, and inherently provides increased knee extension moment. This may be beneficial to a variety of users who suffer from poor balance or knee stability or strength. For an above the knee amputee for instance, this will greatly assist in providing stability and safety when going from a sitting to a standing position.

The amount that the foot goes into dorsiflexion upon standing may be customized in the GUI settings, and the control program may use various timing and sensor information to analyze that the user was in fact sitting, and is now attempting to stand.

Alternatively, the system may allow for slight dorsiflexion during this time in order to allow the user to get their weight underneath them more to better assist in standing. Through the GUI settings, the practitioner skilled in the art may be able to customize this parameter to the user.

Stumbling

The control program may as well determine that a user is stumbling through sensor input to the device, such as but not limited to having an other than normal sequence of gait defining moment events, and may accommodate for stumbling actions through determination of other sensor signals, and may generally dorsiflex foot during swing, move other joints such as knee or hip into general angle or with general force, provide increased resistance to device upon contact, or other. This may advantageously be used to predict intended movement to provide stability.

Dynamic Data Capture for Control System

Additionally, the control program may use dynamic or static roll-over characteristics data to help determine ankle, knee, hip, or any combination thereof, movement. Additionally, this information may be used to custom fabricate the structural members, such as the keel, and others, to best tailor to the user. This data may come from the user's sound side, or from a donor's gait cycle data, or a combination of both. This information may be further utilized to determine foot size, shape, and other characteristics to determine how much dorsiflexion, for instance, the system may go through from foot flat to toe off. The control program may use this data to emulate the natural roll-over progression characteristics, including but not limited to heel, ankle, and forefoot rocker dynamics. Furthermore, the system may utilize a combination of GUI settings, control program equations, and sound side gait data to best tailor the specific movements of the prosthetic side to match the sound side. This may come about through wearing the sensors on the sound side during ambulation on the prosthesis, or may come about through data capture from the user's sound side and then importing that data to the prosthesis for control or movement alterations thereof.

Still furthermore, the data captured from the sound side foot may be used to determine layup characteristics (thickness, stiffness, etc.) of the prosthetic keel. It may as well be used in the fabrication process, including rapid prototyping of the form to make the keel, as well as to possibly make the keel itself. The general attachment method of the keel to the ankle device may be standard so that all custom keels may match to the ankle unit. It may be important to provide custom keels to the user because the foot plantar surface characteristics, including arches, surface area, rockers, and other characteristics influence the gait dynamics.

Research may then be done on the performance and gait analysis of an amputee walking to compare differences in sound and prosthetic side gait. This may help to further refine the system to best match the user's optimal performance.

In one embodiment, the controls may be implemented using multiplex operation of joint actuators. The system may consist of a control board and a multiplexer board. The control board may send address signal to multiplexer board to enable/disable ground place of each actuator. The feedback (which may be deflection amplitude) may then be connected to control board. Each motor may be connected in series or parallel with the control board. The driver and on/off signals for the motors may be generated through a field programmable gate array. The driver circuit may use a push pull converter consisting of gate driver, power switches, and transformers. The control board may use a microcontroller or a microprocessor. The control parameters may be changed using a graphical user interface using Matlab, Labview, Visual basic, or any other graphical or non-graphical programming environment. The filter design may have 1 KHz cutoff frequency or other frequency ranges. For high speed data-bus a serial SpaceWire protocol may be used or other similar forms. For switching power to the actuators, FETs may be used. For reversing the direction of motor a speed profile may be used. Different levels or frequency/amplitude may be used to finely control the speed and reduce the power requirement when moving the coordinated joints.

Thermal Viscosity Alterations

The issue of changing thermal viscosity may be inherently resolved through the portion of the control program equation of average angular velocity experienced from heel strike to foot flat for instance because in such an equation the average angular experienced is changing with respect to viscosity and hence altering valve position setting to counter the fluid being more or less viscous than when programmed originally. Alternatively, an additional equation may be added with a smaller population pool in taking the average to take a new average over recent steps only to account for viscosity changes to the fluid. Still furthermore, additional sensor system(s) may be incorporated into the device to asses fluid viscosity or temperature, and allow the control program to account for that change accordingly.

Further Equation Definitions and Methods

Figure 26:
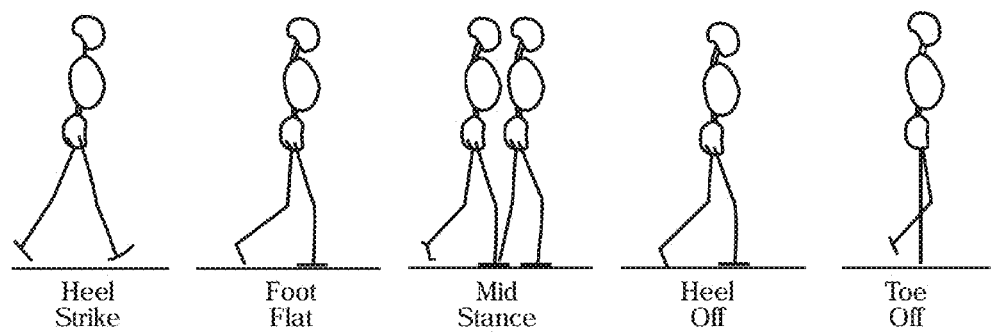
FIG. 26 is a general illustration depicting the various phases in the gait cycle.
Figure 27:
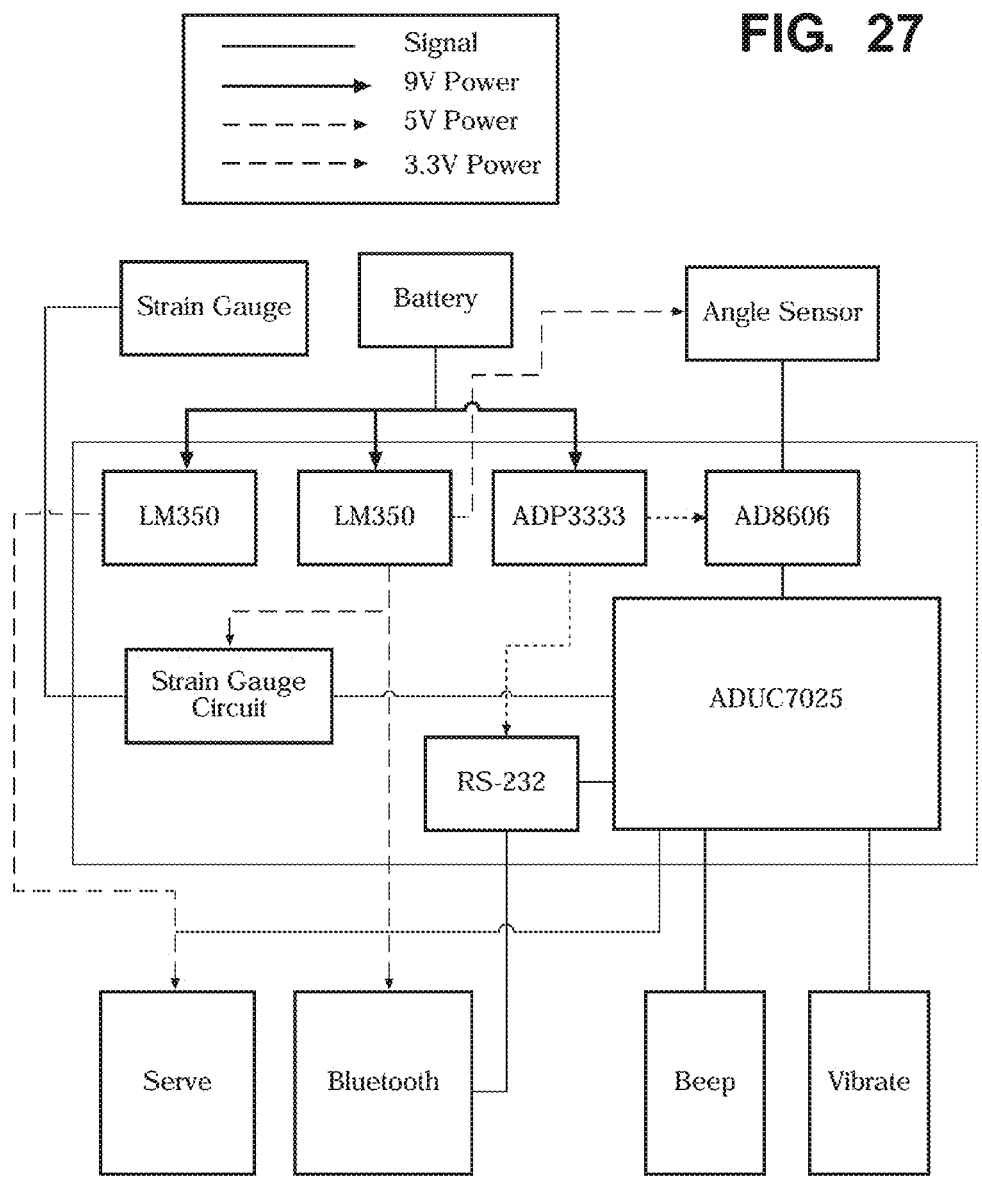
FIG. 27 is a general illustration depicting one embodiment of block diagram of system electronics.
Figure 28:
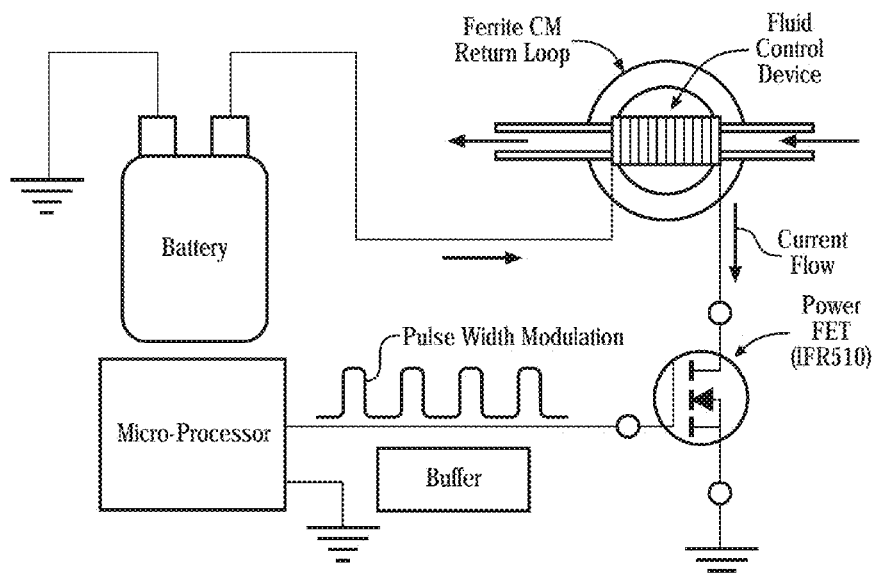
FIG. 28 is a general illustration depicting one embodiment of block diagram of system electronics and how they relate to the valve system.
Figure 29:
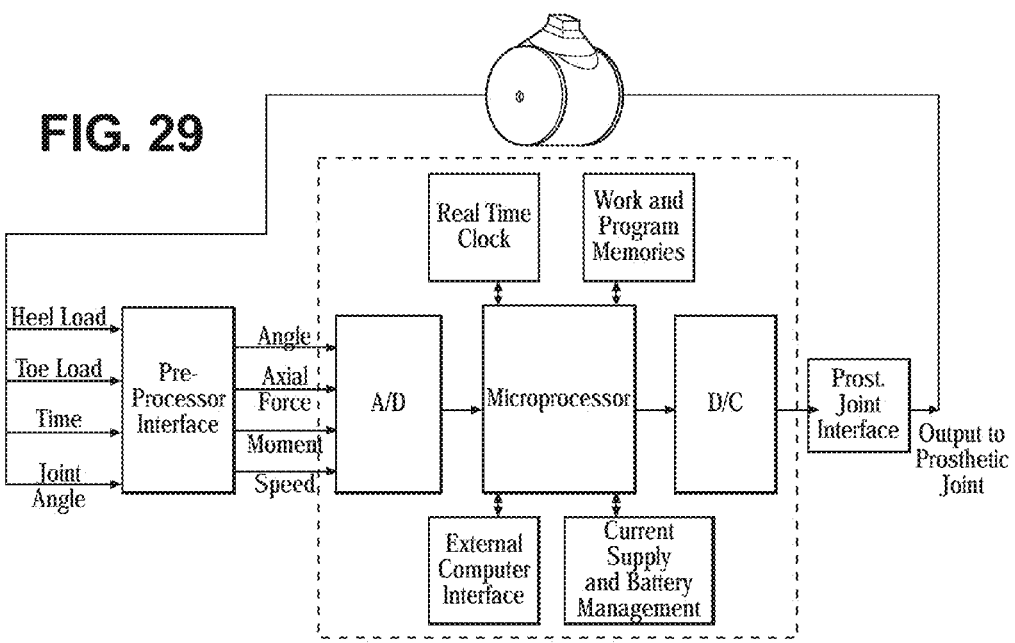
FIG. 29 is a general illustration depicting one embodiment of block diagram of system.

Furthermore, control system equations and data, including gait cycle defining points as illustrated in FIG. 26 may be depicted as, but not limited to the following:
Equations:
Mid-stance angle calculation $$\theta_{Ci} = \frac{N}{X}[\omega_i - \omega_a] + \theta_{Ei} - \theta_L + \theta_M$$

Foot-flat to Mid-Stance damping calculation $$B_{ffi} = \frac{N}{X}[\omega_i - \omega_a] + B_{FFU}$$

Mid-Stance to Heel-off damping calculation $$B_{MSi} = \frac{N}{X}[\omega_i - \omega_a] + B_{MSU}$$

Heel-off to Toe-off damping calculation $$B_{HOi} = \frac{N}{X}[\omega_i - \omega_a] + B_{HOU}$$

DEFINITIONS $\omega_i$=Peak angular velocity from heel-strike to foot-flat during one gait cycle (i)
$\omega_a$=Average peak angular velocity from heel-strike to foot-flat
m=Number of gait cycles for averaging
X, N=User constants
$\theta_{Ei}$=Foot-flat experienced during one gait cycle
$\theta_L$=Foot-flat level ground user setting
$\theta_M$=Mid-stance user setting
$B_{FFi}$=Foot-flat to Mid-stance damper calculation during one gait cycle (i)
$B_{FFU}$=Foot-flat to Mid-stance damper user setting
$B_{MSi}$=Mid-stance to Heel-off damper calculation during one gait cycle (i)
$B_{MSU}$=Mid-stance to Heel-off damper user setting is indicated as
$B_{Hoi}$=Heel-off to Toe-off damper calculation during one gait cycle (i)
$B_{HOU}$=Heel-off to Toe-off damper user setting
Notation: Plantar direction is defined as positive.
Gait Cycle Indicators
  Heel strike event—negative to positive (plantar) direction change
  Foot flat event—positive to negative (dorsal) direction change
  Mid-stance event—Occurs on reaching the calculated mid-stance angle
  Heel off event—Occurs on reaching the user specified angle forward of mid-stance
  Toe off event—Occurs on losing toe force
    a. Non-gait indicators
  Toe-load—toe force used as indicator for toe-load at which time the prosthetic is required to prevent falling
  Heel-strike—used in other gait stages to indicate a new gait cycle beginning Still furthermore, FIGS. 30, 31, 32, 33, and 34 generally may depict possible preferred embodiments of control system flow diagrams and general methods of functioning, but should not be limited to such.

Furthermore, the force sensor, for the control system function, may simply be utilized as an on/off switch to determine if force is on the foot or not. Additionally, other sensors may be used instead to provide contact information only.

Still furthermore, sensor signals may be filtered to produce more usable data. Additionally, for use in historic biomechanics data capture, the use of autoregressive, moving average, autoregressive moving average, autoregressive integrated moving average, low or high pass, other regressive methods such as but not limited to linear, quadratic, exponential, harmonic, ordered polynomials, or other methods may be used.

The defining moments may as well occur in other than normal orders in a preferred embodiment, and is not dependent on using sequential defining points order for proper function.

Electronics

Figure 30:
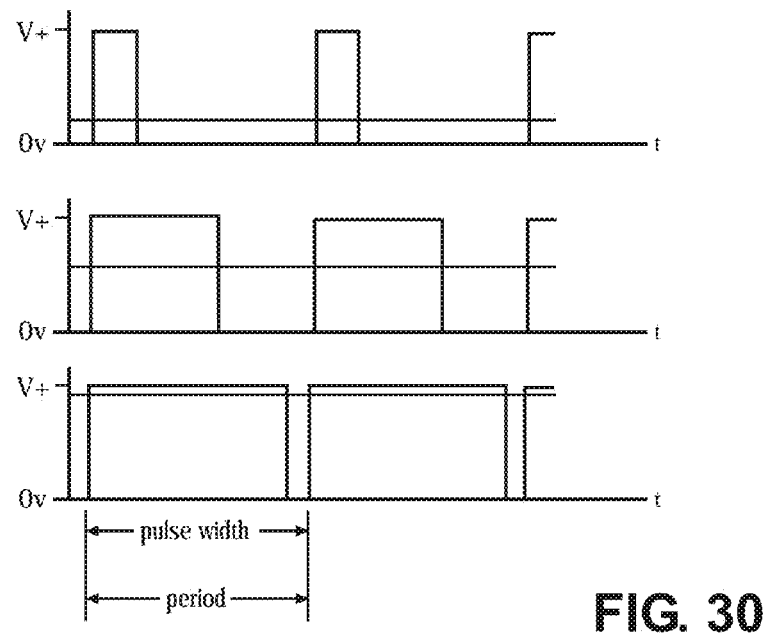
FIG. 30 is a general illustration depicting pulse width modulation.
Figure 31:
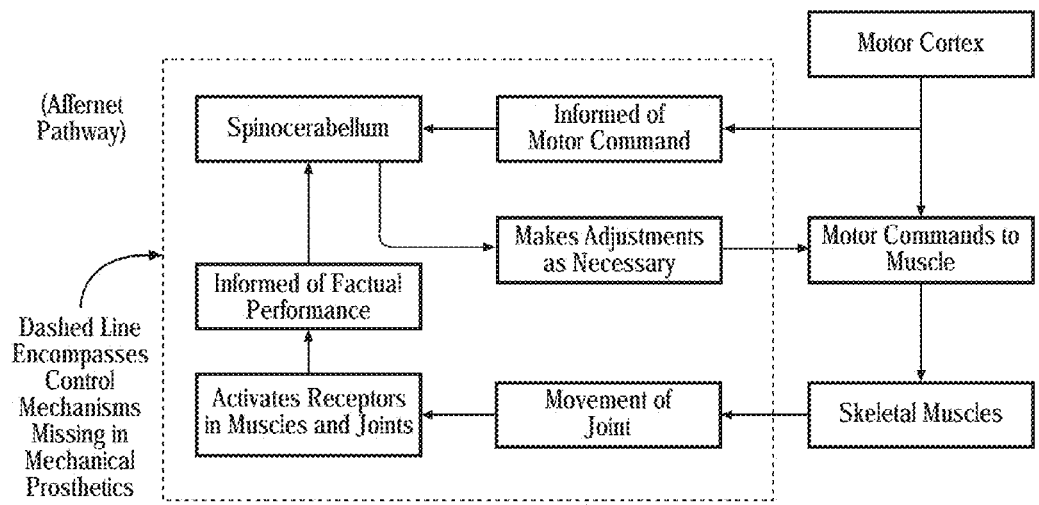
FIG. 31 is a general illustration depicting physiological sensory feedback loop and what is missing in conventional prosthetic systems.

The electronics flow chart diagrams, and general methods of implementation may be illustrated by the FIGS. 30, 31, and 32 but should not be considered limited to such. Other illustrations and embodiments are conceived as well, not departing from the spirit and scope of the disclosure.

Modular Robotics

In a preferred embodiment, the functional characteristic of a computer controlled prosthetic, orthotic, or robotic ankle or foot may work in conjunction with other joint such as a knee and/or a hip, but not limited to such. Each of the joints that are developed may have the ability to function alone or independently from others when necessary, but may as well be able to function in conjunction with other joints to provide enhanced control or functions. Any communication that may take place between various joint may be through wires or wireless means.

Furthermore, a computer or electronically controlled joint system may as well utilize an array of various control programs, specifically characterized for given patient needs. For instance, some users of the prosthesis will have the functional ability to do little more than transfer on the prosthesis, orthosis, or robotic device, or even possibly walk with assistance, while others may be very active and transverse ramps, barriers, stairs, or other activities with ease and stability. It is contemplated that the mechanical characteristics of the specific joint may be equivalent or similar for many users, such as range of motion, resistance range (fully locked to fully unlocked for instance), and others, while the functional characteristics such as but not limited to control methods, stability requirements, assistance methods, augmented power levels, and other parameters may be modularly altered according to the user's needs. In such a case, the type of specifics of the control program may be specified in order to allow the specific user to have optimal biomechanics, stability, safety, ease of use for certain activities, or other adjustable reasons. Still furthermore, the use of communication in general of or between various joints may further add to the functional benefits of given users.

It is contemplated that the functional parameters of a prosthetic knee for instance may be correlated to information based off the foot or ankle parameters to enable the knee to function in a more preferred method. Equivalently, the hip function may benefit from information based off of ankle and/or knee information.

Still furthermore, a prosthetic, orthotic, or robotic knee or hip joint may as well encompass the equivalent or similar electronics, circuit designs, control programs, control parameters, communication system, neural input methods, including pattern recognition, to control or use such a device. It is contemplated that the usage of such described systems in a knee or hip are considered equivalent and complimentary to an ankle mechanism, and should not be considered limiting, and should be considered as one and the same as the ankle illustrations and methods of such a device.

Alterations from Normal Ambulation Function Plantarflexion in Sitting

A common complaint of many prosthetic foot users is that their prosthetic foot "sticks up" when they sit. This uncosmetic appearance is eliminated through invention 10 by allowing the prosthetic to lose all or much of the plantarflexion resistance when the user is sitting, thus, allowing the foot to be at a natural angle. In a preferred construction, it should be noted that the dorsiflexion spring system 137 should not provide too much resistance to plantarflexing as to prevent the necessary motion in sitting, or to alter the gait pattern negatively. During sitting, it is contemplated that the dampening system 18 may prevent dorsiflexion while allowing plantarflexion to be free in order to provide greater cosmetic appearance. The sensor system 22 (time, angle, moment, etc.) may determine if the user is sitting and will correspondingly allow invention 10 to plantarflex.

It is also contemplated that heel pressure, as generally determined by heel sensor system 174, that occurs for a given time period such as a few seconds, with no toe pressure, as generally indicated by toe sensor system 176, may indicate or allow plantarflexion for sitting wherein little to no resistance is created. Still furthermore, sensor system may allow, during sitting, for the foot to naturally plantarflex with heel strike to foot flat resistance setting, until sufficient toe pressure is reached, and may in general prevent the foot from dorsiflexing until the requirements for doing so are met as would be found during ambulation. This as well may provide increased stability during standing back up or to provide increased knee stability for use in a transfemoral or hip disarticulation level amputation.

Still furthermore, the plantarflexion characteristics of the foot during sitting, and standing may be actively altered through a powered system in real-time, as necessary to provide optimal stability and safety for the user.

It is further contemplated that a negative bending moment on the heel portion 26 could signal the microprocessor unit 172 that the user has sat down and to have free plantarflexion abilities. A preferred embodiment may be by planting the heel portion 26 into the ground after sitting and pulling back. This action would generally not occur in normal walking and may therefore be a sufficient indicator for sitting action. Other methods of actuating plantarflexion in sitting may be used as well.

Heel Height Adjustment Accommodation

In a preferred construction, invention 10 is constantly updating the sensory feedback system 22 information to the microprocessor unit 172 wherein the user can change heel heights of a shoe without changing any settings. If the user goes to a higher heel height for instance, the sensors system 22 will still read the moment forces and consider that the user is equivalently merely walking down a hill and, thus, the gait of the user will not significantly alter, for instance. In this case, the ankle joint's angle and timing of resistance is appropriately matched to the sound side's movement. The dampening system 18 can further be designed to allow a certain amount of heel height clearance accommodation. It is contemplated to allow about 15 degrees of dorsiflexion and about 45 degrees of plantarflexion to allow proper natural human locomotion and to allow for heel height changes. It is further contemplated that more or less degrees of rotation may be desired to allow for more or less of a range of motion to achieve natural human locomotion. It is understood that natural human locomotion may be altered or generally defined by such things as a user's desire or need to wear higher or lower heeled shoes.

In a preferred embodiment, invention 10 may have special modes to allow the user to lock the keel 12 or joint assembly 16 out at a given angle, such as for skiing, or can change the characteristics for other specific activities where limited motion is required. It is understood that various methods of implementing such is contemplated. Still furthermore, the use of inherent compliancy built into the system, may provide for a more natural feel during such activities.

Stumbling or Walking Up Steep Hill

If toe load sensor 194 is greater than zero before heel load sensor 192 is greater than zero, then damper resistance may remain at or near zero or may fully lock up to stabilize joint assembly 16 if not fully dorsiflexed already, to continue to allow for full dorsiflexion via dorsiflexion spring system 137. In walking up a hill, this movement would still be similar to natural human locomotion and may benefit the user by decreasing or reducing hyperextension of the knee, as is found in the prior art. The use of active powered, or augmented powered system may as well be implemented to provide alterations to the plantarflexion or dorsiflexion state for such activities, such as but not limited to altering the ankle angle during such activities.

Walking Down Hill

As angular sensor 190 determines that there is a greater angular change since heel strike position 206 and foot flat position 208, wherein toe load sensor 194 maybe greater than zero, invention 10 may provide slightly less dorsiflexion resistance from heel off position 212 to toe off position 204 to allow the user to descend downhill according to proper natural human locomotion. The use of active powered, or augmented powered system may as well be implemented to provide alterations to the plantarflexion or dorsiflexion state for such activities.

Going Up Stairs

It is understood that generally a foot will already be in dorsiflexion after previous step and may remain in dorsiflexion as the stairs are ascended. Of note, invention 10 may or may not provide active push off during ambulation, on each step, providing the optimal keel 12 angle to enhance push off characteristics during gait. Thus, invention 10 generally may allow for the greatest anterior support and energy return per walking speed and environment.

In going up stairs, biomechanically, active push off is achieved with gastrocnemious muscle activity. It is contemplated that invention 10 may be modified within the scope of the claims and description such that a generally heavier design with increased power output consumption may generally simulate the natural muscle activity in this action. In such a case, the use of active powered, or augmented powered system however may as well be implemented to provide alterations to the plantarflexion or dorsiflexion state for such activities.

It is further understood that in ascending stairs, the foot naturally goes into dorsiflexion for the first half of the ascent. A separate setting may also be included or programmed whereas the user may place the invention 10 in "stair ascent" mode to allow slight plantarflexion or, if preferred, less dorsiflexion, or similarly, active powered actuation through a range of motion.

It is understood that during stair ascent, the foot contact is made in some dorsiflexion, of which the foot is already in dorsiflexion during the swing portion of the gait cycle. The foot may then be allowed to continue into increased dorsiflexion at a set or variable dorsiflexion rate according to other sensor data such as but not limited to heel off sensor, angle sensor, or others. This biomechanical action is required for proper motion during stair or hill ascent. Toward the end of the step, the foot may go into powered plantarflexion, in accordance with spring or powered actuation strategies.

Going Down Stairs

It is contemplated that if heel sensor 174 load or strike sensor 192 is greater than zero two steps or times in a row and no toe sensor 176 load or strike is observed, resistance in damper may increase at foot flat position 208 angle to prevent full plantarflexion and slipping off step. Still furthermore, as with the other ambulations generally described above, microprocessor unit 172 may be calibrated specifically for a user after a test run, sample, or base line is established of user performing the ambulation in an optimal manner. It is contemplated that by allowing the foot to plantarflex, invention 10 may improve ambulation in descending stairs. The use of active powered, or augmented powered system may as well be implemented to provide alterations to the plantarflexion or dorsiflexion state for such activities.

During stair descent, the foot may be put into plantarflexion prior to ground contact through neural integration strategies, sensor input, powered actuation methods, or environmental feedback, amongst other methods, and then provide resistance to dorsiflexion upon contact. Additionally, it may provide powered plantarflexion during the step.

Graphical User Interface System

In a preferred embodiment, custom tailoring of the dynamic characteristics of the prosthetic system may be produced through a graphical user interface system, or the like. This system may encompass a computer based software for a desktop or laptop computer, it may be software that is managed through a cell phone or PDA, it may be accessible through a handheld electronic device or key fob, or may be managed through another form of electronic user interface. The above description is not meant to be considered limiting in any way, but rather, generally illustrates possible interaction methods of the user to the prosthetic device from a setting perspective.

Who Has Access

The user interface may include the ability for the practitioner, patient, or others to alter the state of the device in numerous ways. It is conceived that practitioners and patients may each have their own unique set of possible adjustments. This may allow the practitioner to have complete access to system variables, while the patient, for instance, may have a limited set of adjustable variables. It may benefit the patient by allowing them to more finely custom tailor their prosthesis to meet their individual desires or requirements. Additionally, it may have psychological benefit to the user by having better control of the functions of the system. Still furthermore, others may have access to the information from the interface system to extrapolate data based on the user's gait and usage, current or historical. If assessing current gait data, the biomechanics portion of the software may allow for real-time analysis much like how a gait lab would provide.

Still furthermore, the GUI may encompass settings for control of an ankle/foot, a knee, and/or a hip joint, amongst others. Each of the above mentioned joints may work in communication with one another or independently, but the setting functions may be similar so that a common GUI template may be used.

Structure of GUI

The graphical user interface (GUI) may be structured as a software component installed separately from a disk, which is provided, to the end user or practitioner. Alternatively the GUI may be automatically launched when the prosthesis system is connected to the computer via a communications link. These descriptions are meant to be illustrative, not limiting the GUI to any particular installation or launch method.

The GUI may be composed of a set of images, which depict buttons, text, and other graphical elements on the computer screen. By interacting with the elements, the user is able to effect changes to the prosthesis system. Additionally, the user may be able to make changes in other ways such as with buttons or switches physically attached to the prosthesis, or through neural interface methods, or by any other method.

Functions of the GUI

The graphical user interface (GUI) may allow for manipulation of variables of the system. This may include settings for resistance variables during various segments of the gait cycle. Additionally, it may include adjustments to the control system equations, or variables thereof. Still furthermore, it may allow for patient information, notes, pictures, biomechanics information and settings, usage information, graphical displays of various forms, warning settings, warning communications methods, internet access, gait lab information, and battery level amongst others. The gait lab information may be provided in a graphical format, which depicts the values of the variables as they change in time. This format may also allow the graphs to be superimposed for comparison purposes. Additionally, the user may be allowed to rotate the data in a three-dimensional view or zoom the display in or out.

The GUI may allow the user to control the feedback variables in the prosthesis as well. Additionally, the GUI may allow for a mechanism for the user to unlock features of the prosthesis, which are only available with a special key.

Biomechanics Data

Biomechanical data may be analyzed through the GUI. This analysis may include a full gait-lab-like assessment abilities. Information for this may be visible by the user in real-time or through reviewing historical data. Additionally, there may be ability to overlay various layers of information in various graphical or display forms to better assess information. Still furthermore, there may be ability to view video and graphical displays in unison. Types of information that may be viewed may be force, terrain, angle, speed, angular velocity, angular acceleration, video, all kinetic and kinematic information, numbers of events such as but not limited to steps, and other forms of information. This list is not meant to be limiting in any way but rather to provide illustrative purposes of available information. Still furthermore, there may be customizable information assessment through tailoring graphical displays. For instance, a graph of any number of variables may have threshold bars, which may limit the range in which a certain variable(s) may be viewed. For instance, a graph showing number of steps per day may be refined to view steps per day between certain hours or between certain terrain levels. This example is not meant to be limiting, but is rather used for explanatory purposes only.

Numerous variables are able to be defines within this system to compare any other variable. Below is an elaborated illustration of examples of variables that may be selected. It is understood however that this is in not a comprehensive list and should not be considered limiting in any way.

Biomechanics Lab System

1. Enables the User to set, alter, update, store, and retrieve Patient's and Practitioner's Name as well as the date (Month, Day, and Year) the Patient's file was last updated.
2. Graph Manipulation:
   a. Animation—Mobile real-time plotting of device extracted, user-specified data
   b. Toggle Animation on and off.
   c. Select a static graph type from among the following: Pie, Line, Bar, Cone, Area, Stock, Radar, Bubble, Column, Surface, Cylinder, Pyramid, XY (Scatter), Doughnut, Area Blocks, B & W Area, B & W Column, B & W Line (Time Scale), B & W Pie, Blue Pie, Colored Lines, Column-Area, Column with depth, Cones, Floating Bars, Line-Column, Line-Column (2-Axis), Line (2-Axis), Logarithmic, Outdoor Bars, Pre Explosion, Smooth Lines, Stack of Colors, Tubes, etc.
   d. Display either 1, 2, or 3 graph(s) (unique, identical, and/or same type or unique type) at once.
   e. Display either 1, 2, 3, or 4 Joint(s) (unique, identical, and/or same type or unique type) data on the graph(s) displayed.
   f. Start Animation—Evoke (begin, launch) Animation.
   g. Record Animation—Store Animation with time stamp for later use.
   h. Replay Animation—Retrieve and plot previously stored (recorded) Animation.
   i. Stop Animation—Stop (halt indefinitely) Animation.
   j. Resume Animation—Continue Animation.
   k. Pause Animation—Freeze Animation.
3. Joint Record Manipulation:
   a. Joint Specification:
      i. Enables the User to select the Joint Record Number (Joint #1, Joint #2, Joint #3, Joint #4) in order to denote the specified Joint Record.
      ii. Enables the User to select the Joint Type (Ankle, Hip, Hand, Wrist, Elbow, Hand, Shoulder, etc.) with respect to specified Joint Record.
      iii. Enables the User to select up to 4 Joint Records (inclusive) indexed by the combination of a Joint Record Number and Joint Type as a key for the Joint Record.
   b. Biomechanics Range Specification:
      i. Enables the User to select Joint-Specific Biomechanics Type parameters as follows:
         1. Ankle, Hip, and Knee—Number of Gait Cycles, Number of Stumbles, Amount of Force, Angle Occurrence, Amount of Resistance, Angular Velocity, Step Length, Stance Time, and Myoelectric Specifics.
         2. Hand—Number of Actuations, Openings, Closings, Thumb Adductions, Thumb Abductions, and Myoelectric Specifics.
         3. Wrist—Number of Actuations, Flexions, Extensions, Pronations, Supanations, Adductions, Abductions, and Myoelectric Specifics.
         4. Elbow—Number of Actuations, Flexions, Extensions, and Myoelectric Specifics.
         5. Shoulder—Number of Actuations, Flexions, Extensions, Pronations, Supanations, Adductions, Abductions, Rotations, and Myoelectric Specifics.
      ii. Enables the User to select Joint Specific Range Type/Terrain parameters as follows:
         1. Ankle, Hip, Knee (Lower Extremity=>Terrain or Range Type)—Incline, Decline, Level Ground, or All Terrains.
         2. Hand, Wrist, Elbow, Shoulder (Upper Extremity=>Range Type)—Force, Angle, Resistance, Angular Velocity.
         3. Specialty Biomechanics Type-Specific Range Types:
            a. Force—If this item is selected as a Biomechanics Type then the Range Types that are selectable are Angle, Resistance, and Angular Velocity meaning that the User is able to view a graph of the amount of force that is placed on the selected joint at either a single angle, resistance, or angular velocity or between two angles, resistances, or angular velocities inclusively.
            b. Angle—If this item is selected as a Biomechanics Type then the Range Types that are selectable are Force, Resistance, and Angular Velocity meaning that the User is able to view a graph of the angle of the selected joint at either a single force, resistance, or angular velocity or between two forces, resistances, or angular velocities inclusively.
c. Resistance—If this item is selected as a Biomechanics Type then the Range Types that are selectable are Angle, Force, and Angular Velocity meaning that the User is able to view a graph of the amount of resistance that the selected joint produces at either a single angle, force, or angular velocity or between two angles, forces, or angular velocities inclusively.
d. Angular Velocity—If this item is selected as a Biomechanics Type then the Range Types that are selectable are Angle, Force, and Resistance meaning that the User is able to view a graph of the angular velocity that the selected joint produces at either a single angle, force, or resistance or between two angles, forces, or resistances inclusively.
iii. Enables the User to Select Range Type-Specific or Terrain-Specific High and Low Range parameters as follows:
1. Ankle [Terrain (Incline, Decline, Level Ground, All Terrains)]—Low Range (HS, FF, MS, HO, or TO) and High Range (HS, FF, MS, HO, or TO), where Low Range is an instance of occurrence less than or equal to the instance of occurrence of High Range [i.e. Low Range=HS then High Range=(HS, FF, MS, HO, or TO), Low Range=FF then High Range=(FF, MS, HO, or TO), etc.].
2. Hip [Terrain (Incline, Decline, Level Ground, All Terrains)]—Low Range (Flexion or Extension) and High Range (Flexion or Extension), where Low Range is an instance of occurrence less than or equal to the instance of occurrence of High Range [i.e. Low Range=Flexion then High Range=(Flexion or Extension), Low Range=Extension then High Range=(Extension), etc.]
3. Knee [Terrain (Incline, Decline, Level Ground, All Terrains)]—Low Range (Stance Flexion, Stance Extension, Swing Flexion, or Swing Extension) and High Range (Stance Flexion, Stance Extension, Swing Flexion, or Swing Extension), where Low Range is an instance of occurrence less than or equal to the instance of occurrence of High Range [i.e. Low Range=Stance Flexion then High Range=(Stance Flexion, Stance Extension, Swing Flexion, or Swing Extension), Low Range=Stance Extension then High Range=(Stance Extension, Swing Flexion, or Swing Extension), etc.]
4. Force, Angle, Resistance, Angular Velocity—Low Range and High Range are governed by the following: 0 units, 1 Unit, 2 Units, . . . Max Units, where Max Units are the maximum Units of force, angle (degrees), resistance, or angular velocity that can be experienced by a Joint and Low Range is less than or equal to High Range.
c. Target Data Time Period:
i. Enables the User to Select Joint Record-Specific Time Span Parameters as Follows:
1. Enables the User to Select Time Span scope [Per Day (24 hours), Per Month (30 Days {30 Days Times 24 Hours}), Per Year (12 Months {12 Months Times 30 Days Times 24 Hours}] parameters
2. Enables the User to Select Time Span Scope-Specific quantity parameters as follows:
a. Per Day—1 day, 2 days, 3 days, . . . , 30 days.
b. Per Month—1 month, 2, months, 3 months, . . . , 12 months.
c. Per Year—1 year, 2 years, 3 years, . . . , 10 years.
3. Enables the User to select a starting day (Month, Day, Year) and computes the remaining span of events given the Joint Record-Specific Time Span Parameter and the Time Span Scope-Specific parameter.
d. Joint Record Manipulation:
i. Enables the User to select any combination of Joint Record parameters over 3a to 3c (inclusive) within the specified User utilization methodologies described above (i.e. ankle-specific parameters combinated with ankle specific selections, wrist-specific parameters combinated with wrist-specific selections, elbow-specific parameters combinated with elbow-specific selections, etc.)
4. File Operations:
a. New—Enables the User to create a new patients data file. This procedure clears the components of all forms associated with the Biomechanics System software and resets the components input data to their defaults. Note that the default inputs of these forms consist of the data that appears or not in the User-manipulatable areas of these associate forms as well as the main Biomechanics System form.
b. Open—Enables the User to search, find, retrieve, and open to form a previously stored (existing) patient Biomechanics file from the hosting computer's file directory. Note that only files with the "." Extension having the Biomechanics System data format are readable by the Biomechanics System.
c. Save—Enables the save [overwrite (store)] a currently open (see 4b. above) and existing patient Biomechanics file to the hosting computer's file directory.
d. Save As—Enables the User to search, find, retrieve, and open or create a file folder and save (store) to directory a non-existing User-defined and created patient Biomechanics file in the hosting computer's file directory. Note that only files created with the Biomechanics System automatically have the "." Extension having the Biomechanics System data format when stored in the hosting computer's file directory.
e. Print—Enables the User to send the currently open (see 4b. above) patient Biomechanics data file formatted, structured, and well organized to a User-selected printer for output.
5. Patient:
a. Enables the User to Set the Practitioner attending to the Patient as well as the date (Month, Day, and Year) that the Practitioner set by the User updated the Patient Form.
b. Enables the User to Set the Patient's Picture (Photo of Patient), First Name, Middle Initial, Last Name, Date (Month, Day, and Year) of Birth, Height (feet and inches), Weight (Pounds and Ounces), and Social Security Number (9 numerical digits).
c. Enables the User to set the Patient's contact information [Address (Street Address, City, State, and Zip Code)

and Phone Number (3-digit area code, 3-digit prefix, and 4-digit suffix)] and Practitioner comments about the patient.
- d. New—Enables the User to Clear the form of the above [5a to 5c (inclusive)] data.
- e. Open—Enables the User to Open an existing Patient file consisting of the above [5a to 5c (inclusive)] data and display it to Patient form.
- f. Save—Enables the User to Save (store) User constructed Patient data consisting of the above [5a to 5c (inclusive)] data from Patient form to a newly created patient file.
- g. Save As—Enables the User to Save (store) User updated Patient data consisting of the above [5a to 5c (inclusive)] data from Patient form to an existing patient file.
- h. Print—Enables the User to print the Visible Patient Data consisting of the above [5a to 5c (inclusive)] data to a User selected printer.
- i. Get Picture—Enables the User to search through the directory of files on the hosting computer and select a picture file (".jpg", ".gif", ".png", ".bmt", etc.) to display in the Patient form. The selected picture file automatically displays once the User selects and opts to open the picture file.
- j. Exit—Enables the User to exit (close) the Patient form and return to the Biomechanics Form (Main Form).

6. Get Movie:
- a. Enables the User to Render and manually (via mouse and/or command buttons) manipulate three-dimensional animated and/or static modal of joint under observation by the User by way of the Biomechanics Form (Main Form).
- b. Play—Enables the User to run (simulate animation) the three-dimensional joint (in motion) in real-time as well as utilizing stored data from a previous joint cycle.
- c. Record—Enables the User to record (store) real-time joint simulations from screen to file.
- d. Replay—Enables the User to re-run (simulate animation) the stored data from a previous joint cycle.
- e. Resume—Enables User to re-evoke Play (denoted above in 6a) after a Pause (denoted below in 6h) action taken by the User.
- f. Rewind—Enables the User to back track currently Playing (denoted in 6a above) data animation simulation to a specified instance in time of the joint cycle.
- g. Fast Forward—Enables the User to forward track currently Playing (denoted in 6a above) data animation simulation to a specified instance in time of the joint cycle
- h. Pause—Enables User to stall current Playing (denoted in 6a above) data animation simulation at a specified instance of time in the joint cycle.
- i. Stop—Enables the User to stop (halt indefinitely) the Playing (denoted in 6a above) data simulation animation.
- j. Exit—Enables the User to exit (close) the Movie form and return to the Biomechanics Form (Main Form).

7. Enables the User to launch, manipulate, alter, update, and share both communication and data resources with other Martin Bionics software designs such as Ankle System, Knee System, and Sensory Feedback Systems.

8. Advanced—Enables the User to set joint specific data parameters to alter the state of the joint specified by the User with respect to data storage and retrieval, timing, computation, simulation, graphics display (static and animated), etc.

9. Instructions—Enables the User to view structured and well organized, step-by-step instructions for manipulating User-Specified components and facilitations of the Biomechanics System Software.

10. Training—Enables the User to both virtually and manually simulate exercise interfacing with the Biomechanics system by way of three-dimensional world manipulations and facilitations utilizing physical prosthetic joints and computer input devices such as keyboards, mouse, monitor, and/or connections to the USB port(s) and/or COM port(s).

11. Help—Enables the User to access and read through a collection of structured, well-organized, and formatted web documents (".HTML" files) which both describe the components of the Biomechanics software in detail and provide step-by-step, detailed instructions for facilitating User Interfacing with the Biomechanics System software.

12. Exit—Enables the User to Terminate (Exit indefinitely) program Execution.

Transfer of Biomechanics Information

The biomechanics information and data may be stored in the ankle electronics, software, microprocessor, or the like, and may be transferred to the GUI software, computer, or other internet site by any means known in the art of computing. This allows for stored usage data of the device to be transferred to others for testing, research, and analysis, statistical analysis, and data collection.

Still furthermore, the software may be updatable for the practitioners in the field or to the users of the device by connecting via internet or other means to download, or similar, the updated or renewed software. If each time that the patient, or user's, prosthesis, orthotic, or robotic device is connected to the practitioner's or user's computer to adjust settings or similar, the biomechanics or usage information is downloaded, then when the new software is updated or renewed, it may automatically transfer that information for compiled research analysis of many users. This usage information may be valuable to a prosthetics, orthotics, or robotics manufacturer.

Still furthermore, connecting the GUI to a main computer may come about through wireless means, or wired means. If wired means are utilized, the data connection port may be located through the proximal pyramid site. This may be a beneficial area to connect data through because it is well protected from the environment. Additionally, the connectivity site may be located at any other area of the prosthesis.

Other Preferred Embodiments

Additionally, it is contemplated that invention 10 may be used in conjunction with myoelectric muscle contacts on the residual limb 404 for trans-tibial amputees and may provide greater control in ambulation. By example, at heel strike, tibialis anterior or other complimentary muscles contraction may be used to determine the level of damper resistance preventing or reducing too fast or too much plantarflexion as would be found in eccentric muscle contractions during ambulation. Also, increased gastrocnemeous or other complimentary muscles contraction during midstance may initiate dorsiflexion resistance sooner or stiffer to allow keel 12 to remain in increased plantarflexion from midstance to toe off, therefore increasing push off may be utilized in fast walking or running. In general anatomical muscle contraction, nerve signals, or the like, all of which categorize neural input in general, to control eccentric, concentric, or isometric motions may be used to alter the state of the damper system during use to optimize safety, symmetry, and biomechanical movement. This may come about through surface or implanted myoelectric-like devices, pattern recognition systems, or any other form of neural input to the device. Still furthermore, the use of a graphics user interface (GUI) may be used to best characterize the form of neural input or equivalent to be best tailored to the prosthetic, orthotic, or robotic output.

Furthermore, invention 10 may be used in conjunction with an orthotic device for a user who has lost the ability to actively plantarflex and/or dorsiflex their natural foot. It is contemplated that invention 10 dampening system 18, sensor system 22, microprocessor unit 172 and/or other elements or combinations thereof device may be located on the medial and/or lateral side of an orthotic brace and would control plantarflexion and dorsiflexion in a similar manner as is described above. Still furthermore, dampening system 18 may be used prosthetically, orthotically, or robotically to control and manage other joints such as knee, hip, elbow, and the like.

Still furthermore, it is contemplated to provide an energy return adjustable heel height prosthetic foot. In a preferred embodiment, a manual or electronic lock may control the dampening system 18 to adjust heel height. It is contemplated that this embodiment may not necessarily require sensory feedback system 22 or microprocessor unit 172 but may use the dampening system 18 to manually lock the ankle joint assembly 16 at a given angle to provide a user adjustable varied heel height foot. Furthermore, the mechanical components described, in general, may be used with less electronics to provide a simpler functioning, or simpler control technique of a largely mechanical system. Furthermore, the dampening system 18 may be altered to be an ankle unit only, with no keel, in order to be attached to other keel designs, or prosthetic feet in general.

Accordingly, other implementations are within the scope of the following claims. Changes may be made in the combinations, operations, and arrangements of the various parts and elements described herein without departing from the spirit and scope of the invention.

Still furthermore, the disclosed invention, incorporating foot/ankle, knee, and/or hip joints may be used in combination with not only prosthetics, orthotics, and robotics devices, but may be used to allow an able-bodied person to ambulate through mechanisms that prevent movement in their own limbs and rely on the functions of the said device.

Knee and Hip Mechanisms

The control and function of a prosthetic knee or hip may be operated from similar information as the ankle device, and may incorporate information from the ankle such as but not limited to angle, force, angle of given force, terrain, speed, angular velocity, angular acceleration, force feedback, valve position, strain gauge, sensor, timing, defining point initiation, and other types of information, including any form of neural input, to control the functions of such a device, in both active powered and resistive manners.

The knee or hip mechanisms may work independently from functions of the ankle device, or may utilize data from the ankle to provide functions of the knee and/or hip. This may be important whereas if communication is lost between the knee and ankle for instance, the knee's functions should remain stable for the user, but may be enhanced when in combination with sensor data from the ankle. The described illustrations should not be considered limiting in any way and are used for illustrative purposes for those skilled in the art. It is contemplated that numerous methods of illustration are conceivable.

For the purposes of explanation, a computer controlled knee working independently from any information from the ankle device may function according to:

Stance Flexion=when angle change in flexion direction, and force above threshold, GUI setting.

Stance Extension=angular change in extension, and force greater than threshold, then GUI setting.

Swing Flexion=force less than threshold, then GUI setting.

Swing Extension=force less than threshold, and angle change in extension direction, the GUI setting.

It should be understood that the term GUI setting may include angular change, angular velocity, force resistance, speed, movement in general, valve placement, etc., and should not be considered limiting. This may correspond to a predetermined or pre-set variable in movement parameters. This would be equivalent for all such knee or hip equations. While the knee is illustrated in these equations, similar or complimentary equations may be used for hip movement, while maintaining necessary variable alterations according to the hip's specific movement during ambulation and other activities. The GUI setting may furthermore be predetermined range of values, whereas the amount of resistance or other variable may change in relation to other variables. For instance, as the angle changes, the valve may close to provide increased resistance to limit the amount of angular velocity with respect to knee angle.

Additionally, functions such as preventing the knee or hip from bending faster than a certain degrees per second may be implemented as a safety factor, whereas the valve continually closes corresponding to forces to maintain an angular velocity above a set threshold. This may be provided as a GUI setting in and of itself.

In a preferred embodiment, the goal of the system may be to maintain a constant, or correspondingly different from constant angular velocity. As force may increase, and knee is bending, valve position may close for instance to maintain a constant angular velocity. Alternatively, it may be desired to allow the knee to bend at slightly faster or slower angular velocities corresponding to knee angle and forces.

These above equations may also include force value from strain gauges or other sensors to control valve placement or angular velocity of the system. This may include a linear or non-linear equation to correspond force to GUI setting alteration.

Additionally, as speed may increase, may alter the valve placement to alter the angular velocity, and pendular, and dynamic characteristics of the knee (and hip). Speed may functionally be correlated to force for certain activities. These equations may as well include functions corresponding to force changes, speed changes, terrain changes, and have learning algorithms associated with them.

Additionally, if system is able to communicate with the ankle for instance, then the below equations may express possible control function parameters, however, they are not intended to be limiting in any way. It is understood that many of the variables, equations, methods, and other, that the ankle joint may utilize or characterize, may be equivalently implemented into other joints such as but not limited to the knee and hip.

STANCE EXTENSION may be minimal resistance at pre-set GUI setting in extension direction only, or may be altered with respect to the heel strike or foot flat to toe off valve placement settings equation for the ankle, and force may be greater than a given threshold.

Stance extension may be defined by foot flat having occurred. Stance extension may be characterized further as being a pre-set or variably adjusted angle range. For instance, it may be defined as from 15 degrees of knee flexion to full extension. For the range of 180 degrees of flexion (or full flexion) to that set 15 degrees of flexion, the resistance may be set at a different amount, or may be near zero in the extension direction only. This may as well be altered corresponding to sensor information from the foot.

STANCE FLEXION may be characterized by heel strike having occurred at the foot and for force to be greater than a given threshold at the foot or knee or hip. Resistance may be altered through the equation: average angular velocity experienced from heel strike to current up to foot flat minus average angular velocity historically from heel strike to foot flat, multiplied by a multiplying factor of N4 degrees per X4 degrees per second, then added to the GUI valve placement at heel strike. This is from the ankle equations. Furthermore, the angle of the knee may be corresponding to the ankle equation for angle with respect to terrain, and may utilize the variables ((foot flat angle experienced minus foot flat angle level ground)+midstance GUI setting). Still furthermore, stance flexion may be further defined by pre-set, or moving according to sensor information, angle range. For instance, stance flexion may be from full extension to having say 15 degrees of knee flexion. This value is not meant to be limiting but is meant for illustrative purposes only. Stance flexion past this set or moving value (say from 15 to 180 degrees) may be characterized by force greater than threshold, and knee angle greater than GUI set stance flexion angle. The resistance may as well be altered with respect to heel strike or foot flat to toe off valve position setting equation from the ankle. This approach may also utilize its own N/X multiplying value.

SWING FLEXION may be characterized by toe off having occurred at the foot, and force being less than a threshold at the foot or knee or hip. Also may alter resistance according to the heel strike or foot flat to toe off valve placement equation from the ankle device. Swing flexion may be characterized further as being a pre-set or variably adjusted angle range. For instance, it may be defined as from full extension to twenty-five degrees of flexion. This may as well be altered corresponding to sensor information from the foot. Additionally, there may an additional range where past a set angle value, the resistance may change again to provide smoother transitions and gait overall.

SWING EXTENSION may be characterized by force being less than threshold on the ankle, and an angular change in the extension direction of the knee. Swing extension may be characterized further as being a pre-set or variably adjusted angle range. For instance, it may be defined as from twenty-five degrees of flexion to full extension. Additionally, it may be determined that so long as force is below a threshold, and the limb is moving in the extension direction, the dynamics may be controlled in a given manner through valve placement or similar equation. This may as well be altered corresponding to sensor information from the foot. Additionally, there may an additional range where past a set angle value, the resistance may change again to provide smoother transitions and gait overall.

Figure 50:
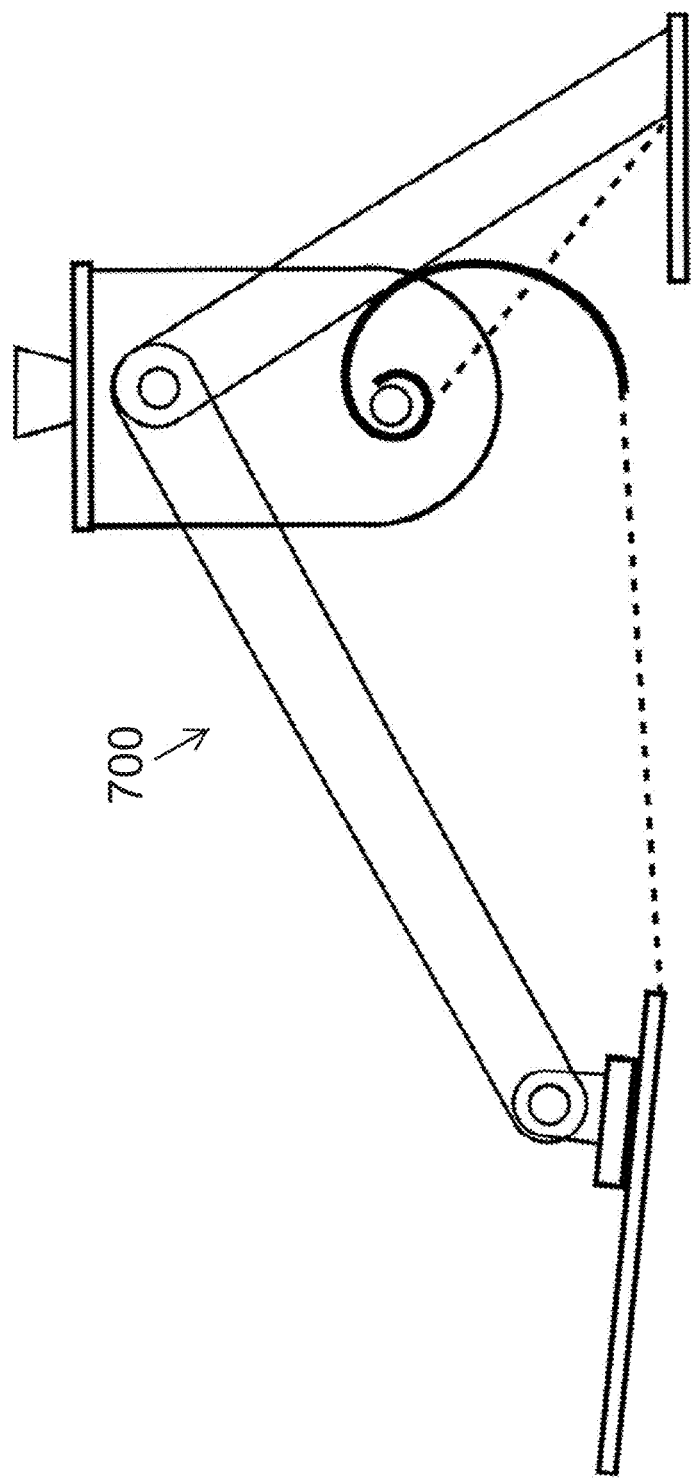
FIG. 50 is a general illustration of a preferred embodiment in accordance with the current invention.

Still furthermore, FIG. 50 illustrates a general depiction of resistance variables in knee mechanism. It should be understood again that the hip joints movements may similarly correspond, though customized for the knee joints movements. It is conceivable that the resistance values, or angular velocity, or other variables may be maintained as constant 602, or may be varied according to other sensor data 601. Additionally, it should be understood that FIG. 22 is meant for explanatory purposes only and should not be considered as limiting in any way. Still furthermore, the knee or hip joint movements may correspond in some manner to the movement, sensor data, functions, or other, of the ankle joint.

Mesofluidics

It is contemplated as well that through using powered actuation strategies, the ankle, knee, and hip angle, force, and direction of movement, amongst other variables, may be altered in various other ways to provide proper positioning corresponding to the traversed environment. Sensor information from the foot, or other joints, or neural control input strategies, as well may be used to govern the necessary movement of each joint, and may be used to actively power the device to perform work. An example of this is allowing a prosthetic system for instance to lift a user up a flight of stairs.

Mesofluidic actuators are fluid-based actuators that range from a few millimeters to centimeters in size and use pressurized fluid for the motive force. Mesofluidics provide high force density (greater than 1000 psi), low friction, direct drive, high mechanical bandwidth and can utilize a variety of working fluids ranging from oil to water or saline solution.

Comparisons of actuation technologies show the many advantages of hydraulic actuation, specifically mesofluidics, over electromagnetic for high-payload robotics applications. One of the main reasons why hydraulics (versus electric actuators) stems from the observation that the power density of hydraulic actuators is approximately five times greater than electric drives. Other benefits are fast response (high dynamic bandwidth), small packaging volume (i.e., power to volume ratio typically 5 to 10 times that of an electric system), and load holding capabilities, as well as inherent compliance.

It should be pointed out that hydraulic actuators are fundamentally different than electric motors in that they have no limitations analogous to the thermal (due to I2R losses) limitations associated with electric motors since the hydraulic fluid cools and lubricates the system. The amount of flow into a hydraulic actuator is limited only by the maximum amount of flow possible from the pumping source and any flow restrictions caused by the flow control elements such as servo valves and component material pressure limitations. On the other hand, electric motors are low force, high-speed systems that require some form of transmission to move a mechanical load, which further increases the overall weight and size of the actuation system. The force or torque that can be produced by hydraulic actuators can typically be easily matched to the application simply by changing the effective area for a linear actuator or the effective displacement for a rotary actuator. Therefore, a transmission system is typically not required for a hydraulic system. As mentioned before, the overall robustness to shock loads is extremely good for hydraulic components.

The disclosed invention may utilize mesofluidic actuation strategies, along with its associated control program technology, to provide a prosthetic system with active power actuation, augmented actuation, or other types or combinations of actuations strategies.

Furthermore, with using active powered joints in real-time during stance and swing characteristics, associated sensor technology may be used, including but not limited to the position of the device in relation to the environment, the angle of the device with respect other joints or the environment, the direction of gravity, force, angle, or other sensors, calculated information based off of sensors, comparison of sensor data to software or the like to determine defining moments during the gait cycle, other calculated information such as through using geometry or mathematics to determine relative distance of the device from the environment based off of joint angle sensors, or the like.

Another Preferred Embodiment

Figure 46:
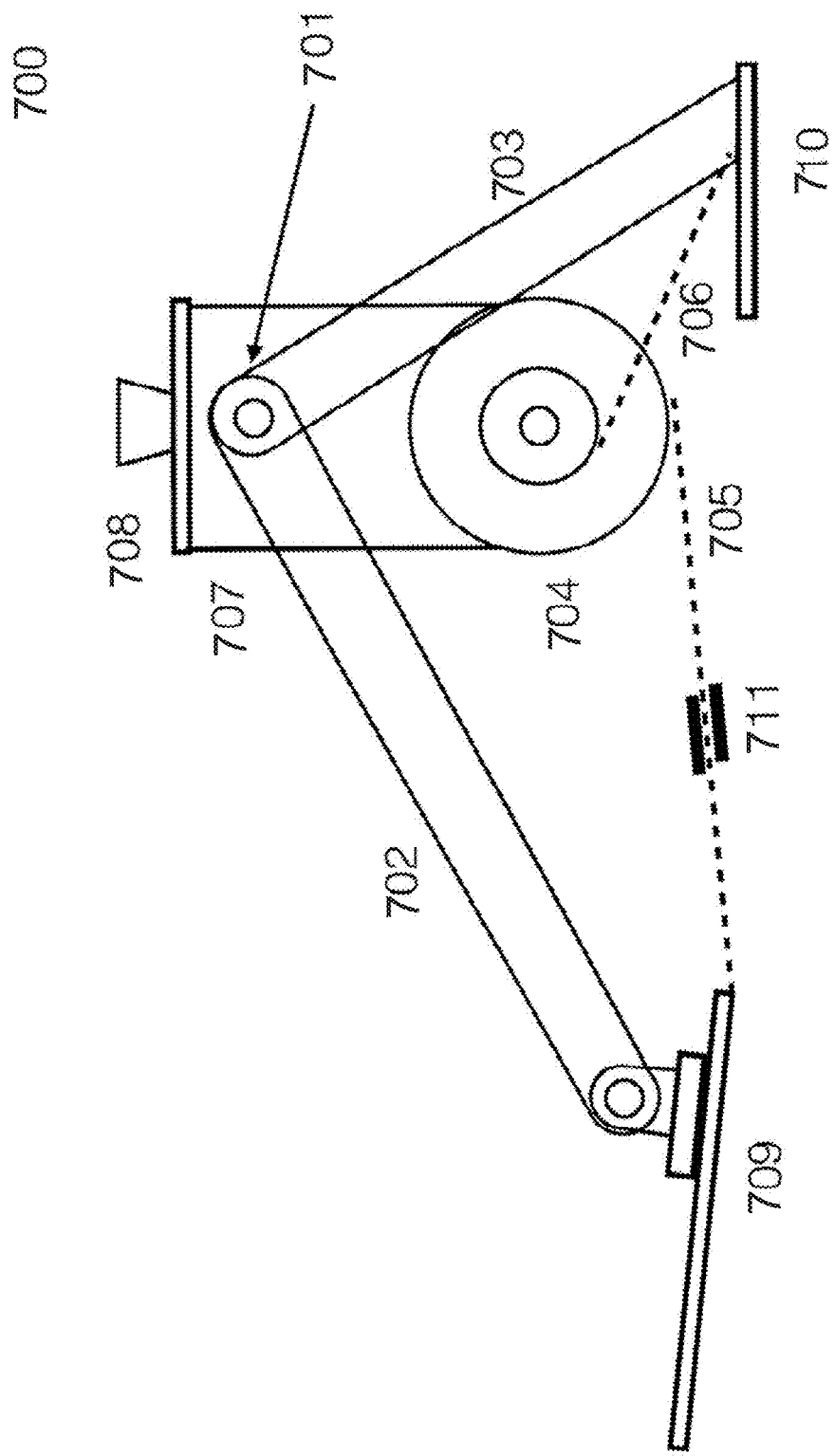
FIG. 46 is a general illustration of a preferred embodiment in accordance with the current invention.

Referring to FIG. 46 an ankle joint may generally rotate about a joint 701. Such joint may generally provide a separate axis for an anterior section of foot 702 and a posterior section of foot 703. Each anterior and posterior section may independently rotate about a single or multiple joints. Their respective rotation may be indirectly linked together such as that the anterior section of foot 702 and the posterior section of foot 704 may exhibit asymmetrical rotation from one another.

The anterior and posterior sections of the foot may be independently linked to a common central axis 704. Such linkages 705 and 706 may utilize any number of materials or methods, but in a preferred embodiment, it may use a flexible member such as but not limited to a type of webbing, cable, vecran, or categorically similar materials. Such linkages 705 and 706 may be attached to the common central axis 704 in independent areas, each constituting different effective rotational characteristics, such as but not limited to cam shapes or varying radii.

As weight may be applied to the posterior section of foot 703, it may cause such section to move upward with respect to its axis 704. Through the linkages, the anterior section of foot 702 may be simultaneously moved downward with respect to its axis 704. The linkages may each generally rotate around the central axis in their respective positions as such section rotates. As linkage 705 and 706 may each be positioned on such central axis 704 in a way as to provide distinct rotational characteristic, the anterior section of foot 702 may generally rotate through a different range of motion than the posterior section of foot 703 as one of the sections of the foot exhibits forces causing its rotation.

By doing so, heel strike for instance may initiate a general plantarflexion moment of the system, and may allow the anterior section of foot 702 to for instance have a greater range of motion than the posterior section of foot 703 from heel strike through foot flat. This may result in quicker anterior stability of the foot, which may be advantageous for amputees using such a device, by increasing knee stability.

A spring element 711 may be positioned in line with at least one of the linkages or other components, allowing for energy to be stored in the system at certain times when load is applied. Such spring element 711 may be sufficiently strong enough to ensure that it is only loaded during certain times of the gait cycle, and therefore used advantageously for its purpose. It is understood that spring element(s) 711 may be positioned in any number of locations along the system, including in line with the linkages 705 and or 706, within the anterior or posterior sections 702 and or 703, or within the central axis 704, amongst others.

Figure 47:
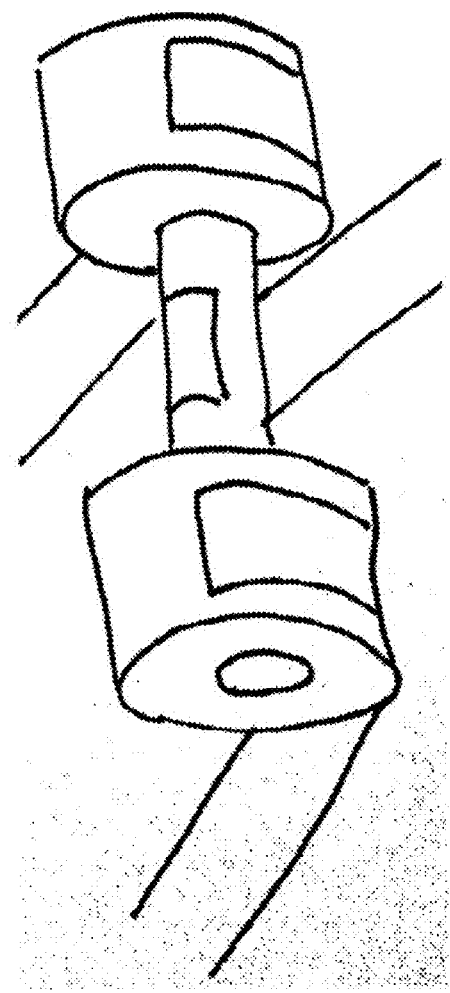
FIG. 47 is a general illustration of a preferred embodiment in accordance with the current invention.

Central axis 704 may generally be connected to bracket 707, which may generally mount to a connection point 708 to attach to the prosthetic. As illustrated in FIG. 47, central axis 704, not drawn to optimized sizing, scale, or shape characteristics, generally illustrates one embodiment of how one may achieve asymmetrical dynamics of the anterior and posterior sections through offering varying diameters of the central axis.

In such a system, anterior section of foot 702 and posterior section of foot 703 may be able to utilize rigid elements as opposed to conventionally used flexible elements, although flexible elements may be used instead. If rigid elements are used, it may allow for a lighter weight device, while maintaining sufficient strength and durability. For instance square stock, tubing, U channel, or the like may be used instead of conventionally used struts, which slightly bend, and may break if excessive load is applied. If U channel may be used, it may allow for rotational flexibility, while maintaining excellent strength in a bending moment.

Such anterior sections and posterior sections may generally be connected to base sections 709 and 710. Such sections may be pivoted, or rigidly connected, and may generally provide slight ground compliance. If anterior base section 709 can be pivoted, it may allow for the functional equivalent of forefoot flexion (bending of the toes) during late stance phase, while simultaneously loading the spring element(s) 711.

During the gait cycle, the central axis 704 may be locked, or transitioned toward a locked position, at various instances in order to provide biomechanical symmetry with the user. Various types of lock mechanisms may be used to prevent rotation of the central axis 704, and hence prevent movement of the anterior section of foot 702 and posterior section of foot 703. While such central axis 704 may generally be in a locked position, an in-line spring or energy storing element 711 may become engaged to store energy, which may be released at another time during the gait cycle.

The central axis 704 shape may include cam shapes, asymmetrical shapes, and varying sizes of various shapes to enable the anterior and posterior linkages and their corresponding anterior and posterior sections to have differing amounts of movement and or rotational change with respect to each other. For instance, the posterior linkage may wrap around a smaller diameter cylinder section of the central axis 704 whereas the anterior linkage may wrap around a larger diameter cylinder section of the central axis, whereby causing the two to have differing amounts of angular change from each other.

During the gait cycle, the central axis 704 may be locked, or transitioned toward a locked position, at various instances in order to provide biomechanical symmetry with the user. Various types of lock mechanisms may be used to prevent rotation of the central axis 704, and hence prevent movement of the anterior section of foot 702 and posterior section of foot 703. While such central axis 704 may generally be in a locked position, an in-line spring or energy storing element 711 may become engaged to store energy, which may be released at another time during the gait cycle.

Heel strike: The central axis lock mechanism (not shown in the simplified illustration) may generally allow for controlled plantarflexion of the ankle.

Foot flat: The central axis may transition to becoming locked at or at a controlled angular (or other) change after foot flat is achieved. Foot flat may be defined by an angular change from plantarflexion to dorsiflexion angle during the gait cycle. Energy storage may begin at or near this portion of the gait cycle, once the central axis becomes locked, and the angle may be changing during roll over. Such angle change may come about through an energy storage mechanism, versus through axis angle change alone.

Midstance: The central axis may transition to becoming locked at or at a controlled angular (or other) change at or near midstance. This may be a defined moment past foot flat.

Heel off: This may be a defined moment past midstance, and may generally allow for the toe section to continue to load the energy storing element.

Toe off: This may be a defined moment and may initiate the lock mechanism to be released at or just before, in order to provide energy back to the user during the final portion of the stance phase.

Control of such lock mechanism, and determination of defining moments and gait cycle moments may come about through computer controlled means, or may come about mechanically, or a combination thereof. For instance, the determination of heel strike may come about through sensor data such as looking at an angular change in the plantarflexion direction, a force sensor, or others, which may tell a computer to engage an actuated lock mechanism. Likewise, heel strike force or angular change of the unit may mechanically engage a lock mechanism to accomplish the same, without the user of a computer. Such control program may be accomplished in principle with similar means, although the tool set to accomplish such mechanisms may differ. The characteristics of such a central axis may be adjustable by the end user or practitioner to enable for customized asymmetrical (or symmetrical) characteristics of the dynamics of the anterior section and posterior section of the foot.

It is understood that invention 700 may consist of various embodiments departing from those shown, and those shown should not be considered limiting. In one embodiment, such central axis lock mechanism may utilize principles from a common seat belt unit to provide the locking. This may be initiated mechanically or electronically.

Likewise, in another embodiment, such central axis lock mechanism may utilize principles from brakes, such as but not limited to pad or disc brakes. This may utilize common parts, or modified designs of parts, from bicycles, motorcycles, automobiles, or other machinery braking mechanisms. In the instance of using parts from bicycles, a unit may be created whereas common bike parts may be used to fabricate or repair such an ankle mechanism.

Figure 49:
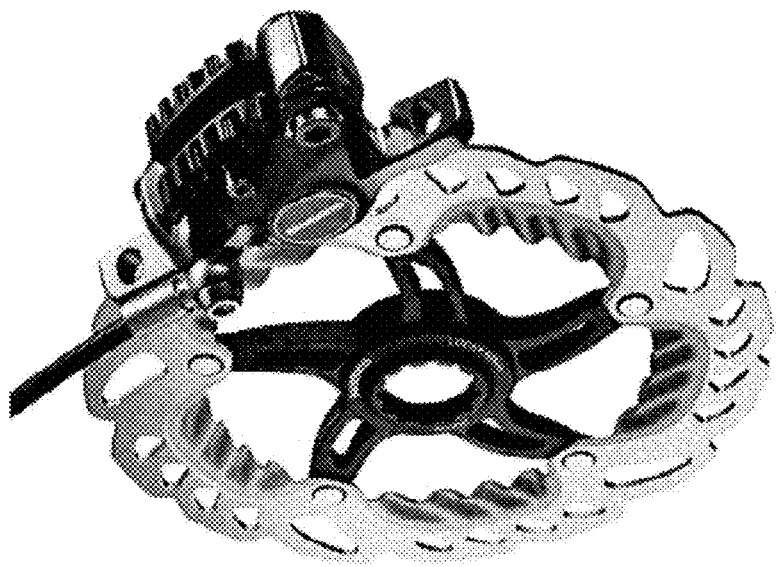
FIG. 49 is a general illustration of a prior art braking system.
Figure 48:
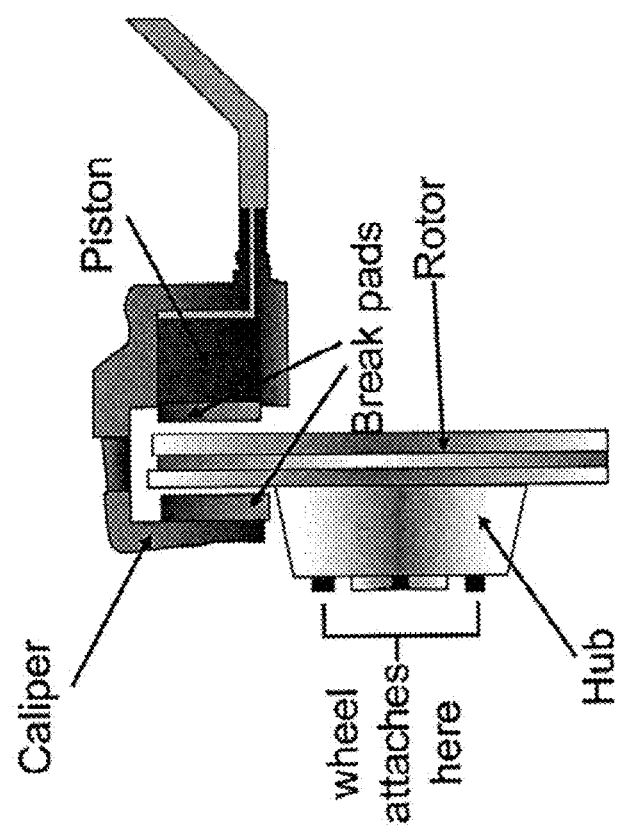
FIG. 48 is a general illustration of a prior art braking system.

In common bike disc brake units, as illustrated in FIGS. 48 and 49, the brake is initiated through a mechanical hand lever, which may close the brake unit mechanically or hydraulically. Using such an example, the functional equivalent of the hand brake mechanism from a bike may be initiated through weight bearing onto the device, or may become engaged through the plantarflexion moment or movement that occurs at or after heel strike, or may be initiated through electronic and or sensor input, with or without an actuator. For instance, an electronic sensor may initiate a small actuator, which may allow a mechanical loading of the functional equivalent of a hand brake unit to engage the disc brake. By doing such, intelligent control may be used for the exact timing and or dynamics of how the brake may be engaged, but the force to close such a brake could come about through actual body weight dynamics, versus relying on a considerably larger actuator than would be used otherwise. If just a small actuator is used to engage or enable the body weight to actually lock out the brake, it could be considerably more energy efficient.

At least a portion of such a disc brake may be utilized within the space of a prosthetic device, as the unit would likely not rotate multiple revolutions as would occur in a bike example, and likely would not rotate past a few degrees in total. Further, the sizing, positioning, and mechanical gearing of such a system may such that it optimizes the function of such a system for use in a prosthetic or orthotic device. Such approach for a locking or actuator mechanism for a prosthetic or orthotic device would enable the unit to be comparably lightweight, small, robust, and field serviceable.

It is understood that as an actuator or lock mechanism, it may be equally beneficial as used in a knee joint as in an ankle joint. Likewise, because of its low profile shape, it may be especially advantageous as used in orthotic devices. The use of such a system should not be considered limited to a prosthetic ankle.

Such brake lock mechanism may be integrated within central axis area of the device. In an alternative embodiment as generally illustrated in FIG. 50, central axis may incorporate an energy storing mechanism within its design. In such an example, though not drawn to optimized characteristics, an energy storing spring, or other such energy storing mechanism may be integrated. Such figure should not be considered limiting, as such illustration is purposely over simplified for illustrative purposes, and such embodiment could be configured in a number of methods.

Incorporated in any area of the device may be a spring element, which may cause the device to move into general dorsiflexion during the swing phase of gait. When load is not applied on the unit, and when the lock mechanism is not engaged, the spring element may be stronger than the inertial and static friction forces of the unit, thereby causing it to move into dorsiflexion.

I claim:

1. A prosthetic ankle joint system for a user comprising:
  a bracket having a first end, a length, and a second end;
  a connection point positioned on said first end of said bracket;
  a central axis positioned on said second end of said bracket;
  a joint axis positioned on said length of said bracket;
  an anterior base;
  a posterior base;
  an anterior section having a first end pivotally attached to said joint axis and a second end pivotally attached to said anterior base;
  a posterior section having a first end pivotally attached to said joint axis and a second end attached to said posterior base;
  a first linkage having a first end connected to said anterior base, a second rotationally attached to said central axis and a spring element positioned between said first end of said linkage and said second end of said linkage; and
  a second linkage having a first end connected to said posterior base and a second end rotationally attached to said central axis.

* * * * *